US008007528B2

(12) United States Patent
Yadin et al.

(10) Patent No.: US 8,007,528 B2
(45) Date of Patent: Aug. 30, 2011

(54) BIFURCATED STENT

(75) Inventors: Amnon Yadin, Kfar Vitkin (IL);
Thomas E. Broome, Prior Lake, MN
(US); Michael P. Meyer, Richfield, MN
(US); Eric Williams, Suisun City, CA
(US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1130 days.

(21) Appl. No.: 11/752,837

(22) Filed: May 23, 2007

(65) Prior Publication Data
US 2007/0225796 A1 Sep. 27, 2007

Related U.S. Application Data

(63) Continuation-in-part of application No. 10/802,036, filed on Mar. 17, 2004, now Pat. No. 7,341,598.

(51) Int. Cl.
*A61F 2/06* (2006.01)
(52) U.S. Cl. ..................................................... 623/1.35
(58) Field of Classification Search .................. 623/1.35
See application file for complete search history.

(56) References Cited

U.S. PATENT DOCUMENTS

| 4,309,994 A | 1/1982 | Grunwald | 128/214 R |
|---|---|---|---|
| 4,769,005 A | 9/1988 | Ginsburg et al. | 604/53 |
| 4,774,949 A | 10/1988 | Fogarty | 128/348.1 |
| 4,896,670 A | 1/1990 | Crittenden | 606/194 |
| 4,905,667 A | 3/1990 | Foerster et al. | 128/4 |
| 4,994,071 A | 2/1991 | MacGregor | 606/194 |
| 5,342,387 A | 8/1994 | Summers | 606/198 |
| 5,387,235 A | 2/1995 | Chuter | 623/1 |
| 5,456,712 A | 10/1995 | Maginot | 623/1 |
| 5,476,471 A | 12/1995 | Shifrin et al. | 606/151 |
| 5,487,730 A | 1/1996 | Marcadis et al. | 604/96 |
| 5,591,228 A | 1/1997 | Edoga | 623/1 |
| 5,607,444 A | 3/1997 | Lam | 606/194 |
| 5,609,605 A | 3/1997 | Marshall et al. | 606/191 |
| 5,609,627 A | 3/1997 | Goicoechea et al. | 623/1 |
| 5,613,980 A | 3/1997 | Chauhan | 606/194 |
| 5,617,878 A | 4/1997 | Taheri | 128/898 |
| 5,632,762 A | 5/1997 | Myler | 606/194 |
| 5,632,763 A | 5/1997 | Glastra | 606/194 |

(Continued)

FOREIGN PATENT DOCUMENTS
CA        2220864        7/1999
(Continued)

OTHER PUBLICATIONS

U.S. Appl. No. 09/663,111, filed Sep. 15, 2000, Davidson et al.

(Continued)

*Primary Examiner* — Paul Prebilic
(74) *Attorney, Agent, or Firm* — Vidas, Arrett & Steinkraus, P.A.

(57) ABSTRACT

In at least one embodiment, a stent comprises a plurality of interconnected framework members defining a plurality of cells. A portion of the interconnected framework members comprise a side branch structure defining an inner side branch cell that is shaped differently from other cells of the stent. The side branch structure comprises a serpentine ring that extends around the inner side branch cell. The serpentine ring comprises alternating struts and turns. The turns comprise alternating inner turns and outer turns, and the inner turns comprise alternating first inner turns and second inner turns. The second inner turns are located farther away from a side branch center point than the first inner turns.

17 Claims, 82 Drawing Sheets

U.S. PATENT DOCUMENTS

| | | | |
|---|---|---|---|
| 5,632,772 A | 5/1997 | Alcime et al. | 623/1 |
| 5,636,641 A | 6/1997 | Fariabi | 600/585 |
| 5,669,924 A | 9/1997 | Shaknovich | 606/108 |
| 5,669,932 A | 9/1997 | Fischell et al. | 606/198 |
| 5,676,697 A | 10/1997 | McDonald | 623/1 |
| 5,683,450 A | 11/1997 | Goicoechea et al. | 623/1 |
| 5,697,971 A | 12/1997 | Fischell et al. | 623/1 |
| 5,707,348 A | 1/1998 | Krogh | 602/41 |
| 5,709,713 A | 1/1998 | Evans et al. | 623/1 |
| 5,720,735 A | 2/1998 | Dorros | 604/284 |
| 5,749,825 A | 5/1998 | Fischell et al. | 600/3 |
| 5,749,890 A | 5/1998 | Shaknovich | 606/198 |
| 5,755,734 A | 5/1998 | Richter et al. | 606/194 |
| 5,755,735 A | 5/1998 | Richter et al. | 606/194 |
| 5,755,771 A | 5/1998 | Penn et al. | 623/1 |
| 5,755,773 A | 5/1998 | Evans et al. | 623/1 |
| 5,755,778 A | 5/1998 | Kleshinski | 623/1 |
| 5,782,906 A | 7/1998 | Marshall et al. | 623/1 |
| 5,824,036 A | 10/1998 | Lauterjung | 623/1 |
| 5,824,040 A | 10/1998 | Cox et al. | 623/1 |
| 5,827,320 A | 10/1998 | Richter et al. | 606/194 |
| 5,851,464 A | 12/1998 | Davila et al. | 264/103 |
| 5,868,777 A | 2/1999 | Lam | 606/194 |
| 5,893,887 A | 4/1999 | Jayaraman | 623/1 |
| 5,906,640 A * | 5/1999 | Penn et al. | 623/1.15 |
| 5,961,548 A | 10/1999 | Shmulewitz | 623/1 |
| 5,972,017 A | 10/1999 | Berg et al. | 606/198 |
| 6,013,054 A | 1/2000 | JiunYan | 604/96 |
| 6,017,324 A | 1/2000 | Tu et al. | 604/96 |
| 6,017,363 A | 1/2000 | Hojeibane | 623/1 |
| 6,030,414 A | 2/2000 | Taheri | 623/1 |
| 6,033,434 A | 3/2000 | Borghi | 623/1 |
| 6,033,435 A | 3/2000 | Penn et al. | 623/1 |
| 6,056,775 A | 5/2000 | Borghi et al. | 623/1.16 |
| 6,059,824 A | 5/2000 | Taheri | 623/1 |
| 6,068,655 A | 5/2000 | Seguin et al. | 623/1 |
| 6,086,611 A | 7/2000 | Duffy et al. | 623/1 |
| 6,093,203 A | 7/2000 | Uflacker | 612/1.12 |
| 6,096,073 A | 8/2000 | Webster et al. | 623/1.16 |
| 6,099,497 A | 8/2000 | Adams et al. | 604/96.01 |
| 6,113,579 A | 9/2000 | Eidenschink et al. | 604/264 |
| 6,117,117 A | 9/2000 | Mauch | 604/284 |
| 6,117,156 A | 9/2000 | Richter et al. | 606/194 |
| 6,129,738 A | 10/2000 | Lashinski et al. | 606/194 |
| 6,142,973 A | 11/2000 | Carleton et al. | 604/96 |
| 6,143,002 A | 11/2000 | Vietmeier | 606/108 |
| 6,159,238 A | 12/2000 | Killion et al. | 612/1.11 |
| 6,165,195 A | 12/2000 | Wilson et al. | 606/194 |
| 6,168,621 B1 | 1/2001 | Vrba | 623/1.2 |
| 6,183,509 B1 | 2/2001 | Dibie | 623/1.35 |
| 6,203,568 B1 | 3/2001 | Lombardi et al. | 623/1.13 |
| 6,210,380 B1 | 4/2001 | Mauch | 604/284 |
| 6,210,429 B1 | 4/2001 | Vardi et al. | 623/1.11 |
| 6,210,433 B1 | 4/2001 | Larre | 623/1.15 |
| 6,254,593 B1 | 7/2001 | Wilson | 606/1.11 |
| 6,258,115 B1 | 7/2001 | Dubrul | 606/200 |
| 6,258,116 B1 | 7/2001 | Hojeibane | 623/1.16 |
| 6,261,305 B1 | 7/2001 | Marotta et al. | 606/200 |
| 6,261,316 B1 | 7/2001 | Shaolian et al. | 623/1.11 |
| 6,264,662 B1 | 7/2001 | Lauterjung | 606/108 |
| 6,264,686 B1 | 7/2001 | Rieu et al. | 623/1.16 |
| 6,290,673 B1 | 9/2001 | Shanley | 604/102.02 |
| 6,293,968 B1 | 9/2001 | Taheri | 623/1.15 |
| 6,325,826 B1 | 12/2001 | Vardi et al. | 623/1.35 |
| 6,334,864 B1 | 1/2002 | Amplatz et al. | 606/200 |
| 6,346,089 B1 | 2/2002 | Dibie | 603/1.15 |
| 6,355,060 B1 | 3/2002 | Lenker et al. | 623/1.34 |
| 6,361,544 B1 | 3/2002 | Wilson et al. | 606/194 |
| 6,361,555 B1 | 3/2002 | Wilson | 623/1.11 |
| 6,383,213 B2 | 5/2002 | Wilson et al. | 623/1.11 |
| 6,395,018 B1 | 5/2002 | Castaneda | 623/1.13 |
| 6,436,104 B2 | 8/2002 | Hojeibane | 606/108 |
| 6,436,134 B2 | 8/2002 | Richter et al. | 623/1.15 |
| 6,508,836 B2 | 1/2003 | Wilson et al. | 623/1.35 |
| 6,517,558 B2 | 2/2003 | Gittings et al. | 606/153 |
| 6,520,988 B1 | 2/2003 | Colombo et al. | 623/1.35 |
| 6,540,779 B2 | 4/2003 | Richter et al. | 623/1.35 |
| 6,579,309 B1 | 6/2003 | Loos et al. | 623/1.16 |
| 6,579,312 B2 | 6/2003 | Wilson et al. | 623/1.35 |
| 6,582,394 B1 | 6/2003 | Reiss et al. | 604/96.01 |
| 6,596,020 B2 | 7/2003 | Vardi et al. | 623/1.11 |
| 6,599,316 B2 | 7/2003 | Vardi et al. | 623/1.15 |
| 6,645,242 B1 | 11/2003 | Quinn | 623/1.16 |
| 6,689,156 B1 | 2/2004 | Davidson et al. | 623/1.11 |
| 6,692,483 B2 | 2/2004 | Vardi et al. | 604/529 |
| 6,695,877 B2 | 2/2004 | Brucker et al. | 623/1.16 |
| 6,706,062 B2 | 3/2004 | Vardi et al. | 623/1.15 |
| 6,749,628 B1 | 6/2004 | Callol et al. | 623/1.15 |
| 6,776,793 B2 | 8/2004 | Brown et al. | 623/1.15 |
| 6,811,566 B1 | 11/2004 | Penn et al. | 623/1.15 |
| 6,835,203 B1 | 12/2004 | Vardi et al. | 623/1.34 |
| 6,858,038 B2 | 2/2005 | Heuser | 623/1.35 |
| 6,884,258 B2 | 4/2005 | Vardi et al. | 623/1.11 |
| 6,896,699 B2 | 5/2005 | Wilson et al. | 623/1.35 |
| 6,932,837 B2 | 8/2005 | Amplatz et al. | 623/1.15 |
| 6,955,687 B2 | 10/2005 | Richter et al. | 623/1.35 |
| 6,955,688 B2 | 10/2005 | Wilson et al. | 623/1.35 |
| 6,962,602 B2 | 11/2005 | Vardi et al. | 623/1.11 |
| 7,018,400 B2 | 3/2006 | Lashinski et al. | 623/1.11 |
| 7,056,323 B2 | 6/2006 | Mareiro et al. | 606/108 |
| 7,060,091 B2 | 6/2006 | Killion et al. | 623/1.15 |
| 7,341,598 B2 * | 3/2008 | Davidson et al. | 623/1.35 |
| 2001/0003161 A1 | 6/2001 | Vardi et al. | 623/1.11 |
| 2001/0004706 A1 | 6/2001 | Hojeibane | 623/1.11 |
| 2001/0004707 A1 | 6/2001 | Dereurne et al. | 623/1.16 |
| 2001/0012927 A1 | 8/2001 | Mauch | 604/284 |
| 2001/0016766 A1 | 8/2001 | Vardi et al. | 623/1.11 |
| 2001/0016767 A1 | 8/2001 | Wilson et al. | 623/1.11 |
| 2001/0016768 A1 | 8/2001 | Wilson et al. | 623/1.11 |
| 2001/0025195 A1 | 9/2001 | Shaolian et al. | 623/1.13 |
| 2001/0027291 A1 | 10/2001 | Shanley | 604/104 |
| 2001/0027338 A1 | 10/2001 | Greenberg | 623/1.13 |
| 2001/0029396 A1 | 10/2001 | Wilson et al. | 623/1.11 |
| 2001/0037116 A1 | 11/2001 | Wilson et al. | 606/108 |
| 2001/0037138 A1 | 11/2001 | Wilson et al. | 623/1.11 |
| 2001/0039448 A1 | 11/2001 | Dibie | 623/1.16 |
| 2001/0049552 A1 | 12/2001 | Richter et al. | 623/1.15 |
| 2001/0056297 A1 | 12/2001 | Hojeibane | 623/1.16 |
| 2002/0013618 A1 | 1/2002 | Marotta et al. | 623/1.15 |
| 2002/0013619 A1 | 1/2002 | Shanley | 623/1.15 |
| 2002/0022874 A1 | 2/2002 | Wilson | 623/1.11 |
| 2002/0026232 A1 | 2/2002 | Marotta et al. | 623/1.16 |
| 2002/0035392 A1 | 3/2002 | Wilson | 623/1.11 |
| 2002/0042650 A1 | 4/2002 | Vardi et al. | 623/1.35 |
| 2002/0052648 A1 | 5/2002 | McGuckin, Jr. et al. | 623/1.35 |
| 2002/0072790 A1 | 6/2002 | McGuckin, Jr. et al. | 623/1.12 |
| 2002/0111675 A1 | 8/2002 | Wilson | 623/1.35 |
| 2002/0156516 A1 | 10/2002 | Vardi et al. | 623/1.11 |
| 2002/0156517 A1 | 10/2002 | Perouse | 623/1.11 |
| 2002/0165604 A1 | 11/2002 | Shanley | 623/1.15 |
| 2002/0173835 A1 | 11/2002 | Bourang et al. | 623/1.11 |
| 2002/0173840 A1 | 11/2002 | Brucker et al. | 623/1.16 |
| 2002/0183763 A1 | 12/2002 | Callol et al. | 606/108 |
| 2002/0193872 A1 | 12/2002 | Trout, III et al. | 623/1.34 |
| 2002/0193873 A1 | 12/2002 | Brucker et al. | 623/1.35 |
| 2003/0009209 A1 | 1/2003 | Hojeibane | 623/1.11 |
| 2003/0028233 A1 | 2/2003 | Vardi et al. | 623/1.11 |
| 2003/0050688 A1 | 3/2003 | Fischell et al. | 623/1.15 |
| 2003/0055378 A1 | 3/2003 | Wang et al. | 604/103.07 |
| 2003/0055483 A1 | 3/2003 | Gumm | 623/1.11 |
| 2003/0074047 A1 | 4/2003 | Richter | 623/1.11 |
| 2003/0093109 A1 | 5/2003 | Mauch | 606/194 |
| 2003/0097169 A1 | 5/2003 | Brucker et al. | 623/1.11 |
| 2003/0114912 A1 | 6/2003 | Sequin et al. | 623/1.11 |
| 2003/0125791 A1 | 7/2003 | Sequin et al. | 623/1.11 |
| 2003/0125802 A1 | 7/2003 | Callol et al. | 623/1.35 |
| 2003/0135259 A1 | 7/2003 | Simso | 623/1.12 |
| 2003/0181923 A1 | 9/2003 | Vardi | 606/108 |
| 2003/0195606 A1 | 10/2003 | Davidson et al. | 623/1.11 |
| 2004/0006381 A1 | 1/2004 | Sequin et al. | 623/1.12 |
| 2004/0015227 A1 | 1/2004 | Vardi et al. | 623/1.16 |
| 2004/0044396 A1 | 3/2004 | Clerc et al. | 623/1.13 |
| 2004/0059406 A1 | 3/2004 | Cully et al. | 623/1.11 |
| 2004/0088007 A1 | 5/2004 | Eidenschink | 607/1 |
| 2004/0117003 A1 | 6/2004 | Ouriel et al. | 623/1.35 |
| 2004/0133268 A1 | 7/2004 | Davidson et al. | 623/1.35 |
| 2004/0138732 A1 | 7/2004 | Suhr et al. | 623/1.11 |

| | | | | |
|---|---|---|---|---|
| 2004/0138737 A1 | 7/2004 | Davidson et al. ............ 623/1.35 | WO | 99/03426 | 1/1999 |
| 2004/0148006 A1 | 7/2004 | Davidson et al. ............ 623/1.11 | WO | 99/04726 | 2/1999 |
| 2004/0172121 A1 | 9/2004 | Eidenschink et al. ....... 623/1.11 | WO | 99/15103 | 4/1999 |
| 2004/0186560 A1 | 9/2004 | Alt ................. 623/1.35 | WO | 99/15109 | 4/1999 |
| 2004/0225345 A1 | 11/2004 | Fischell et al. .............. 623/1.11 | WO | 99/24104 | 5/1999 |
| 2004/0267352 A1 | 12/2004 | Davidson et al. ............ 623/1.15 | WO | 99/34749 | 7/1999 |
| 2005/0004656 A1 | 1/2005 | Das ............................ 623/1.16 | WO | 99/36002 | 7/1999 |
| 2005/0010278 A1 | 1/2005 | Vardi et al. .................. 623/1.35 | WO | 99/36015 | 7/1999 |
| 2005/0015108 A1 | 1/2005 | Williams et al. .............. 606/194 | WO | WO 99/36002 A1 * | 7/1999 |
| 2005/0015135 A1 | 1/2005 | Shanley ....................... 623/1.11 | WO | 99/44539 | 9/1999 |
| 2005/0060027 A1 | 3/2005 | Khenansho et al. ......... 623/1.35 | WO | 99/56661 | 11/1999 |
| 2005/0096726 A1 | 5/2005 | Sequin et al. ................ 623/1.12 | WO | 99/65419 | 12/1999 |
| 2005/0102021 A1 | 5/2005 | Osborne ...................... 623/1.13 | WO | 00/07523 | 2/2000 |
| 2005/0102023 A1 | 5/2005 | Yadin et al. .................. 623/1.15 | WO | 00/10489 | 3/2000 |
| 2005/0119731 A1 | 6/2005 | Brucker et al. .............. 623/1.35 | WO | 00/16719 | 3/2000 |
| 2005/0125076 A1 | 6/2005 | Ginn ........................ 623/23.65 | WO | 00/27307 | 5/2000 |
| 2005/0131526 A1 | 6/2005 | Wong ........................... 623/1.15 | WO | 00/27463 | 5/2000 |
| 2005/0149161 A1 | 7/2005 | Eidenschink et al. ....... 623/1.11 | WO | 00/28922 | 5/2000 |
| 2005/0154442 A1 | 7/2005 | Eidenschink et al. ....... 623/1.11 | WO | 01/45594 | 6/2000 |
| 2005/0154444 A1 | 7/2005 | Quadri ......................... 623/1.13 | WO | 00/44307 | 8/2000 |
| 2005/0183259 A1 | 8/2005 | Eidenschink et al. .......... 29/508 | WO | 00/44309 | 8/2000 |
| 2005/0209673 A1 | 9/2005 | Shaked ........................ 623/1.11 | WO | 00/47134 | 8/2000 |
| 2005/0228483 A1 | 10/2005 | Kaplan et al. ................ 623/1.15 | WO | 00/48531 | 8/2000 |
| 2006/0036315 A1 | 2/2006 | Yadin et al. .................. 623/1.35 | WO | 00/49951 | 8/2000 |
| 2006/0041303 A1 | 2/2006 | Israel ........................... 623/1.11 | WO | 00/51523 | 9/2000 |
| 2006/0079956 A1 | 4/2006 | Eigler et al. ................. 623/1.35 | WO | 00/57813 | 10/2000 |
| 2006/0173528 A1 | 8/2006 | Feld et al. .................... 623/1.15 | WO | 00/67673 | 11/2000 |
| 2007/0073376 A1 | 3/2007 | Krolik et al. ................. 623/1.11 | WO | 00/71054 | 11/2000 |
| 2007/0208418 A1 * | 9/2007 | Hegg et al. .................. 623/1.35 | WO | 00/71055 | 11/2000 |

FOREIGN PATENT DOCUMENTS

| | | |
|---|---|---|
| DE | 9014845 | 2/1991 |
| DE | 29701758 | 3/1997 |
| DE | 29701883 | 5/1997 |
| EP | 0479730 | 10/1991 |
| EP | 0751752 | 1/1997 |
| EP | 0783873 | 7/1997 |
| EP | 0804907 | 11/1997 |
| EP | 0479557 | 7/1998 |
| EP | 0876805 | 11/1998 |
| EP | 0880949 | 12/1998 |
| EP | 0891751 | 1/1999 |
| EP | 0895759 | 2/1999 |
| EP | 0904745 | 3/1999 |
| EP | 0937442 | 8/1999 |
| EP | 0347023 | 12/1999 |
| EP | 1031328 | 8/2000 |
| EP | 1031329 | 8/2000 |
| EP | 0883384 | 12/2000 |
| EP | 0862392 | 8/2001 |
| EP | 0808140 | 12/2001 |
| EP | 0884028 | 2/2002 |
| EP | 1190685 | 3/2002 |
| EP | 0897700 | 7/2002 |
| EP | 0684022 | 2/2004 |
| EP | 1157674 | 7/2005 |
| EP | 1031330 | 11/2005 |
| EP | 1070513 | 6/2006 |
| FR | 2678508 | 1/1993 |
| FR | 2740346 | 10/1995 |
| FR | 2756173 | 11/1996 |
| GB | 2337002 | 5/1998 |
| WO | 88/06026 | 8/1988 |
| WO | 95/21592 | 8/1995 |
| WO | 96/29955 | 10/1996 |
| WO | 96/34580 | 11/1996 |
| WO | 96/41592 | 12/1996 |
| WO | 97/07752 | 3/1997 |
| WO | 97/15346 | 5/1997 |
| WO | 97/16217 | 5/1997 |
| WO | 97/26936 | 7/1997 |
| WO | 97/41803 | 11/1997 |
| WO | 97/45073 | 12/1997 |
| WO | 97/46174 | 12/1997 |
| WO | 98/19628 | 5/1998 |
| WO | 98/36709 | 8/1998 |
| WO | 98/37833 | 9/1998 |
| WO | 98/47447 | 10/1998 |
| WO | 98/48879 | 11/1998 |
| WO | 00/74595 | 12/2000 |
| WO | 01/21095 | 3/2001 |
| WO | 01/21109 | 3/2001 |
| WO | 01/21244 | 3/2001 |
| WO | 01/35715 | 5/2001 |
| WO | 01/35863 | 5/2001 |
| WO | 01/39697 | 6/2001 |
| WO | 01/39699 | 6/2001 |
| WO | 01/41677 | 6/2001 |
| WO | 01/43665 | 6/2001 |
| WO | 01/43809 | 6/2001 |
| WO | 01/45785 | 6/2001 |
| WO | 01/49342 | 7/2001 |
| WO | 01/54621 | 8/2001 |
| WO | 01/54622 | 8/2001 |
| WO | 01/58385 | 8/2001 |
| WO | 01/60284 | 8/2001 |
| WO | 01/70294 | 9/2001 |
| WO | 01/70299 | 9/2001 |
| WO | 01/74273 | 10/2001 |
| WO | 01/89409 | 11/2001 |
| WO | 02/00138 | 1/2002 |
| WO | 02/053066 | 7/2002 |
| WO | 02/068012 | 9/2002 |
| WO | 03/007842 | 1/2003 |
| WO | 03/055414 | 7/2003 |
| WO | 03/063924 | 8/2003 |
| WO | 2004/026174 | 4/2004 |
| WO | 2004/026180 | 4/2004 |
| WO | 2005/009295 | 2/2005 |
| WO | 2005/014077 | 2/2005 |
| WO | 2006/028925 | 3/2006 |
| WO | 2008033412 | 3/2008 |

OTHER PUBLICATIONS

U.S. Appl. No. 09/614,472, filed Jul. 11, 2000, Davidson et al.

U.S. Appl. No. 09/325,996, filed Jun. 4, 1999, Vardi et al.

U.S. Appl. No. 10/802,036, filed Mar. 17, 2004, Davidson et al.

Chevalier, M.D., Bernard, "Placement of Coronary Stents in Bifurcation Lesions by the "Culotte" Technique," *The American Journal of Cardiology*, vol. 82, pp. 943-949 (Oct. 15, 1998).

Nakamura M.D., Shigeru, "Techniques for Palmaz-Schatz Stent Deployment in Lesions with a Large Side Branch," *Catheterization and Cardiovascular Diagnosis*, vol. 34, pp. 353-361 (1995).

Caputo, Ronald P., "Stent Jail: A Minimum-Security Prison," *The American Journal of Cardiology*, vol. 77, pp. 1226-1230 (Jun. 1, 1996).

Colombo, M.D., Antonio, ""Kissing" Stent for Bifurcational Coronary Lesion," *Catheterization and Cardiovascular Diagnosis*, vol. 30, pp. 327-330 (Dec. 1993).

Carrie, M.D., Didier, ""T"-Shaped Stent Placement: A Technique for the Treatment of Dissected Bifurcation Lesions," *Catheterization and Cardiovascular Diagnosis*, vol. 37, pp. 311-313 (Mar. 1996).

Katoh, M.D., Osamu, "New Double Wire Technique to Stent Ostial Lesions," *Catheterization and Cardiovascular Diagnosis*, vol. 40, pp. 400-402 (Apr. 1997).

Lewis, M.D., Bruce E., "Acute procedural results in the treatment of 30 coronary artery bifurcation lesions with a double-wire atherectomy technique for side-branch protection," *American Heart Journal*, vol. 127:6, pp. 1600-1607 (Jun. 1994).

Yamashita, M.D.,PhD., Takehiro, "Bifurcation Lesions: Two Stents Versus One Stent—Immediate and Follow-up Results," *Journal of the American College of Cardiology*, vol. 35:5, pp. 1145-1151 (Apr. 2000).

Satler, M.D., Lowell F., "Bifurcation Disease: To Treat or Not to Treat," *Catheterization and Cardiovascular Interventions*, vol. 50, pp. 411-412 (2000).

\* cited by examiner

BIFURCATED STENT

CROSS-REFERENCE TO RELATED APPLICATIONS

This Application is a continuation-in-part of U.S. patent application Ser. No. 10/802,036, filed Mar. 17, 2004 now U.S. Pat. No. 7,341,598, the entire contents of which is hereby incorporated herein by reference.

BACKGROUND OF THE INVENTION

1. Field of the Invention

In some embodiments this invention relates to implantable medical devices, their manufacture, and methods of use. Some embodiments are directed to delivery systems, such as catheter systems of all types, which are utilized in the delivery of such devices.

2. Description of the Related Art

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature, it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, a stent comprises a plurality of interconnected framework members defining a plurality of cells. A portion of the interconnected framework members comprise a side branch structure defining an inner side branch cell that is shaped differently from other cells of the stent. The side branch structure comprises a serpentine ring that extends around the inner side branch cell. The serpentine ring comprises alternating struts and turns. The turns comprise alternating inner turns and outer turns, and the inner turns comprise alternating first inner turns and second inner turns. The second inner turns are located farther away from a side branch center point than the first inner turns.

In at least one other embodiment, a stent comprises a plurality of interconnected framework members defining a plurality of cells. A portion of the interconnected framework members comprise a side branch structure defining an inner side branch cell that is shaped differently from other cells of the stent. The side branch structure comprises a serpentine ring that extends around the inner side branch cell. The serpentine ring comprises alternating struts and turns. The struts comprise longer struts and shorter struts, and the serpentine ring comprises a repeating pattern of two adjacent longer struts and two adjacent shorter struts.

In at least one other embodiment, a stent comprises a plurality of interconnected framework members defining a plurality of cells. A portion of the interconnected framework members comprise a side branch structure defining an inner side branch cell that is shaped differently from other cells of the stent. The side branch structure comprises a serpentine ring extending around the inner side branch cell and a plurality of connectors. Each connector is connected at one end to the serpentine ring and connected at the other end to another part of the stent. The serpentine ring comprises alternating struts and turns, wherein the first two struts of the serpentine ring located on one side of a connector are parallel to the connector.

These and other embodiments which characterize the invention are pointed out with particularity in the claims annexed hereto and forming a part hereof. However, for a better understanding of the invention, its advantages and objectives obtained by its use, reference can be made to the drawings which form a further part hereof and the accompanying descriptive matter, in which there are illustrated and described various embodiments of the invention.

BRIEF DESCRIPTION OF THE DRAWINGS

A detailed description of the invention is hereafter described with specific reference being made to the drawings.

DETAILED DESCRIPTION OF THE INVENTION

Figure 1:
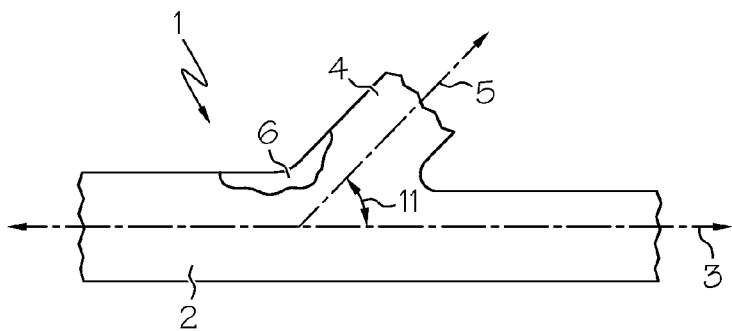
FIG. 1 is an illustration of a blood vessel bifurcation having an obstruction.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

The entire disclosures of U.S. Pat. Nos. 5,922,021, 6,123,721, 6,334,870, 6,478,816, 6,348,065, 6,325,826, and U.S. 2002-0095208are hereby incorporated herein by reference in their entireties. The entire disclosures disclosure of U.S. patent application Ser. Nos. 11/262,692, 60/844,011, and 11/519,552 are hereby incorporated herein by reference in their entireties. The entire disclosures of U.S. patent application Ser. Nos. 11/604,613, 11/848,171, 11/653,589 and 11/706,082 are hereby incorporated herein by reference in their entireties.

For the purposes of this disclosure, like reference numerals in the figures shall refer to like features unless otherwise indicated.

The present invention relates to stents for placement at vessel bifurcations and are generally configured to at least partially cover a portion of a branch vessel as well as a main vessel Referring to FIG. 1, an exemplary blood vessel bifurcation 1 is shown, having a main vessel 2 extending along a main vessel axis 3 and a branch vessel 4 extending along a branch vessel axis 5. Main vessel 2 and branch vessel 4 are disposed at an angle 11 of less than 90 degrees. An obstruction 6 is located within bifurcation 1, spanning or at least partially obstructing main vessel 2 and a proximal portion branch vessel 4.

Figure 2:
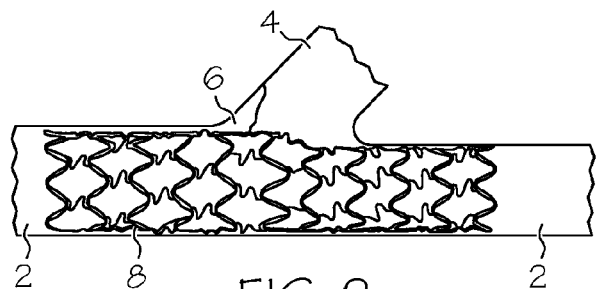
FIGS. 2-4 are illustrations of prior art stents implemented at a blood vessel bifurcation.
Figure 3:
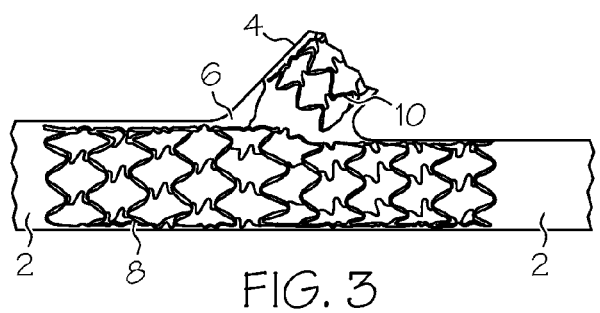
Figure 4:
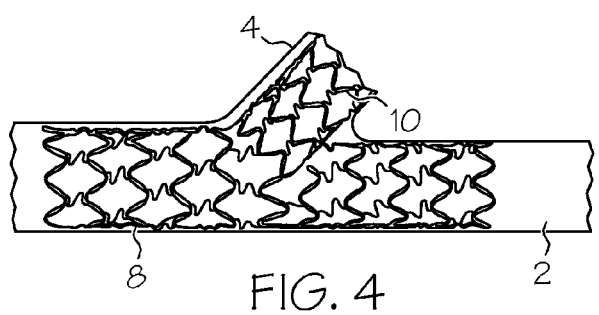

Prior attempts at relieving main vessel 2 and branch vessel 4 from obstruction 6, such as the one depicted in FIG. 1, have been problematic. Referring to FIGS. 2-4, examples of prior methods and structures for stenting an obstructed bifurcation are shown. As shown in FIG. 2, a first stent 8 is introduced into main vessel 2 and an access hole or side opening in the wall of stent 8 is usually created with a balloon to provide access to branch vessel 4 and unobstructed blood flow thereto. Typically, the access hole is created by deforming the struts and connectors of the main stent pattern, which may also deform the area of the stent surrounding the created opening and lead to undesirable results. Also, if stent 8 is used alone, at least a portion of obstruction 6 located within branch vessel 4 is left without stent coverage. Referring to FIGS. 3 and 4, one prior solution has been to introduce a second stent 10 into branch vessel 4, for example via a second catheter inserted through a side opening of first stent 8. As can be seen in FIGS. 3 and 4, such a configuration may introduce additional problems. For example, as shown in FIG. 3, second stent 10 may not provide full coverage of the portion of obstruction 6 in branch vessel 4 due to the angle 11 of the side branch vessel 4 with respect to main vessel 2 and the fact that the ends of the stent typically define a right angle to the longitudinal axis of the lumen. Alternatively, second stent 10 may extend beyond the bifurcation into main vessel 2, as shown in FIG. 4, and cause potential obstruction of blood flow in main vessel 2 and/or cause problems at the overlapping portions of stents 8 and 10.

Figure 5:
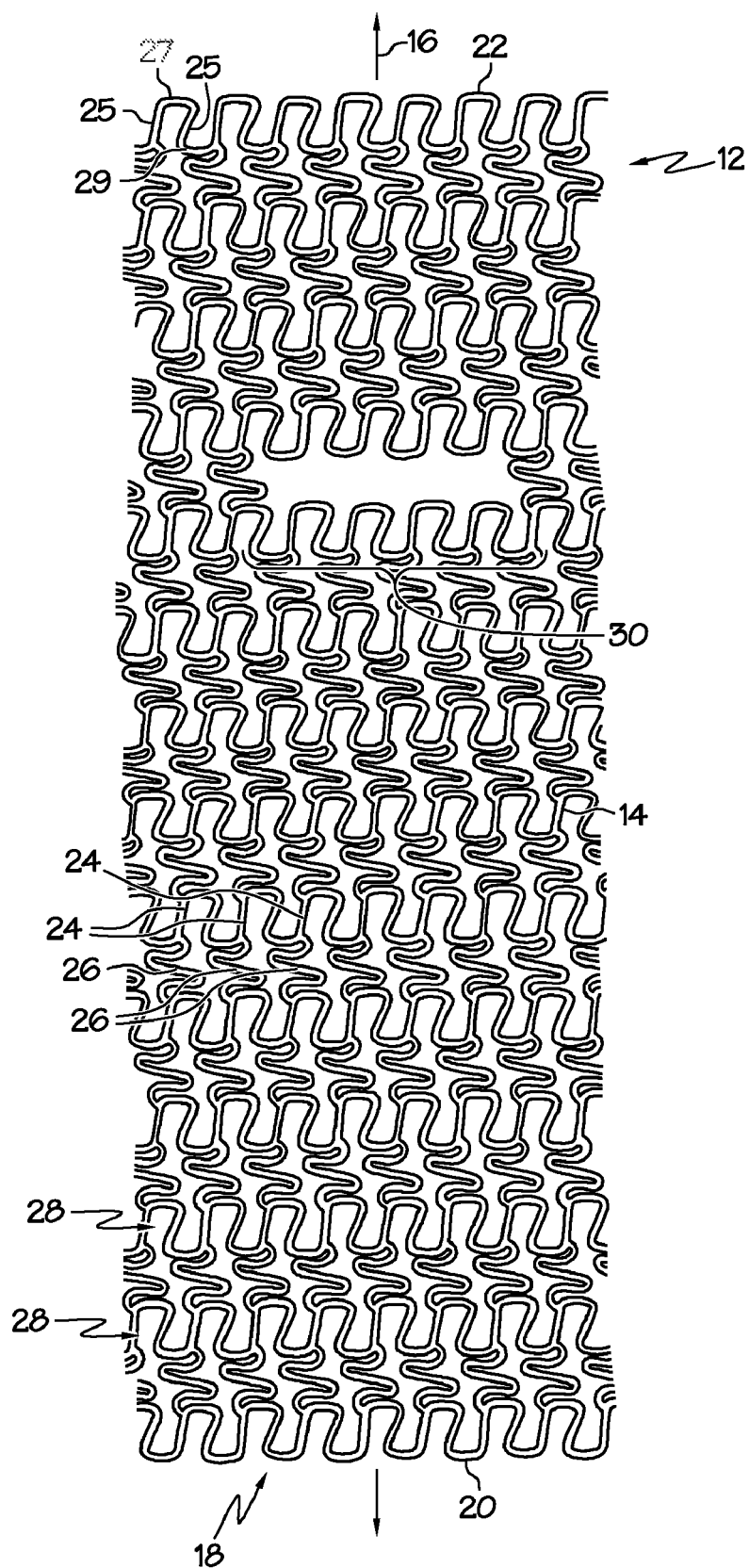
FIG. 5 is a flat view of an embodiment of an unexpanded stent in accordance with the present invention.
Figure 6:
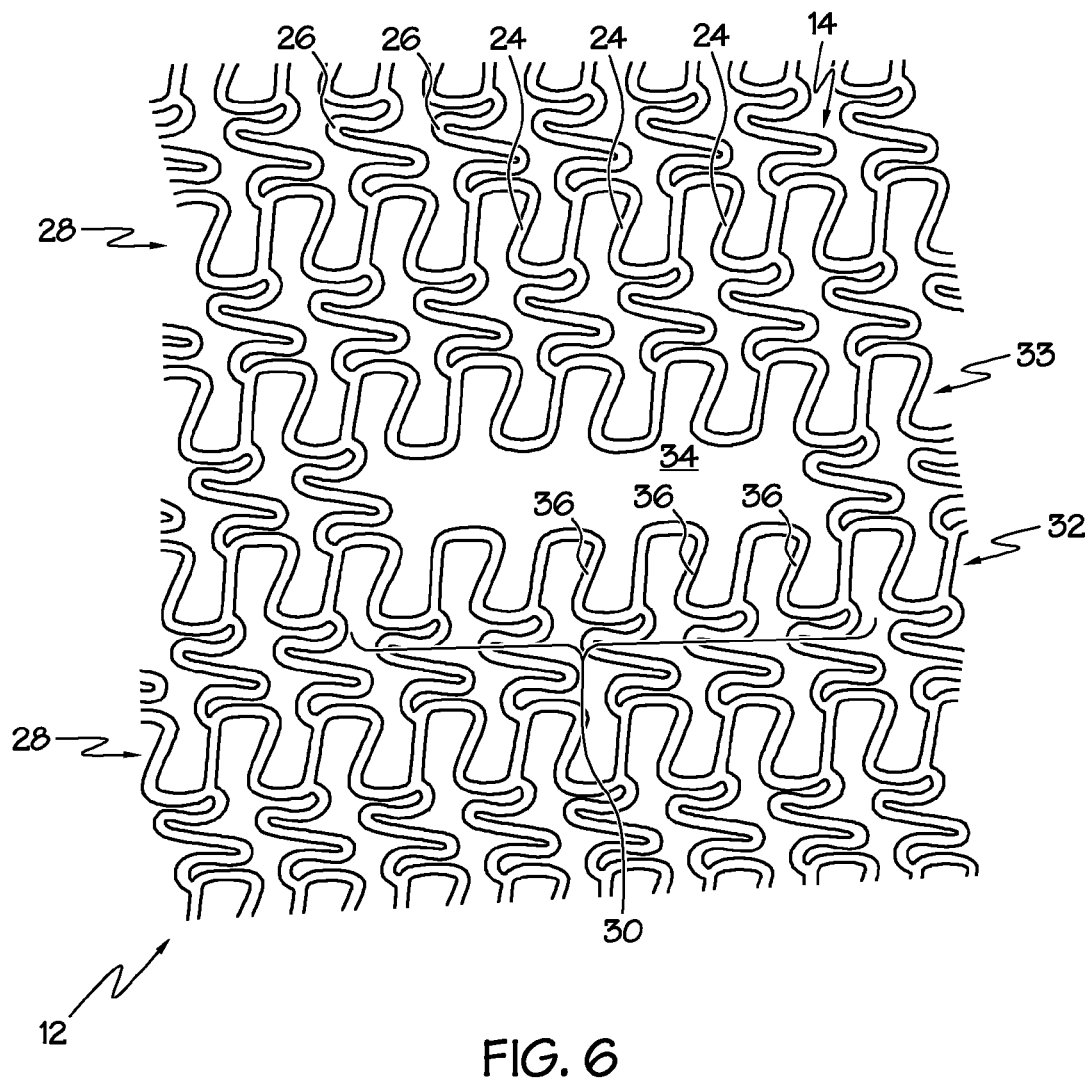
FIG. 6 is an enlarged view of a portion of the unexpanded stent shown in FIG. 5.
Figure 7:
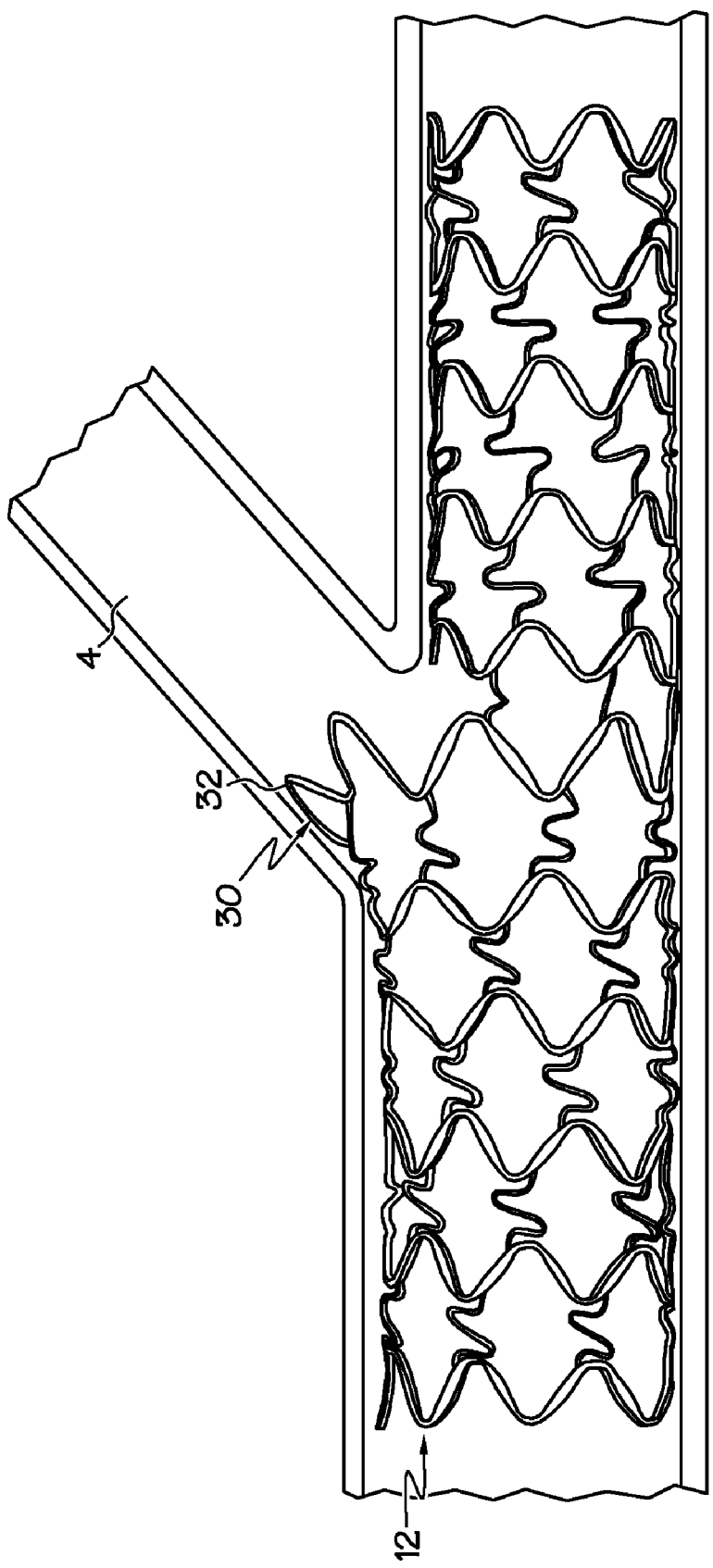
FIG. 7 is a perspective view of the expandable branch portion of the stent of FIG. 5 in the expanded configuration.

Referring now to FIGS. 5-7, a stent 12 according to one embodiment of the present invention comprises stent body or wall 14 extending along a longitudinal axis 16 from a proximal end 20 to a distal end 22 and defining a lumen 18 therein. Stent 12 may have a three-dimensional geometrical configuration having variable dimensions (length, width, height, depth, thickness, etc.). In a preferred embodiment, stent body 14 is a generally tubular structure. As defined herein, "tubular" can include an elongate structure that has varied cross-sections and does not require that the cross-section be circular. For example, the cross-section of stent wall 14 may be generally oval. In an alternate embodiment, stent body 14 is generally cylindrical. Also, the stent body 14 may have varied cross-sectional shapes along the longitudinal axis 16 of the stent. For example, the circumferences in the proximal and distal parts of the stent may be different. This may occur, for example, if during stent delivery the delivery system causes the stent to distend. Lumen 18 represents the inner volumetric space bounded by stent body 14. In a preferred embodiment, stent 12 is radially expandable from an unexpanded state to an expanded state to allow the stent to expand radially and support the main vessel. In the unexpanded state, stent body 14 defines a lumen 18 having a first volume, and in the expanded state, stent body 14 defines a lumen 18 having a second volume larger than the first volume.

FIG. 5 shows stent 12 in an unexpanded state in a flattened elevational view. As shown in FIG. 5, stent body 14 has a generally cellular configuration and comprises a generally repeatable series of struts 24 and connectors 26 configured in a predetermined general, overall, or main pattern along the length of stent 12. Struts 24 comprise a pair of longitudinal strut portions 25 joined by a curved portion 27 at the proximal ends. Struts 24 are interconnected by curved portion 29 at the distal ends and formed into rings 28 that extend about the circumference of stent 12. A series of the circumferential rings 28 are spaced apart from one another longitudinally along the entire length of stent 12, and connectors 26 connect rings 28 to each other longitudinally. Connectors 26 extend generally longitudinally between adjacent circumferential rings 28 and connect to the respective curved portions 25, 29 of longitudinally adjacent struts 24 of adjacent rings 28. In a preferred embodiment, connectors 26 are generally S-shaped or zigzag-shaped, although other patterns may also be used. Details of patterns that may be used for stent 12 are described more filly in co-pending PCT application IL02/00840, filed Oct. 20, 2002, incorporated herein by reference in its entirety. Furthermore, many other strut and connector patterns may be used, and the present pattern is shown for illustration purposes only.

Stent 12 further includes a branch portion 30 located at some point along the length of stent 12. Branch portion 30 comprises a section or portion of stent wall 14 that is configured to extend into a branch vessel in a vessel bifurcation In general, branch portion 30 is configured to be movable from an unextended position to an extended position. In the unextended position, branch portion 30 is disposed in the volume defined by the unexpanded stent 12, that is, the branch portion 30 does not protrude radially from stent wall 14. In the extended position, the branch portion 30 extends outwardly from stent wall 14 and branch portion 30 is extended into the branch vessel. As best seen in FIG. 6, branch portion 30 comprises a stent wall section of stent body 14 that is initially flush, coplanar, or cocylindrical with the remainder of stent body 14 and may extend outwardly with respect to the remainder of stent body 14. In this regard, branch portion 30 is generally adjacent an opening, slit, space, void, or other incongruity in the overall or main pattern of stent body 14. This configuration allows for access into a branch vessel, and at the same time allows for circumferential alignment of the stent within the vessel prior to deployment. In other embodiments, multiple branch portions can be incorporated into the stent to permit multiple access to one or more vessels. In a preferred embodiment, branch portion 30 may be positioned in the midsection of stent 12. In alternate embodiments, branch portion 30 may be positioned anywhere along the length of stent 12.

As best seen in FIG. 6, in a first embodiment, branch portion 30 comprises a portion of branch ring 32 and is positioned adjacent and proximal to an opening 34. Upon extension of branch portion 30, the portion of branch ring 32 adjacent opening 34 extends into the branch vessel, whereas the circumferential ring 28 adjacent branch ring 32 does not extend into the branch vessel. Opening 34 is formed by an absence of at least one connector 26 adjoining branch ring 32 with a branch opposing ring 33. In some embodiments, four adjacent connectors are absent; however, in alternate embodiments any number of connectors may be absent to create opening 34. In this embodiment, branch ring 32 is substantially similar geometrically to circumferential rings 28 and comprises branch ring struts 36 substantially similar to struts 24; however, a plurality of adjacent struts are free from connectors 26 adjacent opening 34. In this regard, branch ring 32 is at least partially detachable from stent body 14 to facilitate at least a portion of branch ring 32 to extend outwardly with respect to stent body 14. In some embodiments, the geometry of branch ring 32 may vary with respect to circumferential rings 28, and branch ring struts 36 may have different configurations than struts 24.

When stent 12 is expanded, as shown in FIG. 7, branch portion 30 is extended into the branch vessel, causing a portion of branch ring 32 to at least partially cover the inner surface of the branch vessel 4. Thus, in a preferred embodiment, the stent coverage in the branch vessel includes at least partial coverage of the proximal side of the inner branch vessel wall.

Various alternative embodiments provide varying geometries of branch portion 30. For example, branch ring 32 may vary with respect to circumferential rings 28, and branch ring struts 36 may have different configurations than struts 24. In one alternate embodiment, branch ring struts 36 are longer than struts 24. In another embodiment, branch ring struts 36 are more closely packed circumferentially, resulting in a greater number of branch ring struts 36 per area within branch ring 32 as compared to circumferential rings 28. In another embodiment, branch ring struts 36 may be thinner than struts 24. In yet another embodiment, branch ring struts 36 may be made of a different material than struts 24.

Figure 8:
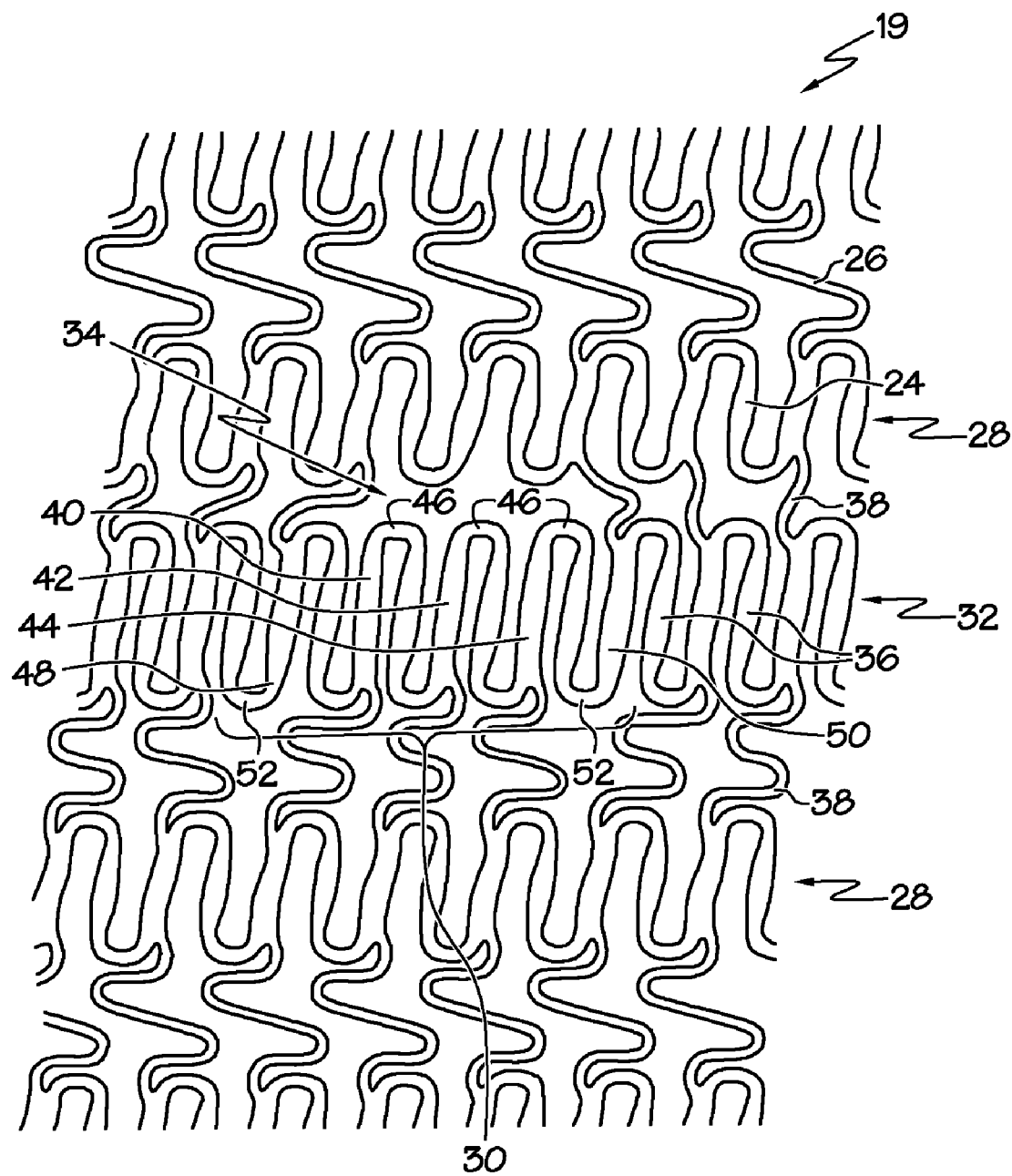
FIG. 8 is an enlarged view of a portion of another embodiment of a stent according to the present invention.

Referring to FIG. 8, another alternate embodiment of stent 19 is shown wherein a branch portion 30 comprises a branch ring 32 having branch ring struts 36 that are longer than struts 24 and a greater number of branch ring struts 36 provided as compared to the number of struts 24 in circumferential rings 28, resulting in a more closely packed branch ring 32. Furthermore, the number of branch ring connectors 38 on both sides of branch ring 32 is lower per branch strut 36 than the number of connectors 26 per strut 24. Opening 34 is adjacent branch ring 32 on a distal side thereof, and the distal ends 46 of at least one, and preferably a plurality, of branch ring struts 40, 42, 44 are free from connectors and detachable from stent body 14. In this embodiment, two branch ring struts 48 and 50 positioned laterally adjacent struts 40, 42, and 44 have proximal ends 52 free from connectors. In this regard, free proximal ends 52 provide less resistance to movement of branch ring 32 during outward expansion with respect to stent body 14. This same procedure can be used to provide one, two, three or more proximal ends in the ring free of connectors. Additionally, the shape and configuration of branch ring connectors 38 is different than those of connectors 26. For example branch ring connectors along the proximal side of branch ring 32 are longer than connectors 26 to facilitate greater expansion of branch portion 30 into a vessel side branch. Also, branch ring connectors along the distal side of branch ring 32 are shaped and oriented differently than connectors 26 to facilitate greater expansion of branch portion 30 into the branch vessel. In alternate embodiments, branch ring connectors 38 may also differ among themselves. Also, the longer branch ring struts 36 are generally more flexible than comparable shorter struts because the added length permits more deflection. Also, the added length permits greater coverage vessel wall coverage due to deeper penetration into the branch vessel during extension. In alternate embodiments, different geometries and orientations of branch ring connectors 38 may be used.

Figure 9:
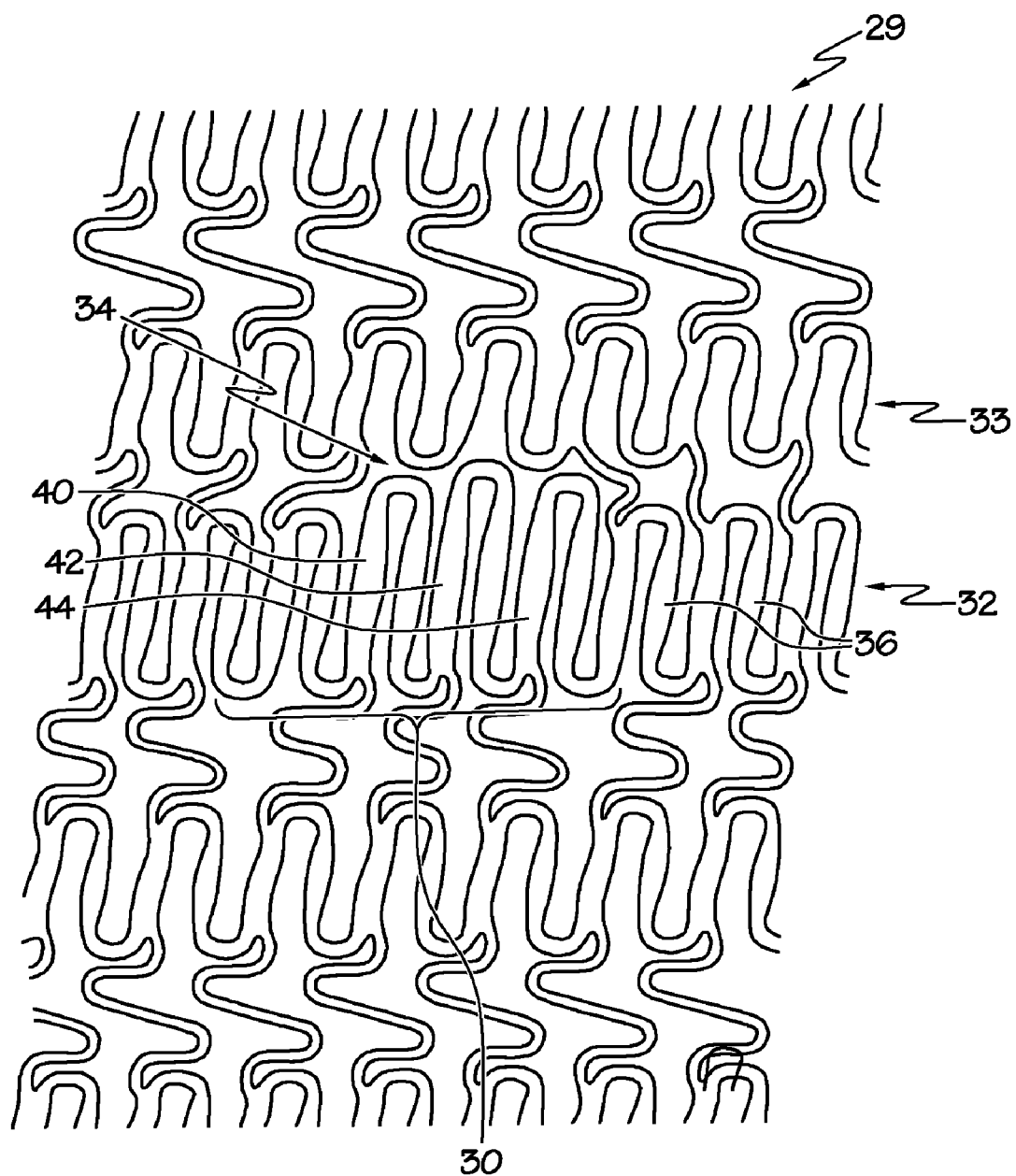
FIG. 9 is an enlarged view of a portion of an alternative embodiment of a stent according to the present invention.

Referring to FIG. 9, another alternate embodiment of stent 29 is shown having a branch portion 30 similar to that of the embodiment of FIG. 8, except branch ring struts 40, 42, and 44 are longer than the other branch ring struts 36, and the distal ends thereof define an arcuate profile to the proximal side of opening 34. Also, central strut 42 is longer than struts 40, 44 adjacent to strut 42. In this regard, when branch portion 30 is extended, struts 40, 42, and 44 extend further into the branch vessel and provide more coverage of the vessel wall than the embodiment depicted in FIG. 8. In this regard, this embodiment may more readily cover an obstruction in a bifurcation vessel such as the one depicted in FIG. 1 and, therefore, may provide better blood flow to a branch vessel. Furthermore, as described in more detail below, this embodiment facilitates the use of a second stent in the branch vessel.

Figure 10:
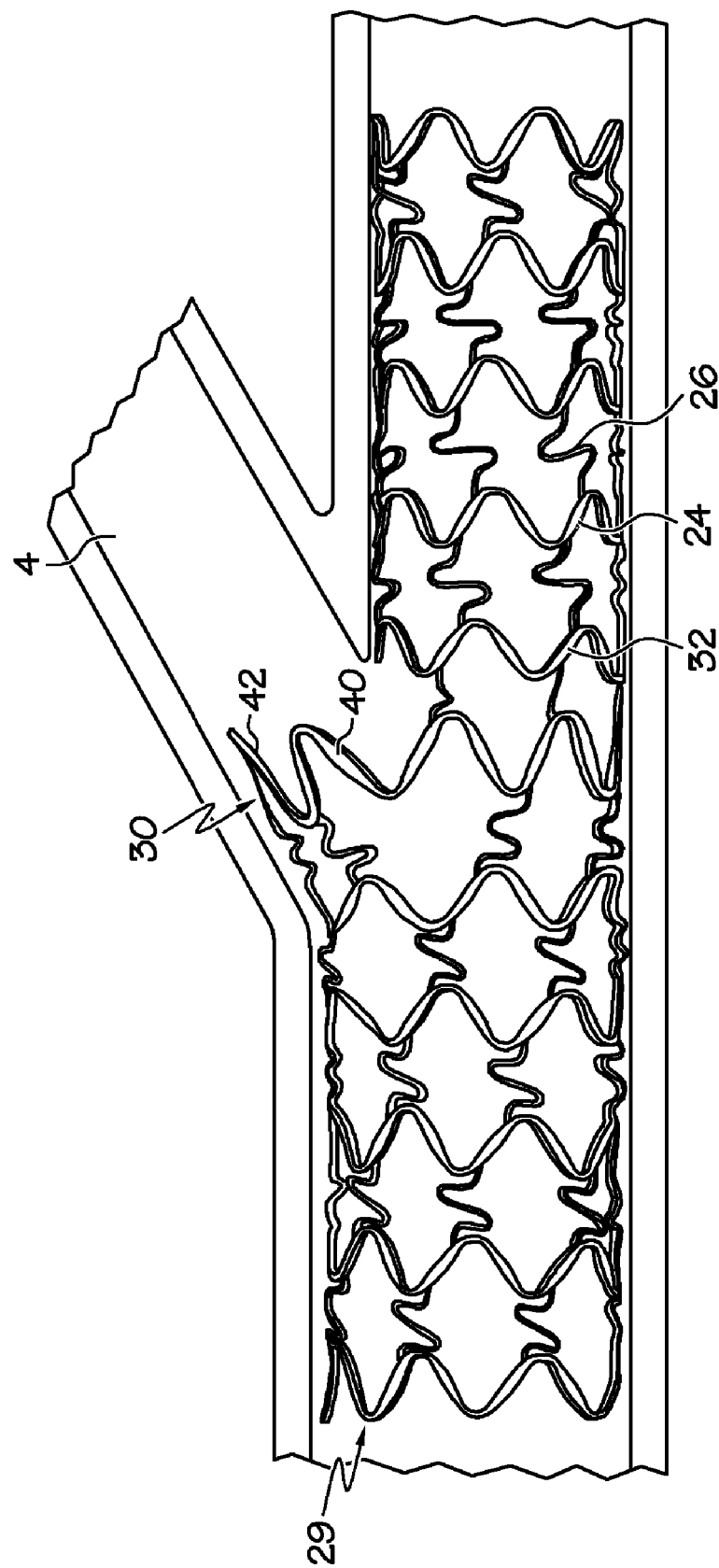
FIG. 10 is a perspective view of the expandable branch portion of the stent of FIG. 9 in the expanded configuration.

Referring to FIG. 10, stent 29 of FIG. 9 is shown in an expanded state with branch portion 30 extended into the branch vessel, causing branch ring 32 to at least partially cover the inner surface of the branch vessel on the proximal side. The distal end of strut 42 of branch ring 32 extends further into the branch vessel than the distal ends of struts 40, 44 because strut 42 is longer in this embodiment than adjacent struts 40, 44. In this regard, a generally tapered, straight or linear profile along the distal perimeter of branch portion 30 is created when branch portion 30 is expanded into the branch vessel.

Figure 11:
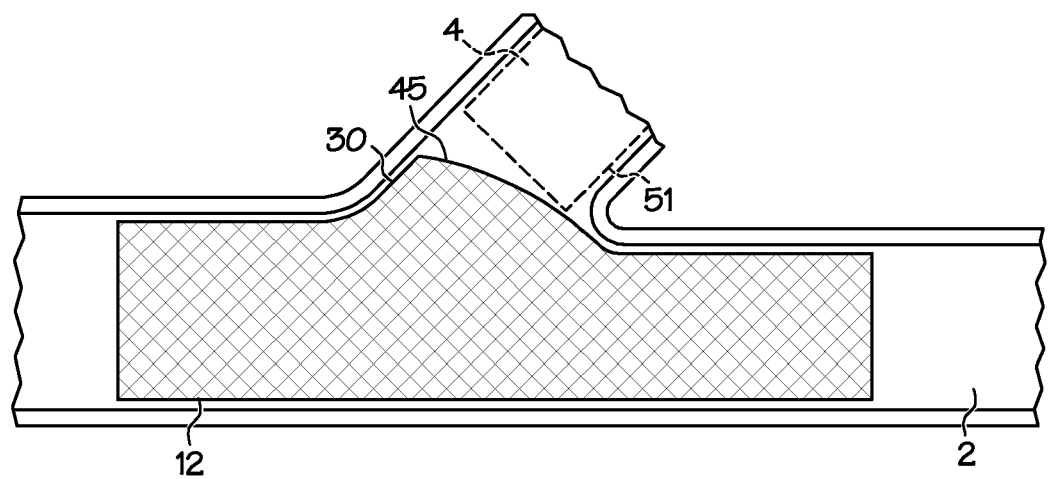
FIG. 11 is a schematic view of the stent of FIG. 5 in the expanded state implemented at a blood vessel bifurcation.
Figure 12:
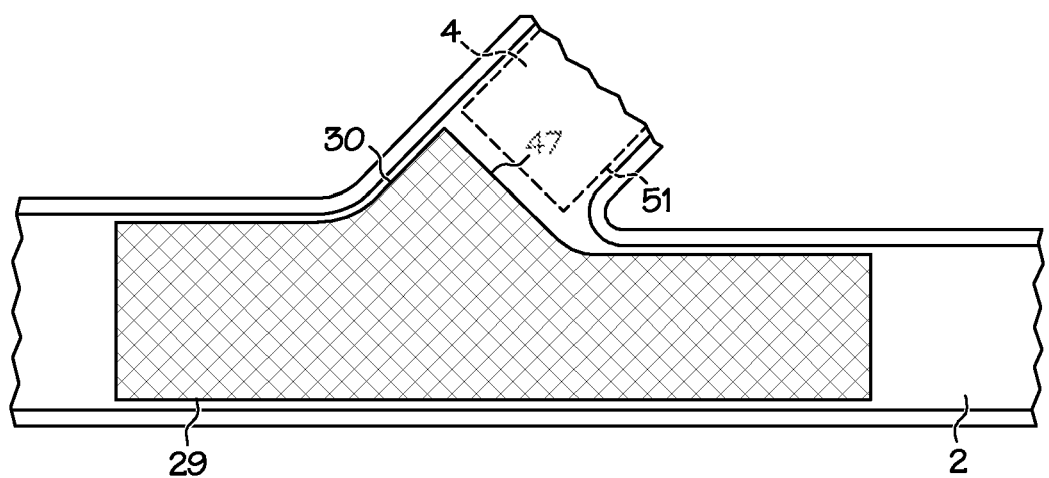
FIG. 12 is a schematic view of the stent of FIG. 9 in the expanded state implemented at a blood vessel bifurcation.

Referring to FIGS. 11 and 12, schematic views are shown of stents 12, 29 of FIGS. 5 and 9, respectively, in the expanded state as implemented at a blood vessel bifurcation. As shown in FIG. 11, stent 19 of the embodiment of FIG. 8 has a generally curved or radial profile along the distal perimeter 45 of branch portion 30 as it extends into branch vessel 4. The generally curved or radial profile is due to the particular geometry of branch portion 30 of stent 19 of the embodiment of FIG. 8. In particular, because all of the branch ring struts 36 of branch ring 32 are of equal length in this embodiment, the distal ends of struts 36 radially expand equidistantly into branch vessel 4, thereby creating a generally curved or radial profile along the distal perimeter 45 of branch portion 30. Referring to FIG. 12, stent 29 of the embodiment of FIG. 9 has a generally tapered, straight or linear profile along the distal perimeter 47 of the branch portion 30 of the stent as it extends into branch vessel 4. The generally straight or linear profile in FIG. 12 is a result of the particular geometry of branch portion 30 of stent 29 of the embodiment of FIG. 9. In particular, because central strut 42 of branch ring 32 is longer in this embodiment than struts 40, 44 adjacent to strut 42, the distal end of strut 42 extends further into branch vessel 4 than the distal ends of struts 40, 44, as best seen in FIG. 10, thus creating a generally tapered, straight or linear profile along the distal perimeter of branch portion 30. In a preferred embodiment, the linear profile is at a right angle with respect to the axis of branch vessel 4. In alternative embodiments, however, the linear profile may be at any angle with respect to the axis of branch vessel 4. One advantageous feature of the linear profile along the distal perimeter of branch portion 30 shown in FIG. 12 is that if a second stent 51 were to be used in branch vessel 4, the linear profile facilitates better alignment with the second stent and permits coverage of a larger surface area of the branch vessel wall. For example, if a second stent 51 were to be used in combination with stent 12 of FIG. 11, gaps may exist between the two stents at the interface between the radial distal perimeter 45 and an abutting straight or linear edge of a second stent, whereas a close abutting interface may be achieved with stent 29 of FIG. 12.

Figure 13:
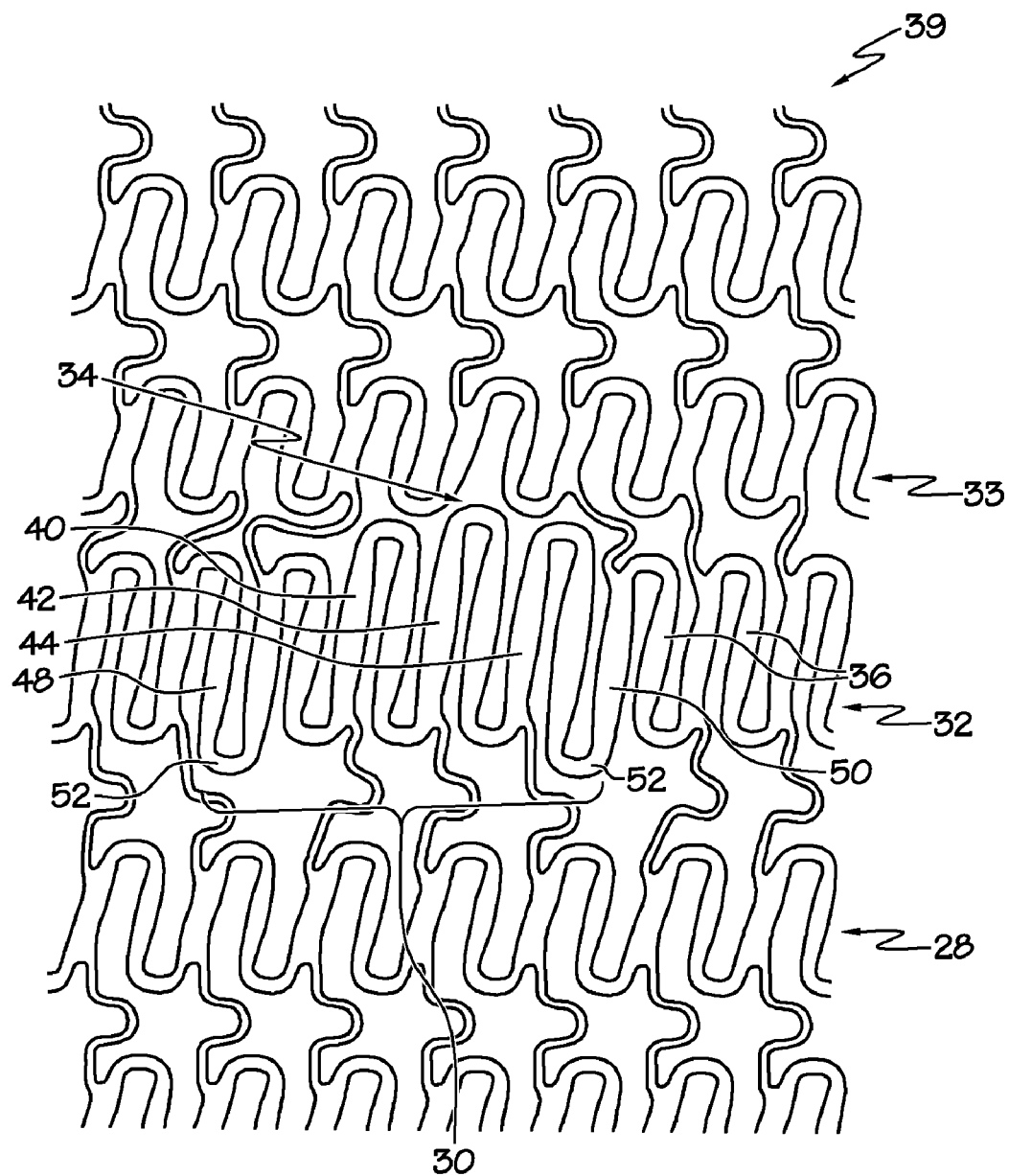
FIG. 13 is an enlarged view of a portion of another embodiment of a stent according to the present invention.

Referring to FIG. 13, another embodiment of stent 39 is shown having an alternative embodiment of a branch portion 30 similar to that of the embodiment of FIG. 9, except lateral branch ring struts 48 and 50 are longer than the other branch ring struts 36, and the proximal ends 52 of branch ring struts 48, 50 extend proximally beyond the other branch ring struts into a space between the branch ring 32 and the adjacent circumferential ring 28. Branch ring struts 48, 50 have proximal ends 52 free from connectors and provide less resistance to movement of branch ring 32 during outward expansion with respect to stent body 14. In this regard, the longer lateral branch ring struts 48, 50 function similar to a hinge and further facilitate extension of branch ring portion 30 outwardly, which may accommodate a branch vessel disposed at a greater angle 11 (FIG. 1) as compared to stent 29 of the embodiment of FIG. 9. Again, since struts 40, 42, and 44 are longer than branch ring struts 36, they are more flexible and provide more coverage of a vessel wall than the embodiment depicted in FIG. 8.

Figure 14:
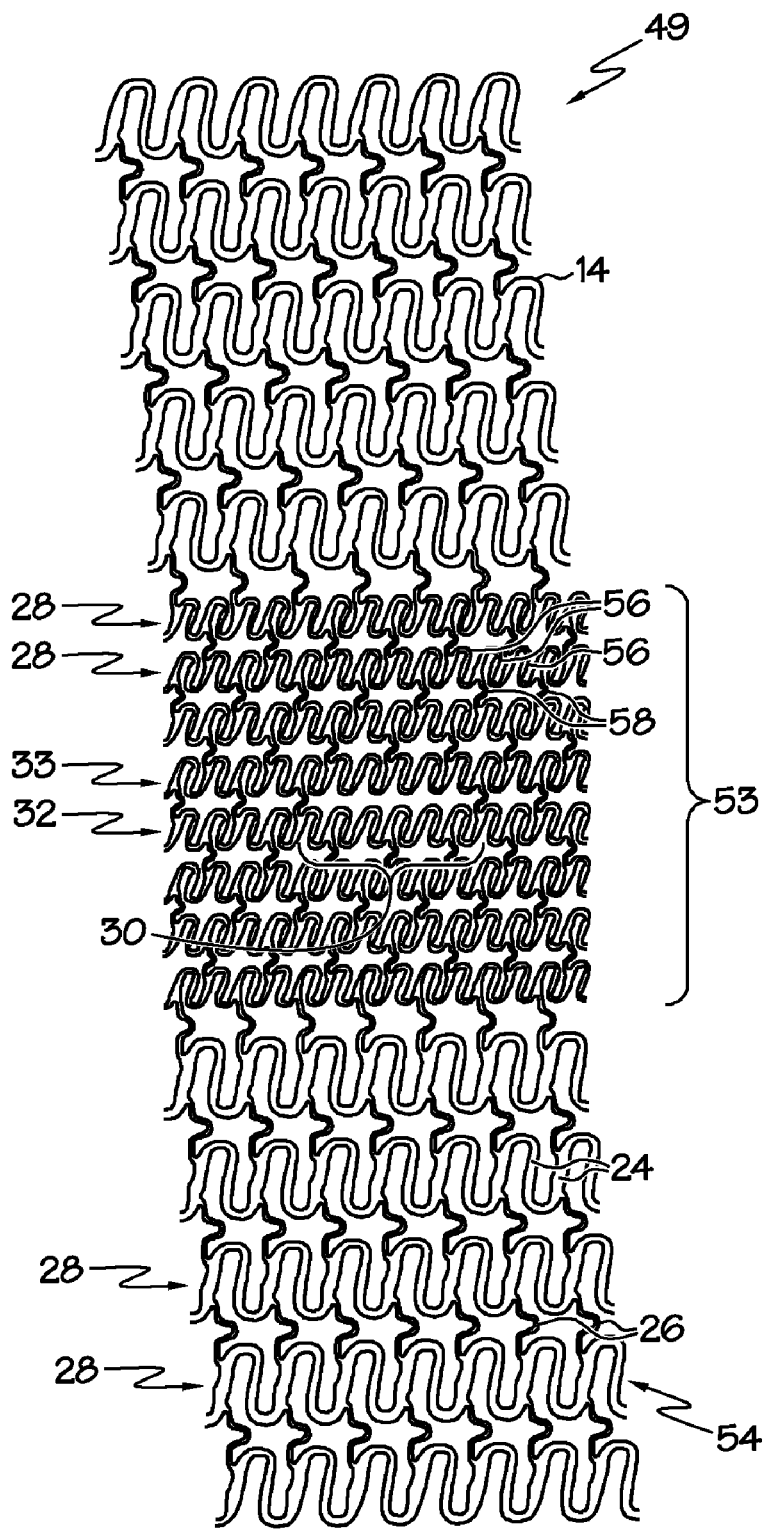
FIG. 14 is a flat view of another embodiment of an unexpanded stent in accordance with the present invention.
Figure 15:
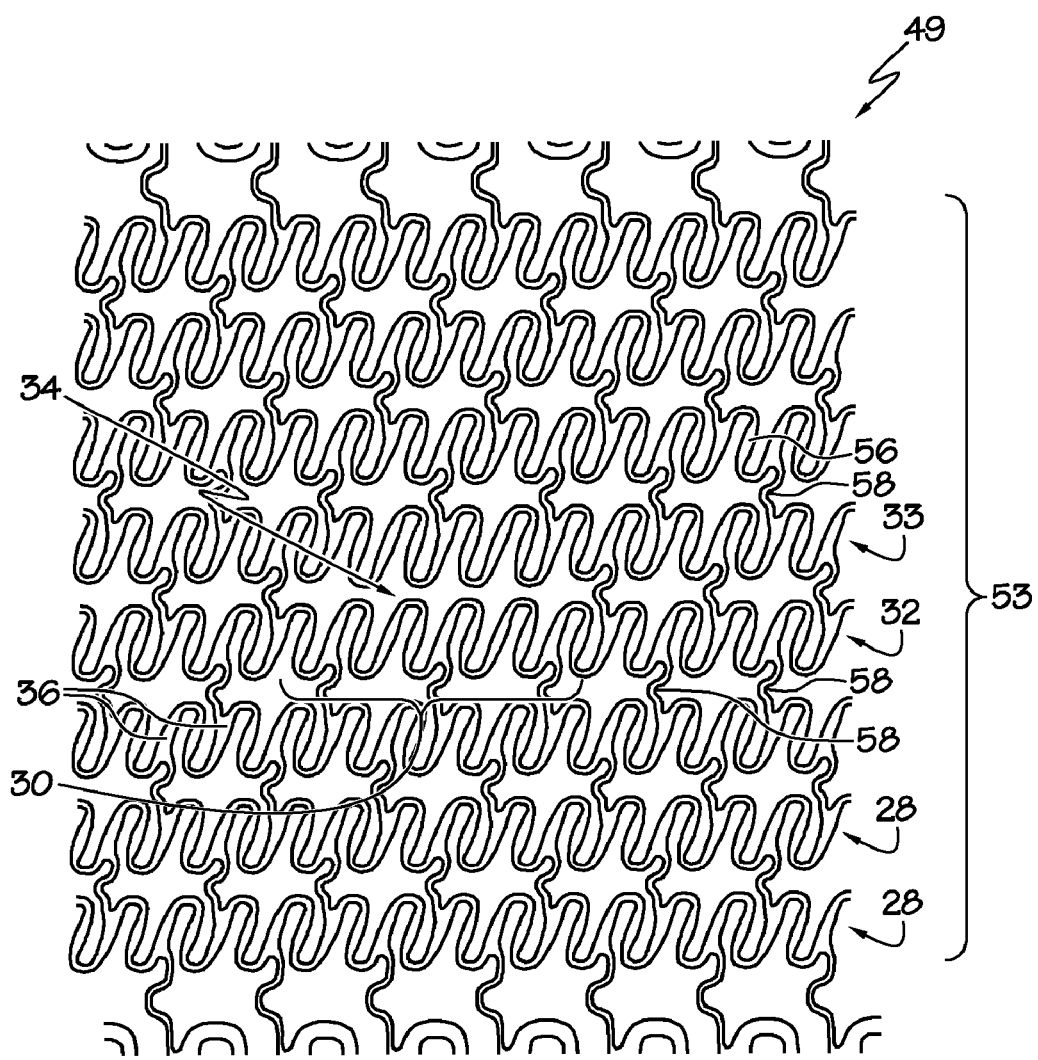
FIG. 15 is an enlarged view of a portion of the unexpanded stent shown in FIG. 14.

Referring now to FIGS. 14 and 15, another embodiment of stent 49 is shown having a stent body 14 that has a longitudinal section 53 that has a different pattern than main pattern 54. Longitudinal section 53 comprises a generally repeatable series of struts 56 and connectors 58 that are smaller in dimension than struts 24 and connectors 26, but are formed into a similar geometrical pattern as main pattern 54. In this regard, the struts 56 are more numerous per area within rings 28, and rings 28 are more numerous per area in section 53 because the length of struts 56 is shorter than the length of struts 24 and the length of connectors 58 is shorter than the length of connectors 26. In a preferred embodiment, the same number of connectors 58 extend between adjacent rings 28; however, because the struts are more numerous in longitudinal section 53, connectors 58 extend longitudinally between every other strut of adjacent rings 28. As shown in FIG. 15, stent 49 further includes a branch portion 30 positioned within section 53. Branch portion 30 comprises a branch ring 32 adjacent an opening 34. Opening 34 is formed by an absence of at least one connector 26 adjoining branch ring 32 with branch opposing ring 33. In a preferred embodiment, two adjacent connectors are absent; however, in alternate embodiments any number of connectors may be absent to create opening 34. In this embodiment, branch ring 32 is substantially similar geometrically to circumferential rings 28 and comprises branch ring struts 36 substantially similar to struts 56; however, a plurality of adjacent struts are free from a connector 58 adjacent opening 34 and branch ring 32 is at least partially detachable from stent body 14 at opening 34 to facilate at least a portion of branch ring 32 to extend outwardly with respect to stent body 14. The generally smaller struts and connectors of longitudinal section 53 provide for freer movement of the strut and connector material and facilitate conformance to a vessel wall. The smaller struts and connectors also provide for a relatively more dense surface area coverage of the branch vessel wall, which may be advantageous in achieving a more uniform coverage around the ostium. In particular, this embodiment may provide particularly advantageous coverage of a geometrically complex obstruction in a bifurcation vessel since the relatively small pattern may flex or contour around the obstruction and provide coverage therefor. Also, this embodiment is advantageous for relatively small obstructions as the smaller pattern may cover more surface area of obstruction.

Figure 16:
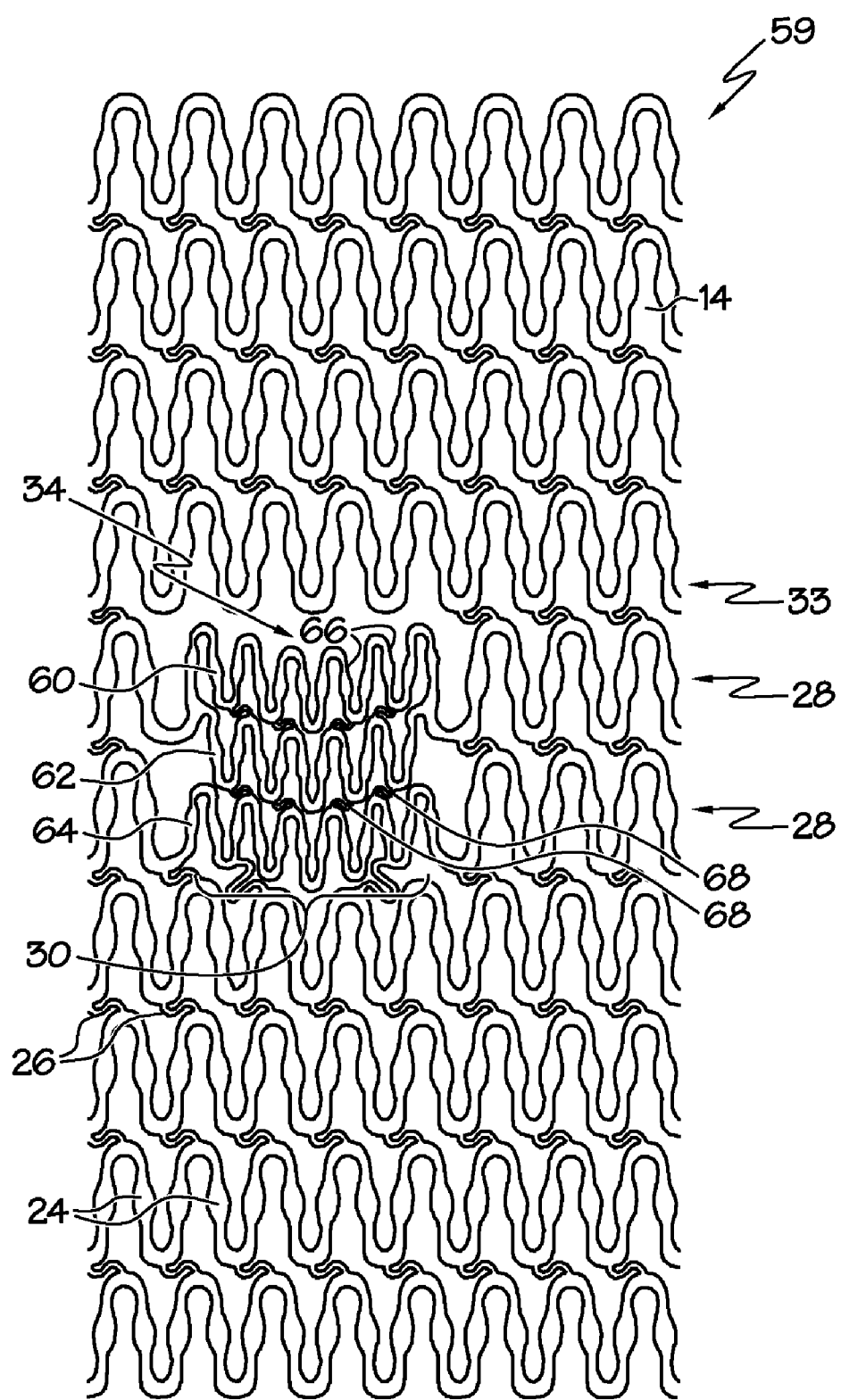
FIG. 16 is a view of a portion of another embodiment of a stent according to the present invention.

Referring to FIG. 16, another embodiment of stent 59 is shown and includes an alternate branch portion 30 comprising a portion of three adjacent branch ring sections 60, 62, 64 connected and extending circumferentially from two adjacent circumferential rings 28. Branch ring sections 60, 62, 64 each includes a plurality of branch struts 66 and are connected in the longitudinal direction by branch connectors 68. Struts 66 are shorter longitudinally than struts 24 of rings 28 and connectors 68 are smaller than connectors 26. The distal ring 60 is adjacent opening 34 and the distal ends of struts 66 of ring 60 are detachable from stent body 14 at opening 34 to permit extension of at least a portion of branch ring sections 60, 62, 64 to expand outwardly with respect to stent body 14. In this embodiment, the three branch ring sections 60, 62, 64 may extend outwardly in a more radial fashion and this branch portion 30 may be particularly advantageous for adapting or conforming to the shape of the proximal side of the ostium. Furthermore, the branch portion of this embodiment may more readily extend or flex around an obstruction in a bifurcation vessel such as the one depicted in FIG. 1 while providing branch wall coverage and better blood flow to the branch vessel.

Figure 17:
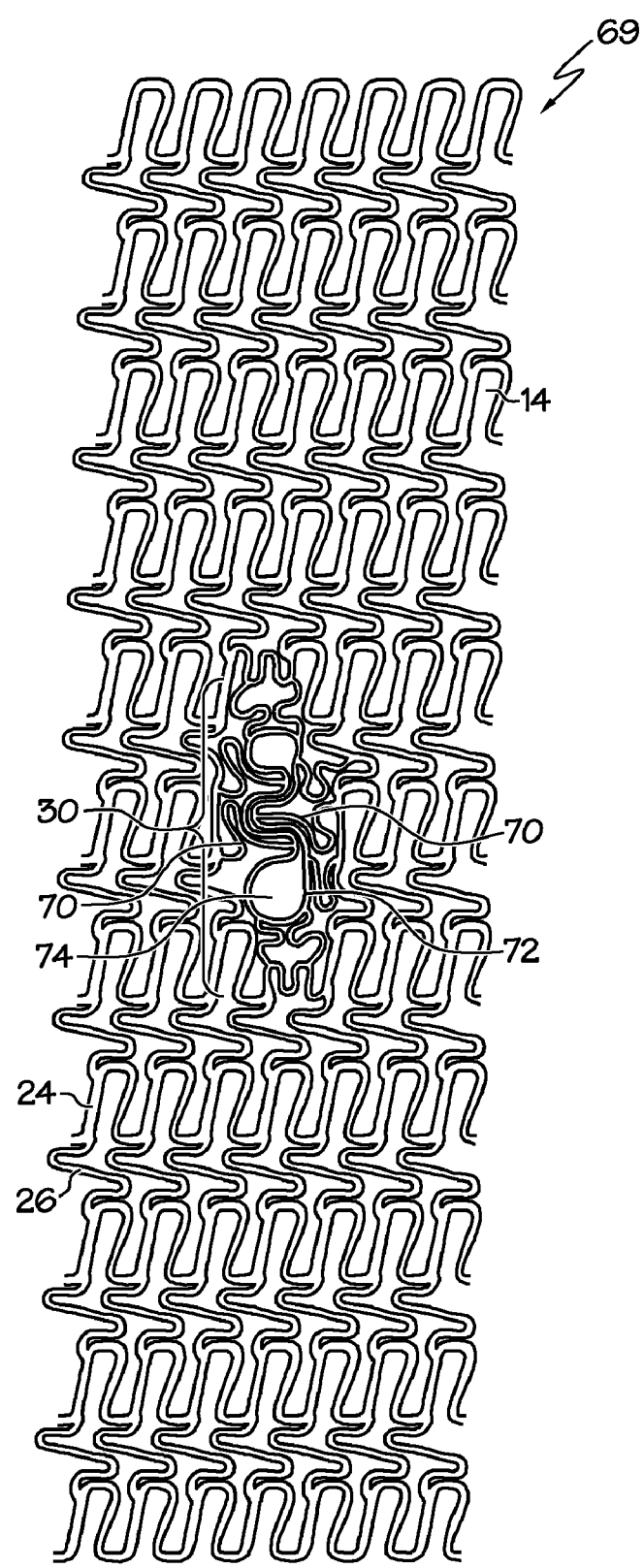
FIG. 17 is a flat view of another embodiment of an unexpanded stent in accordance with the present invention.
Figure 18:
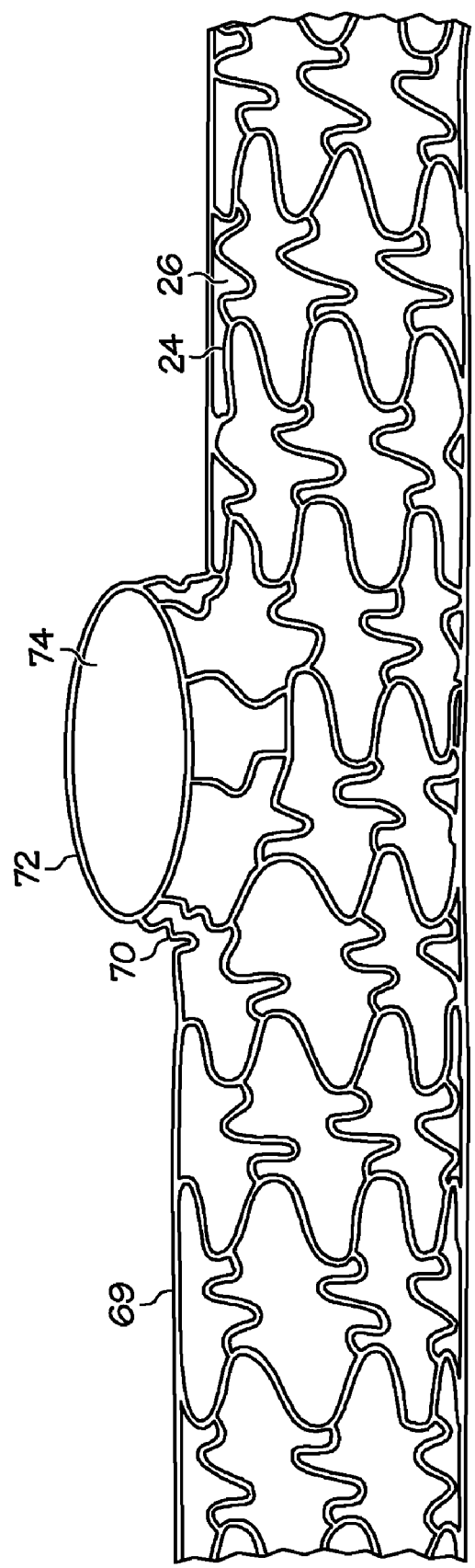
FIG. 18 is a perspective view of the expandable branch portion of the stent of FIG. 17 in the expanded configuration.

Referring to FIGS. 17 and 18, an alternate embodiment of stent 69 is shown and includes an alternate branch portion 30. In this particular embodiment, branch portion 30 comprises support struts 70 and an expandable ring 72. Branch portion 30 defines at least one side opening 74. In one embodiment, the dimensions of the cell defining side opening 74 are such that the side opening 74 (prior to expansion of the stent) is larger than other openings in stent body 14. The presence of side opening 74 is generally configured to accommodate a side sheath therethrough and allow a physician to access a branch vessel during or after a procedure. In a particular embodiment, as shown in FIG. 17, side opening 74 is surrounded by expandable ring 72 of continuous material. In alternative embodiments, expandable ring 72 comprises unattached portions, or one portion that only partially covers side opening 74. A series of support struts 70 connect expandable ring 72 with struts 24 and connectors 26. Support struts 70 preferably comprise patterns in a folded or wrap-around configuration that at least partially straighten out during expansion, allowing expandable ring 72 to protrude into the branch vessel.

In this embodiment, when stent 69 is expanded, as shown in FIG. 18, branch portion 30 is extended into the branch vessel, causing expandable ring 74 to at least partially cover the inner surface of the branch vessel. Thus, in a preferred embodiment, the stent coverage in a portion the branch vessel includes the fill circumference of the inner branch vessel wall. In alternative embodiments, partial coverage or several sections of coverage are present.

Figure 19:
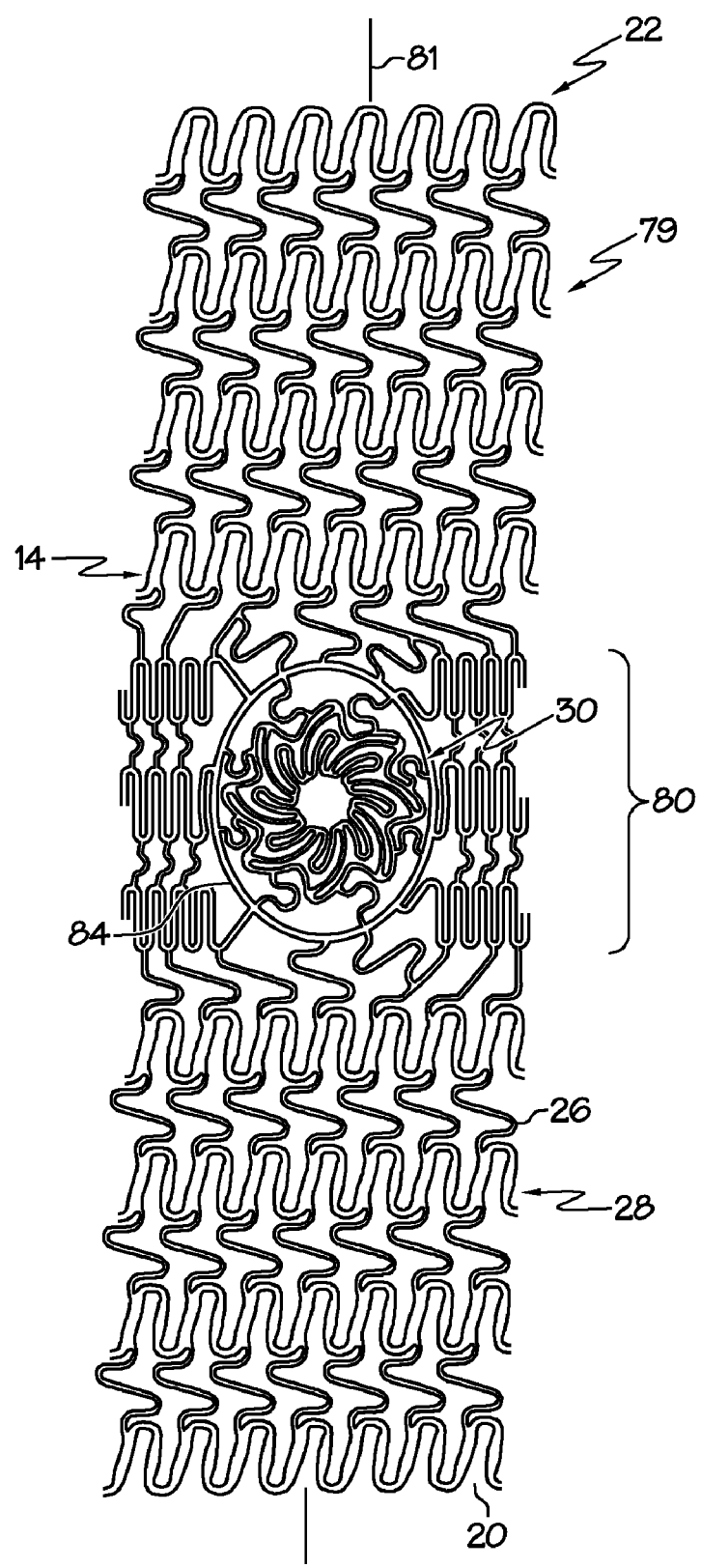
FIG. 19 is a flat view of another embodiment of an unexpanded stent in accordance with the present invention.
Figure 20:
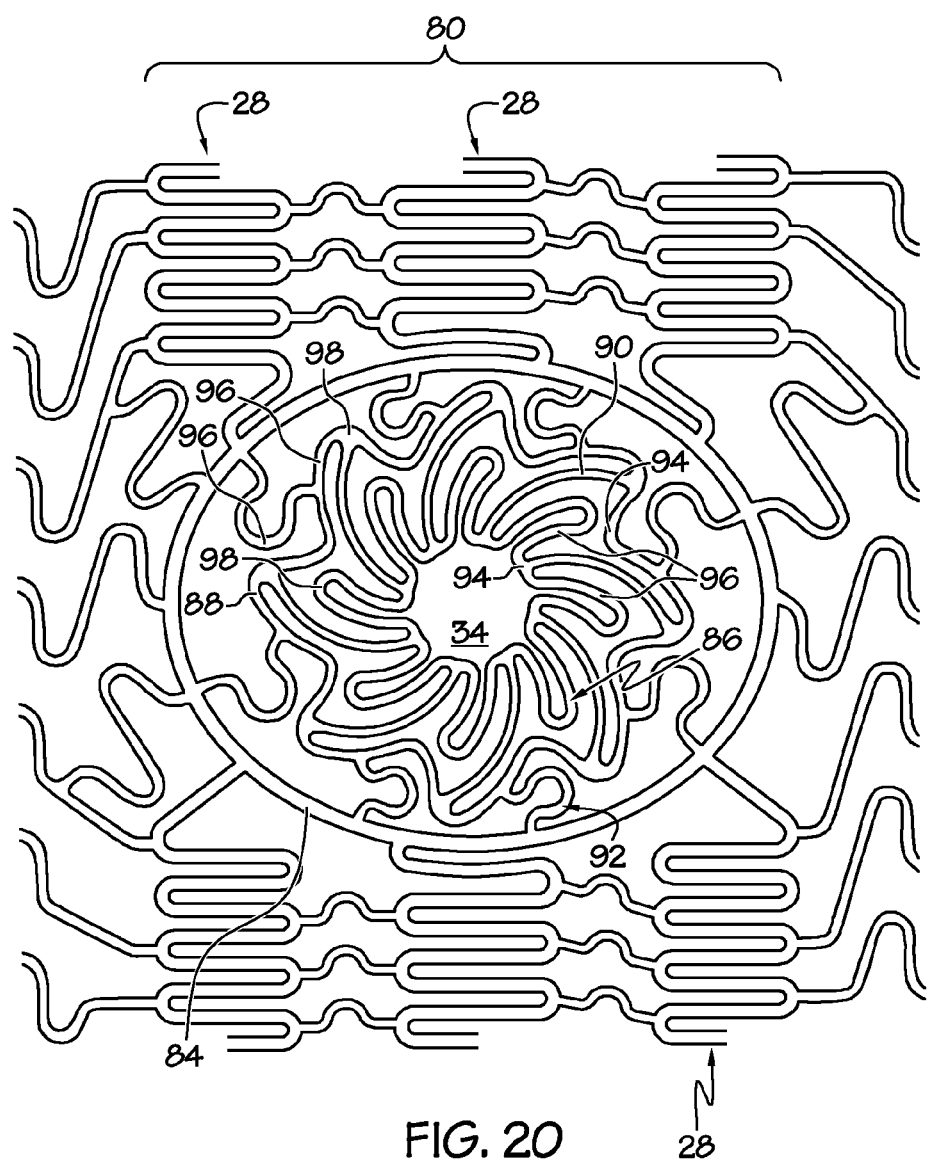
FIG. 20 is an enlarged view of a portion of the stent of FIG. 19.
Figure 21:
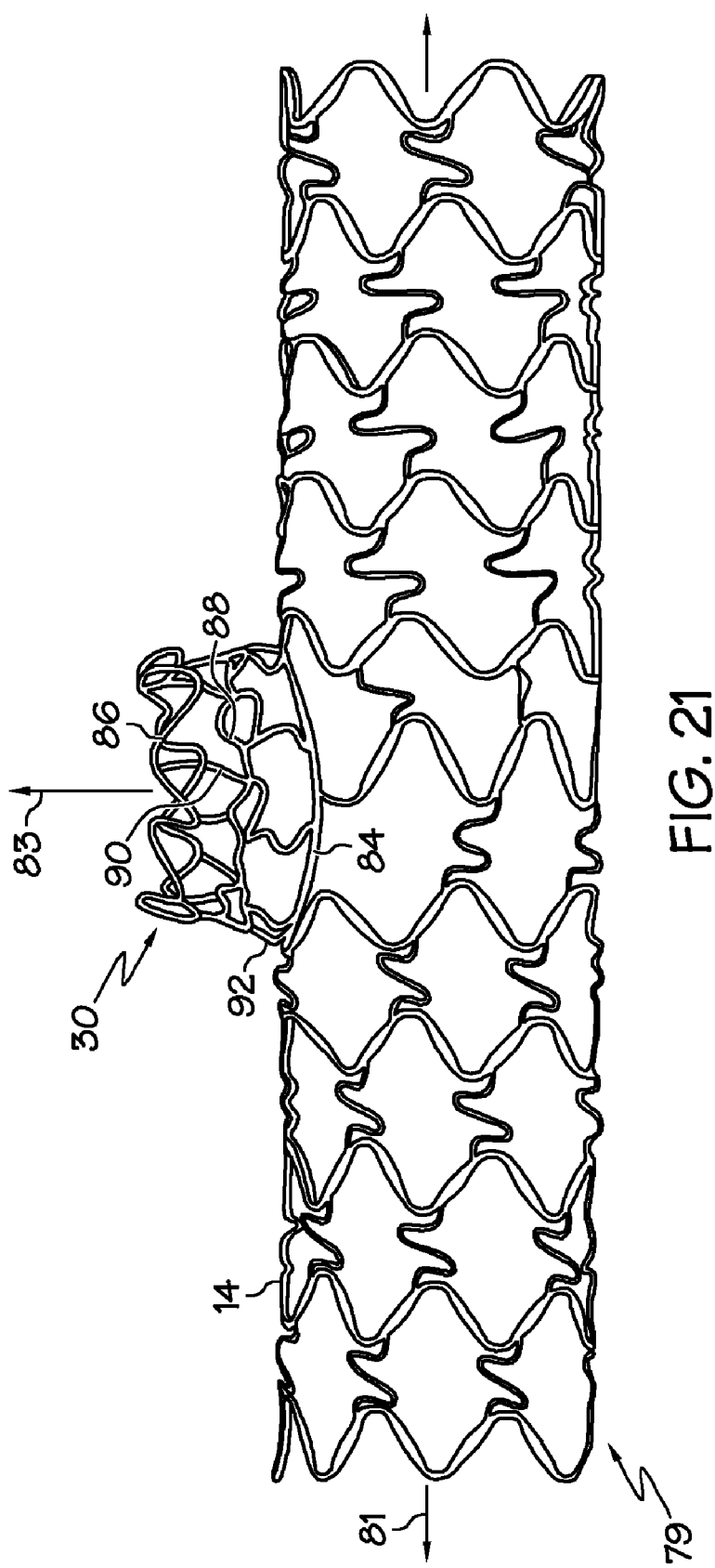
FIG. 21 is a view of the expandable branch portion of the stent of FIG. 19 in the expanded configuration.

Referring to FIGS. 19-21, another embodiment of a stent 79 is shown having a main stent body 14 and another embodiment of a branch portion 30. FIGS. 19 and 20 show stent 79 in the unexpanded condition where branch portion 30 has not been deployed. FIG. 21 shows the stent 79 in the expanded configuration where the branch portion 30 has been expanded. As shown, main stent body 14 includes a main stent pattern having a generally repeatable ring 28 and connector 26 pattern. Branch portion 30 and the surrounding midsection 80 interrupt the repeatable ring 28 and connector 26 pattern of stent 79. In this embodiment, branch portion 30 is configured to be both radially expandable and longitudinally extendable into the branch vessel and relative to its longitudinal axis 83 so that, in a preferred embodiment, the branch portion 30 contacts the entire periphery or circumference of the inner wall of the branch vessel in the expanded configuration. In this regard, branch portion 30 preferably provides 360.degree. coverage of the wall of the branch vessel That is, branch portion 30 can be extended outward with respect to longitudinal axis 81 of stent 79, and can also be expanded radially about axis 83 so as to contact the vessel (thereby allowing it to be adjustable with respect to vessel size).

Referring to FIG. 20, an enlarged view of section 80 of stent 79 is shown. In a preferred embodiment, a structural support member 84 may be provided as a transition between the main stent body 14 and branch portion 30. In one aspect of a preferred embodiment, structural support member 84 may be elliptical to accommodate branch vessels extending at an angle to the main vessel. In alternate embodiment, other shapes of support member 84 can be used to accommodate the vasculature. The structural support member 84 may include a continuous ring. In this embodiment, structural support member 84 is a fill, non-expandable ring and it does not expand radially beyond a particular circumference.

As shown in FIGS. 19 and 20, two concentric rings, inner ring 86 and outer ring 88, are positioned within structural support member 84 and surround a generally circular central branch opening 34 to provide access to the side branch vessel when stent 79 is in the unexpanded condition. Rings 86 and 88 are interconnected by a plurality of inner connectors 90. Outer ring 88 is connected to structural support member 84 by a plurality of outer connectors 92. Rings 86 and 88 are generally curvilinear members. For example, rings 86, 88 can be defined by undulation petals, prongs, or peaks 94. In a preferred embodiment, each ring 86, 88 have the same number of undulation peaks 94, but the inner ring may be more closely or tightly arranged, as shown. In another preferred embodiment, each ring 86, 88 has eight pedals or undulation peaks 94, although in alternate embodiments each ring can have any number of undulation peaks, and the number of peaks need not be equal for each ring. The undulation peaks 94 generally include a pair of strut portions 96 interconnected by curved portions 98, and the strut portions themselves are connected to adjacent strut portions by another curved portion. In a preferred embodiment, eight outer connectors 92 extend between structural support member 84 and outer ring 88, and each outer connector 92 is attached at one end to approximately the middle of a strut portion 96 of outer ring 88 and the structural support member 84 at the other end. As shown, outer connectors 92 may also have an undulated shape, although in alternate embodiments outer connectors 92 may have differing shapes. In another aspect of the preferred embodiment, outer connectors 92 may be evenly or symmetrically spaced about the structural support member 84. The inner ring 86 is attached to the outer ring 88 by a plurality of inner connectors 90 and, in a preferred embodiment, eight inner connectors 90 connect the rings. Inner connectors 90 extend from curved portion 98 of outer ring 88 to curved portion of inner ring 86. As shown in FIG. 20, in a preferred embodiment, inner connectors 90 have a simple curved shape. Other quantities, configurations, sizes and arrangements of connectors, rings and spacing can be used depending upon the desired results. Varying the connectors can provide for different amounts of flexibility and coverage. The type of configuration of rings and connectors shown addresses the need for radial and longitudinal expansion of branch portion 30, as well as branch vessel coverage. Other configurations and arrangements for the branch portion can be used in accordance with the invention.

Referring again to FIGS. 19 and 20, the stent pattern surrounding branch portion 30 may be modified with a different pattern to accommodate branch portion 30, as can all of the aforementioned embodiments. In particular, the rings 28 in the midsection 80 may be configured and dimensioned to be denser to provide sufficient coverage and flexibility to compensate for the area occupied by branch portion 30.

Referring now to FIG. 21, stent 79 is shown in the expanded configuration, with branch portion 30 deployed. Upon expansion of branch portion 30, the inner and outer rings 86, 88 shift about the longitudinal branch axis 83 and expand laterally away from the main stent body 14 and into the branch vessel to form a branch coverage portion. Upon expansion, the outer connectors 92 can move outwardly and the inner connectors 90 can straighten to a position substantially parallel to longitudinal branch axis 83. In a preferred embodiment, the expanded rings 86, 88 have substantially the same expanded diameter, although in alternate embodiments rings 86, 88 could also have different diameters to accommodate a tapered vessel, if, for example a tapered balloon is used. The branch portion 30 can be extended at different angles to the longitudinal axis 81 of the stent depending upon the geometry of the branch vessel being treated. In this embodiment, the branch portion 30 may preferably extend into the branch vessel about 1.5-3 mm.

Figure 22:
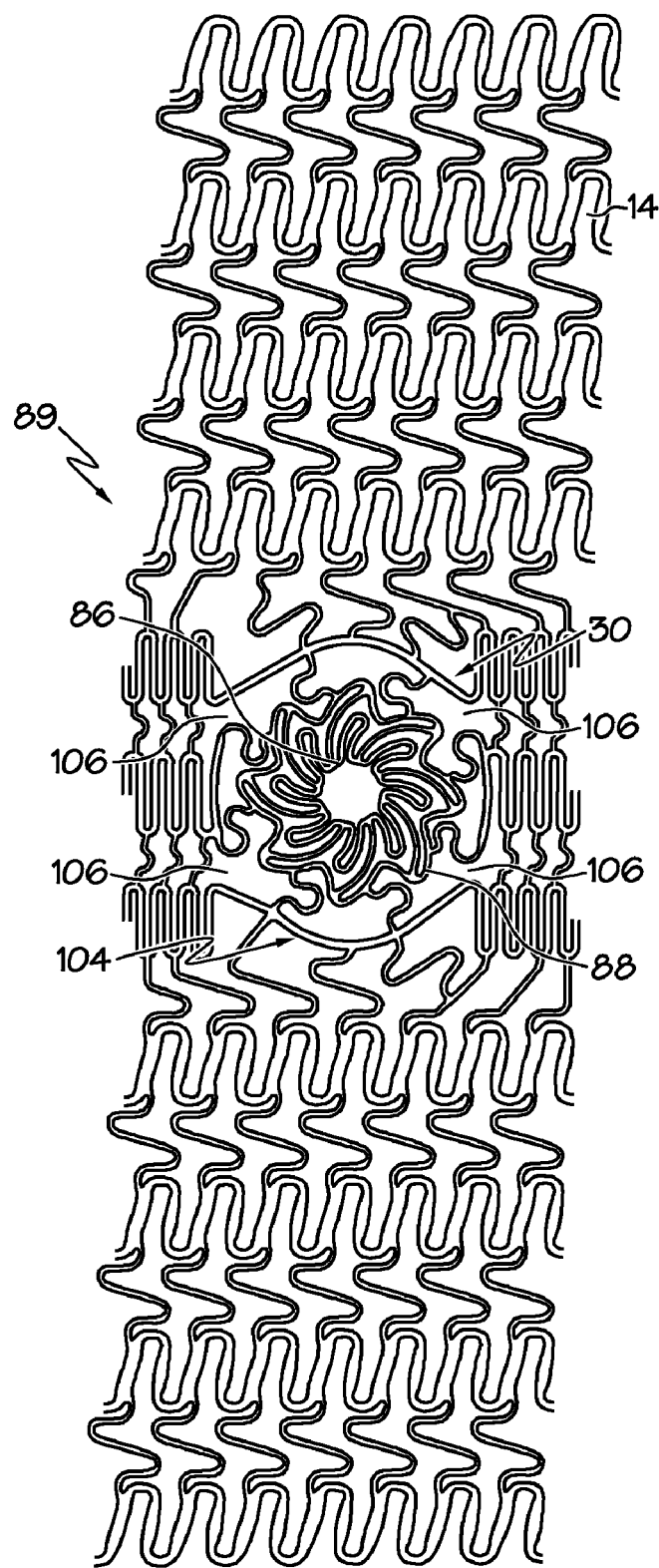
FIG. 22 is a flat view of another embodiment of an unexpanded stent in accordance with the present invention.

Referring now to FIG. 22, another embodiment of a stent 89 is shown having a main stent body 14 and another embodiment of a branch portion 30. Stent 89 is substantially similar to stent 79, except stent 89 has a discontinuous support member 104 surrounding a two concentric ring 86, 88 structure. Support member 104 has a generally elliptical shape and includes a plurality of discontinuities 106 along the perimeter. The configuration of the discontinuous support member facilitates additional flexibility of the branch portion during expansion and generally provides for accommodating a greater range of branch vessel geometries. In one aspect of a preferred embodiment, structural support member 84 may be elliptical to accommodate branch vessels extending at an angle to the main vessel.

Figure 23:
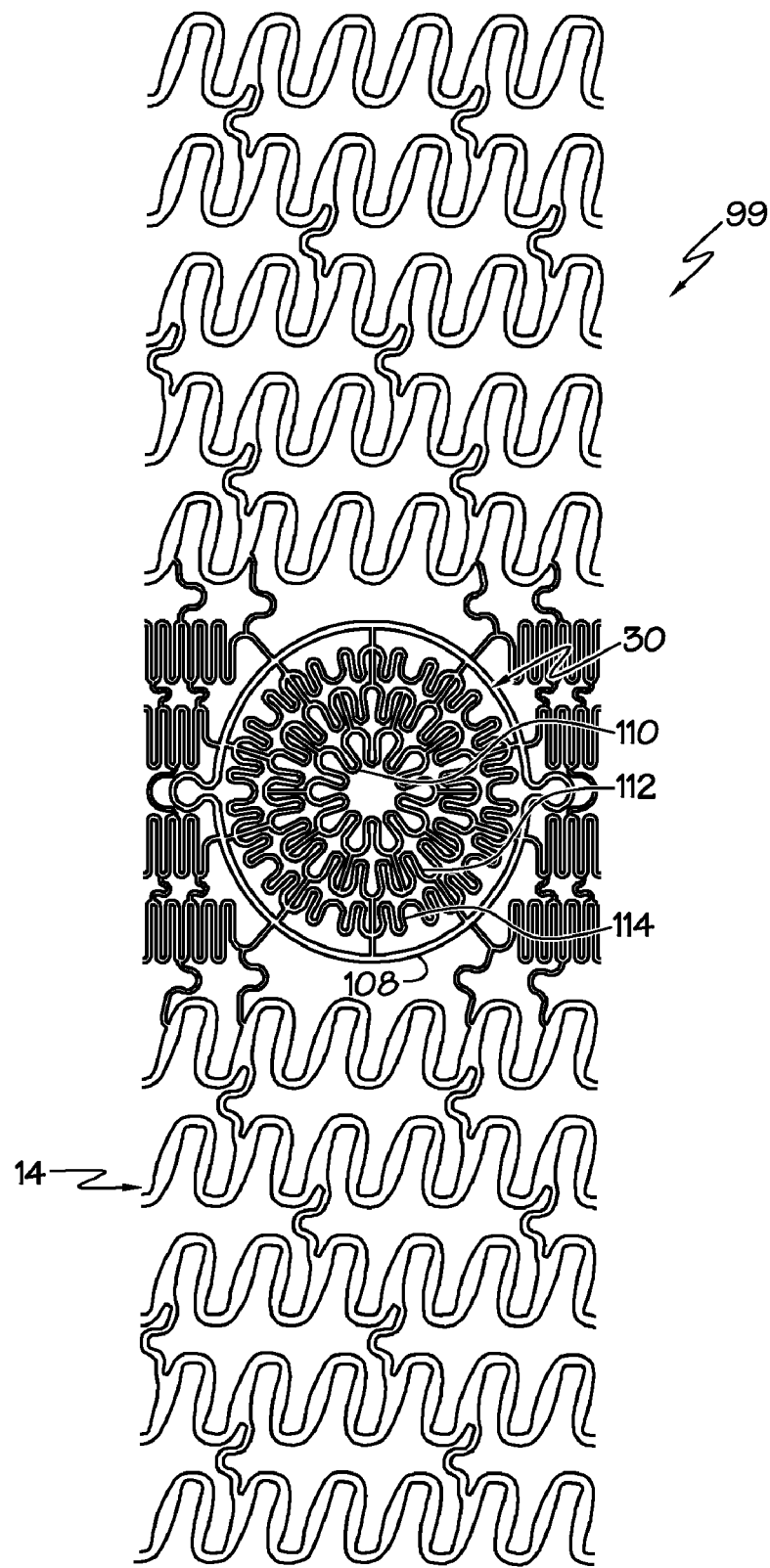
FIG. 23 is a flat view of another embodiment of an unexpanded stent in accordance with the present invention.
Figure 24:
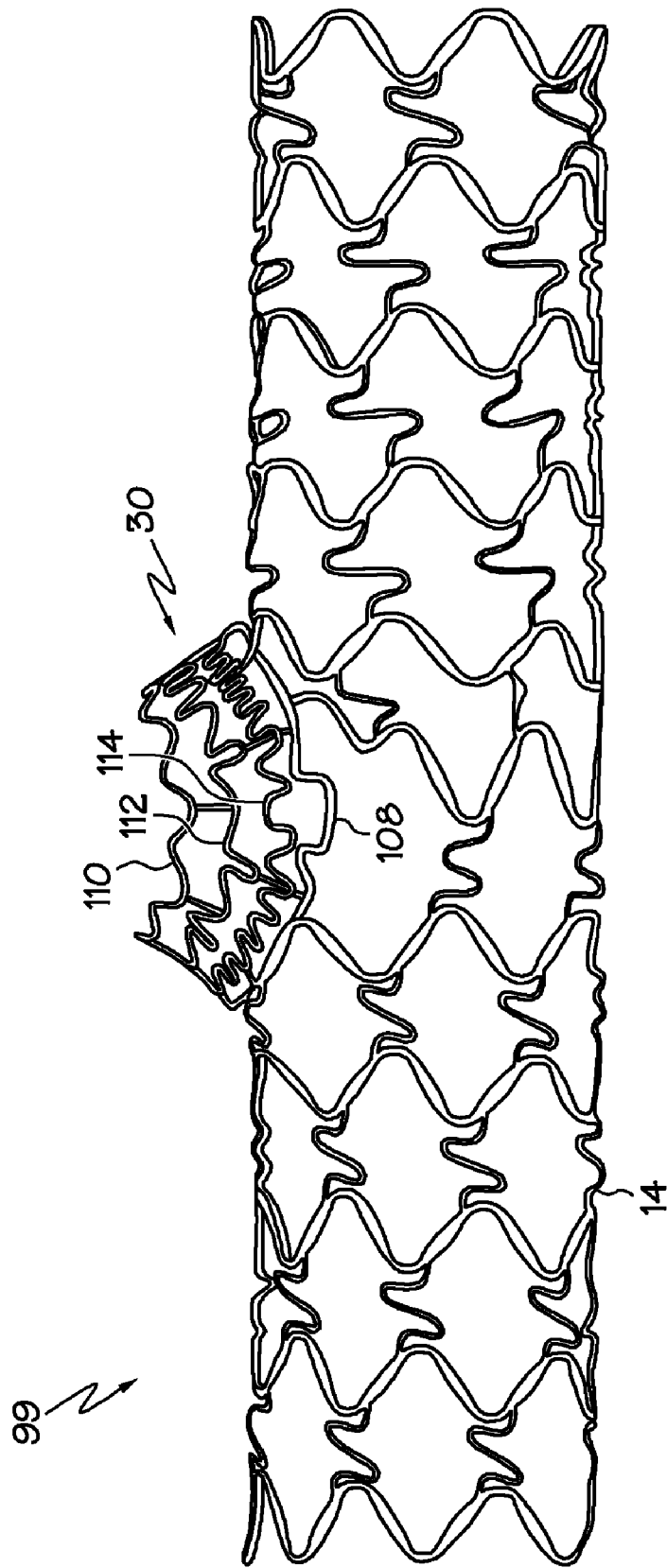
FIG. 24 is a view of an expandable branch portion of the stent of FIG. 23 in the expanded condition.
Figure 25:
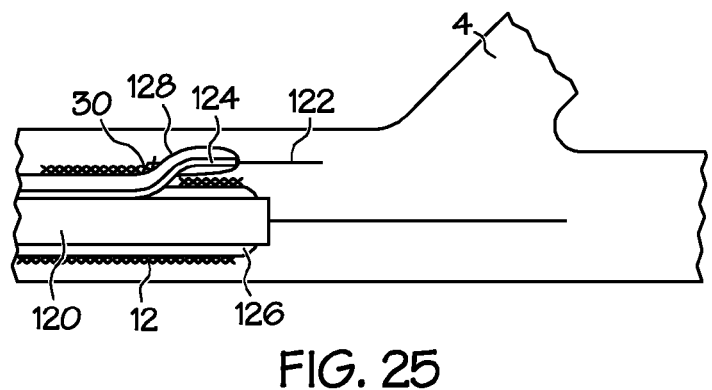
FIGS. 25-28 are illustrations of the steps for a method of inserting a stent of the present invention, according to one embodiment.
Figure 26:
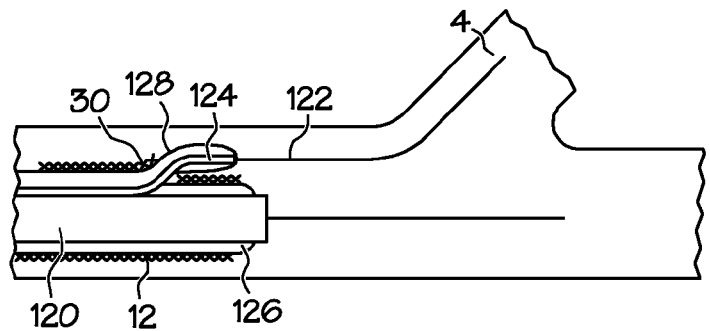
Figure 27:
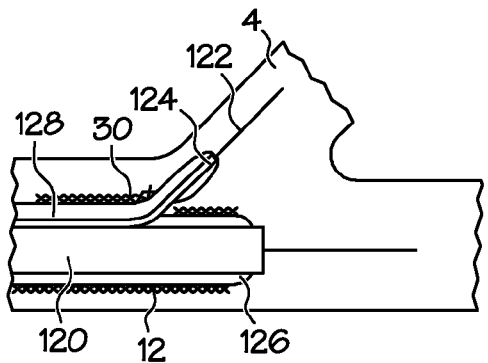
Figure 28:
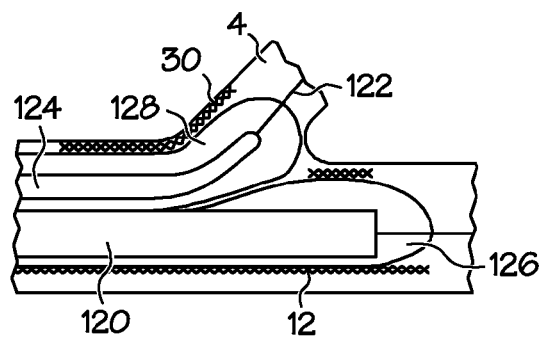
Figure 29:
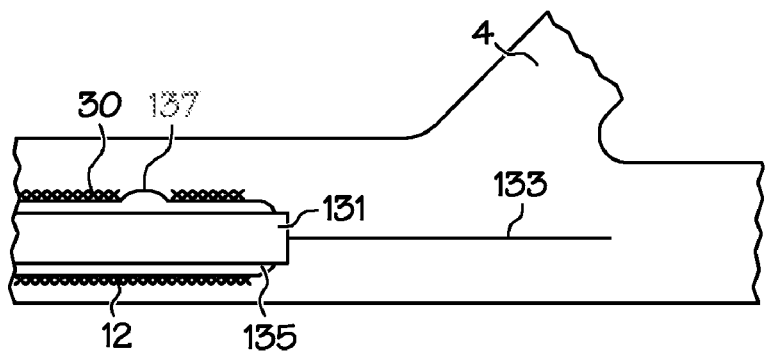
FIGS. 29-31 are illustrations of the steps for another method of inserting a stent of the present invention.
Figure 30:
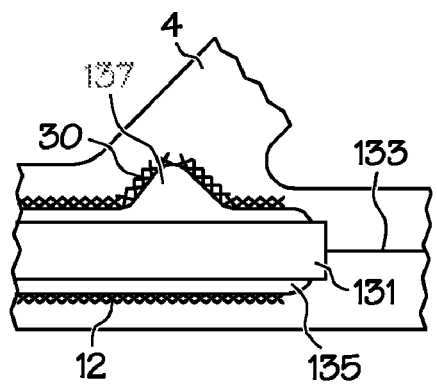
Figure 31:
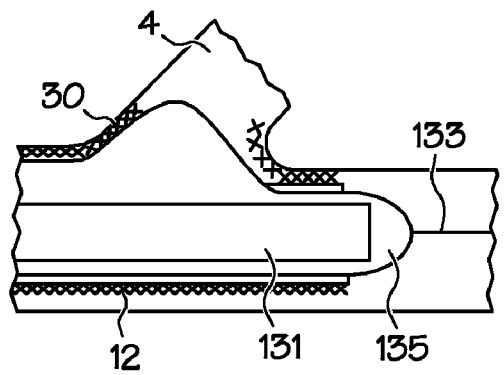
Figure 32:
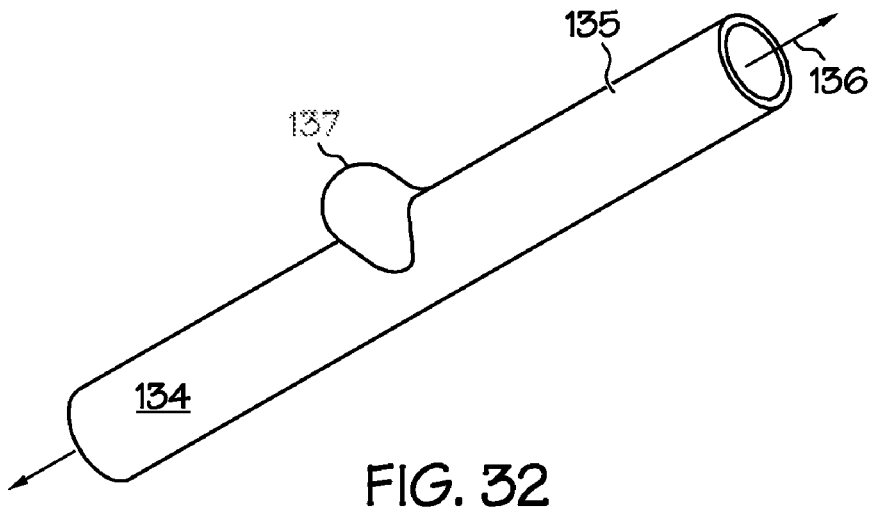
FIG. 32 is a view of a herniated balloon for use with the method of FIGS. 29-31.
Figure 33:
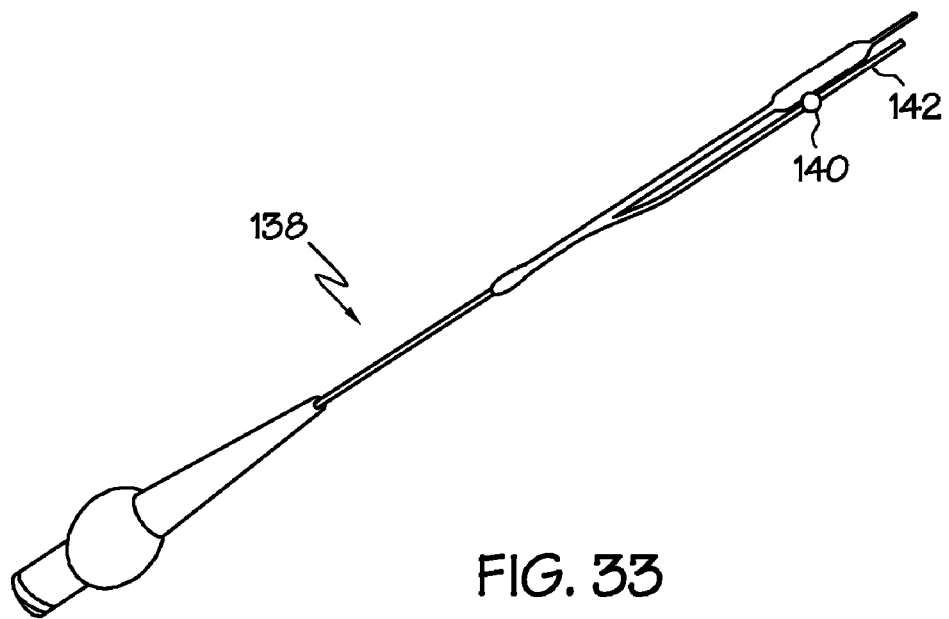
FIG. 33 is a view of another stent delivery system for inserting a stent in accordance with another method of the present invention.

Referring to FIGS. 23 and 24, another embodiment of a stent 99 is shown in the unexpanded and expanded states, respectively. Stent 99 comprises a main stent body 14 and another embodiment of a branch portion 30. Stent 99 is substantially similar to stent 79, except stent 99 has a branch portion 30 including a support member 108 surrounding three concentric rings 110, 112, 114 instead of two. As can be seen in FIG. 24, when stent 99 is expanded the three concentric ring structure of this embodiment facilitates additional branch wall support because a generally more dense pattern is created in branch portion 30 with the addition of another concentric ring.

Figure 34:
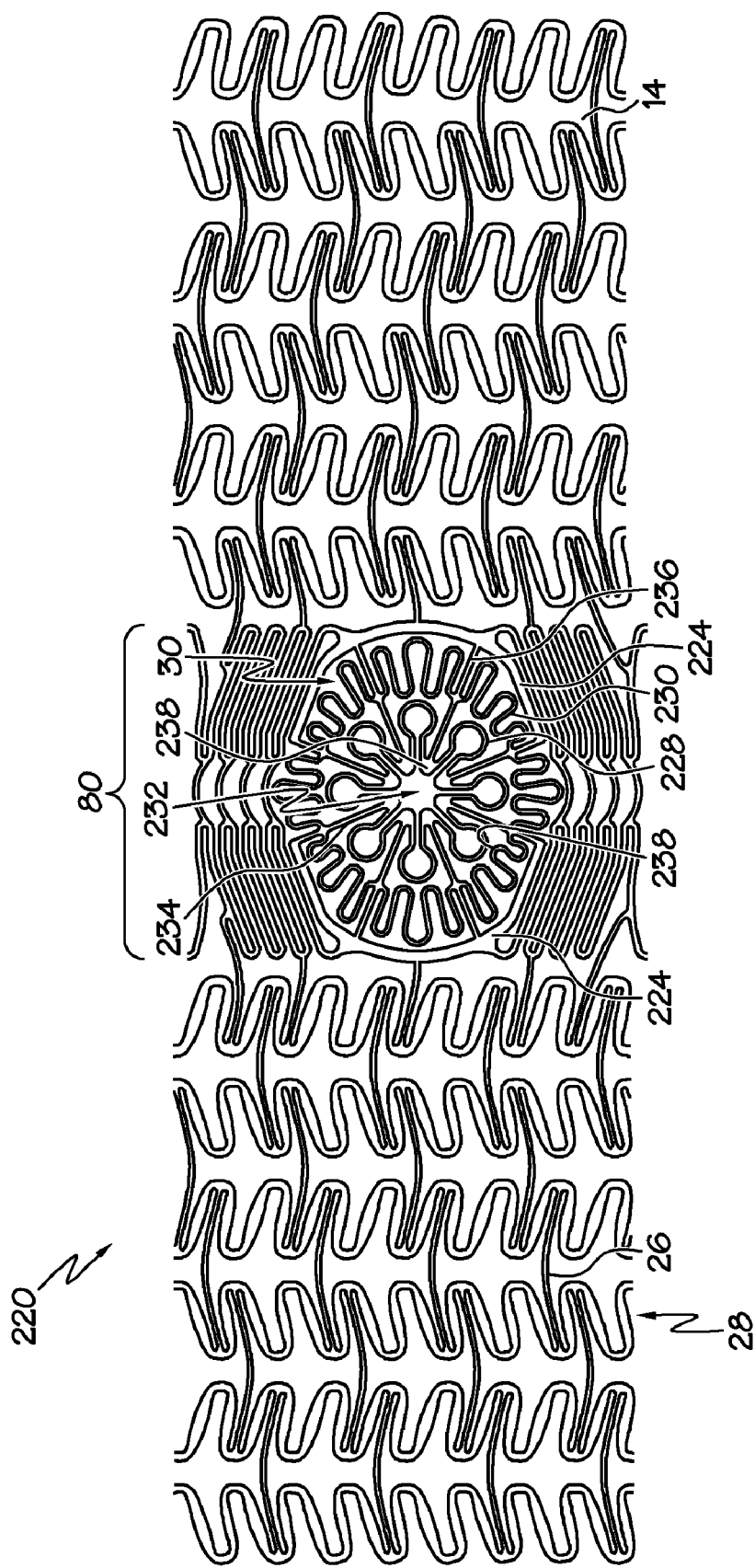
FIG. 34 is a flat view of another embodiment of an unexpanded stent in accordance with the present invention.

Referring to FIG. 34, an alternate embodiment of a stent 220 is shown having a main stent body 14 and another embodiment of branch portion 30. FIG. 34 is a flat view of stent 220 shown in an unexpanded condition where branch 30 has not been deployed. Main stent body 14 includes a main stent pattern having a generally repeatable ring 28 and connector 26 pattern. Branch portion 30 and the surrounding midsection 80 interrupt the repeatable ring 28 and connector pattern of stent 220. Branch portion 30 is configured to be extendable into the branch vessel such that the branch portion 30 contacts the entire periphery or circumference of the inner wall of the branch vessel in the expanded configuration.

In a preferred embodiment, transition members 224 may be provided as a transition between the main stent body 14 and branch portion 30. Transition members 224 comprise generally elliptical half portions positioned in an opposing relation with a space 246 therebetween. Transition members 224 surround a two concentric ring 228, 230 structure and a central branch opening 232. Branch opening 232 provides access to the side branch vessel when stent 220 is in the unexpanded condition and a side sheath may pass through opening 232. Rings 228 and 230 are interconnected by a plurality of inner connectors 234. Outer ring 230 is connected to transition members 224 by a plurality of outer connectors 236. Rings 228, 230 are generally curvilinear members and include undulation petals, prongs, or peaks 238. In this embodiment outer ring 230 includes a greater number of peaks than inner ring 228. Preferably eight outer connectors and eight inner connectors interconnect transition members 224 and rings 228, 230. In this embodiment, inner and outer connectors 234, 236 are generally straight members and are preferably aligned radially to extend toward the center of branch portion 30. In operation, the intersection of outer connectors 236 with transition members 224 form a pivot point about which petals 238 may unfold or pivot outward into the side branch vessel. In a preferred embodiment, the generally straight inner and outer connectors pivot together such that the petals 238 open like a flower.

Figure 35:
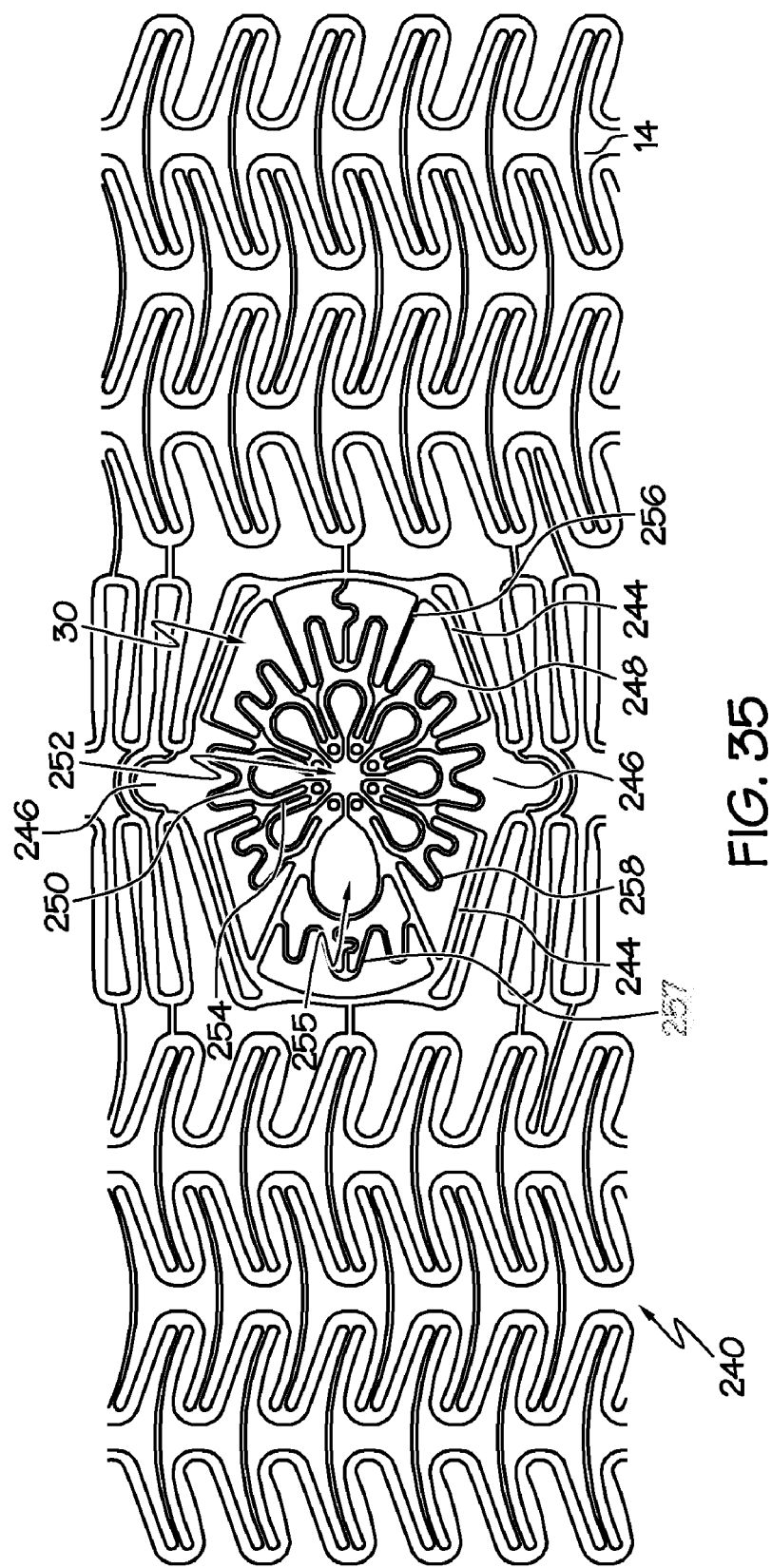
FIG. 35 is a flat view of another embodiment of an unexpanded stent in accordance with the present invention.
Figure 36:
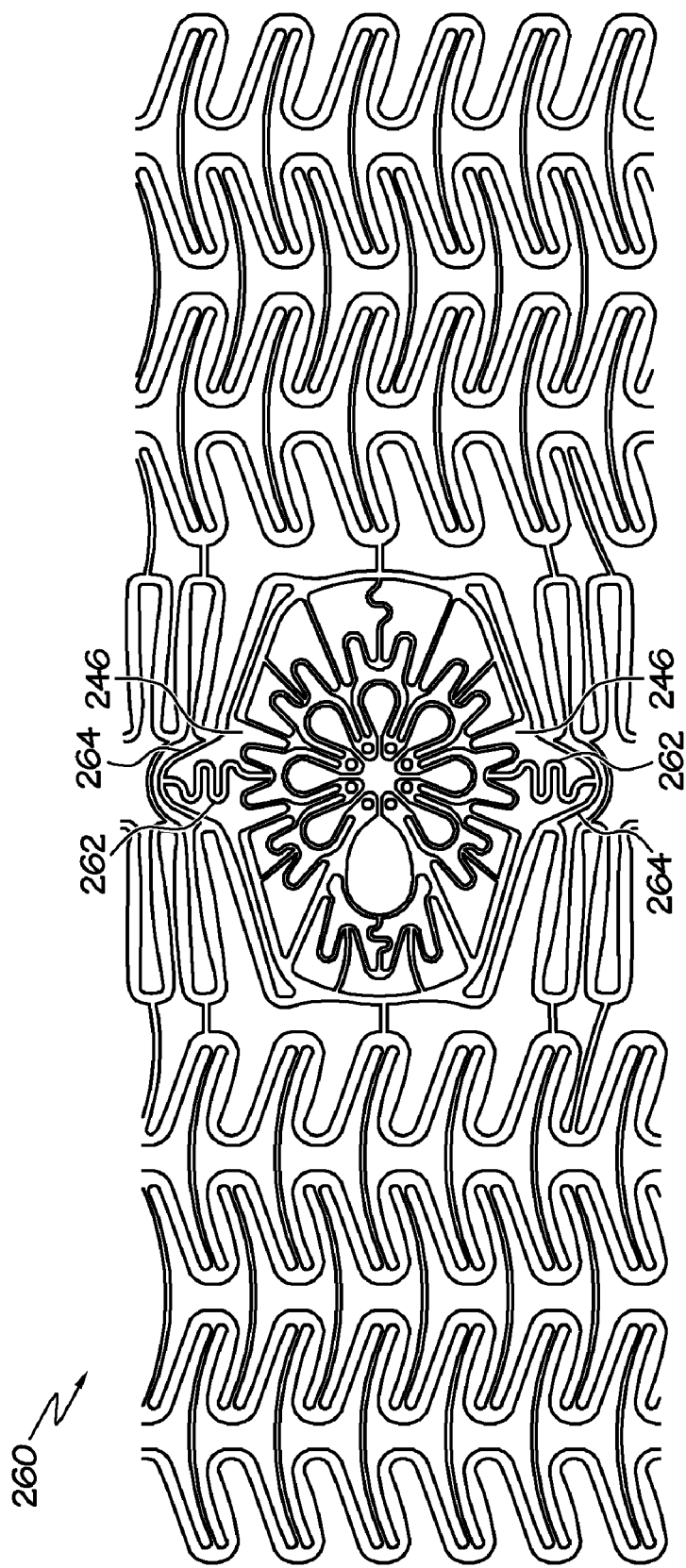
FIG. 36 is a flat view of another embodiment of an unexpanded stent in accordance with the present invention.

Referring to FIG. 35, an alternative embodiment of a stent 240 is shown having an alternate embodiment of a branch portion 30. Stent 240 includes structural support members 244 as a transition between the main stent body 14 and branch portion 30. Support members 244 comprise generally elliptical half portions positioned in an opposing relation with a space 246 therebetween. Support members 244 surround a two concentric ring 248, 250 structure and a central branch opening 252. Rings 248 and 250 are interconnected by a plurality of inner connectors 254. Outer ring 248 is connected to structural support members 244 by a plurality of outer connectors 256. Rings 248, 250 are generally curvilinear members and include undulation petals, prongs, or peaks 258. An auxiliary access opening 255 interrupts rings 248, 250 and provides access to the side branch vessel when stent 240 is in the unexpanded condition. A ring portion 257 extends between outer connectors 256 proximal to auxiliary access opening 255. In this embodiment, auxiliary access opening 255 is generally larger than central branch opening 252 to more readily receive a side sheath therethrough and to allow for greater access to the side branch. Auxiliary access opening 255 is preferably positioned proximal to central branch opening 252 when loaded on a stent delivery system however auxiliary access opening 255 can have varying positions in alternate embodiments An alternate embodiment of a stent 260 is shown in FIG. 36 that is similar to stent 240 and it additionally includes lateral connecting members 262 that extend through space 246 and connect the outer ring 250 to struts 264 laterally outside branch portion 30. In this regard, when branch portion 30 is extended into the side branch, struts 264 are pulled radially inward to support the circumference of the ostium. This additional structure improves radial strength and provides additional support to the vessel wall.

Figure 37:
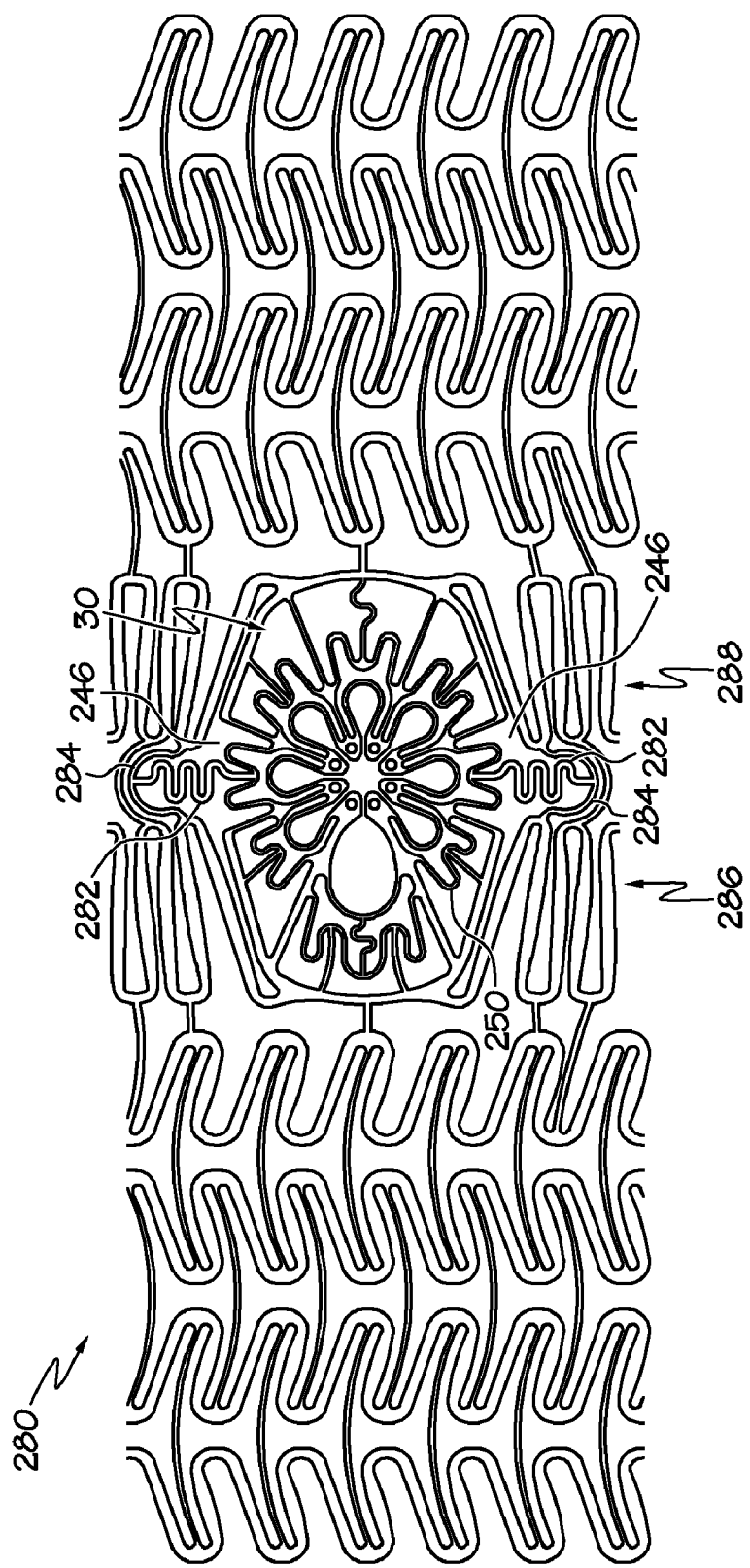
FIG. 37 is a flat view of another embodiment of an unexpanded stent in accordance with the present invention.

Referring to FIG. 37, an alternate embodiment of a stent 280 is shown that is similar to stent 260 and includes lateral connecting members 282 that extend through space 246 and connect the outer ring 250 to struts 284 laterally outside branch portion 30. Struts 284 are generally longitudinal connecting members spanning longitudinally between adjacent strut rings 286, 288. In this embodiment, struts 284 are generally curved members having a general omega shape. Struts 284 have a smaller radius of curvature than struts 264 of stent 240 described above. When branch portion 30 is extended into the side branch, struts 284 are pulled radially inward to support the circumference of the ostium In addition, the general omega shape and comparatively smaller radius of curvature allow for greater expansion of struts 284 and permits greater movement or expansion of branch portion 30 without affecting deformation of the surrounding midsection 80. In alternate embodiments, other geometries of struts 284 may be used to accomplish the same purpose.

Figure 38:
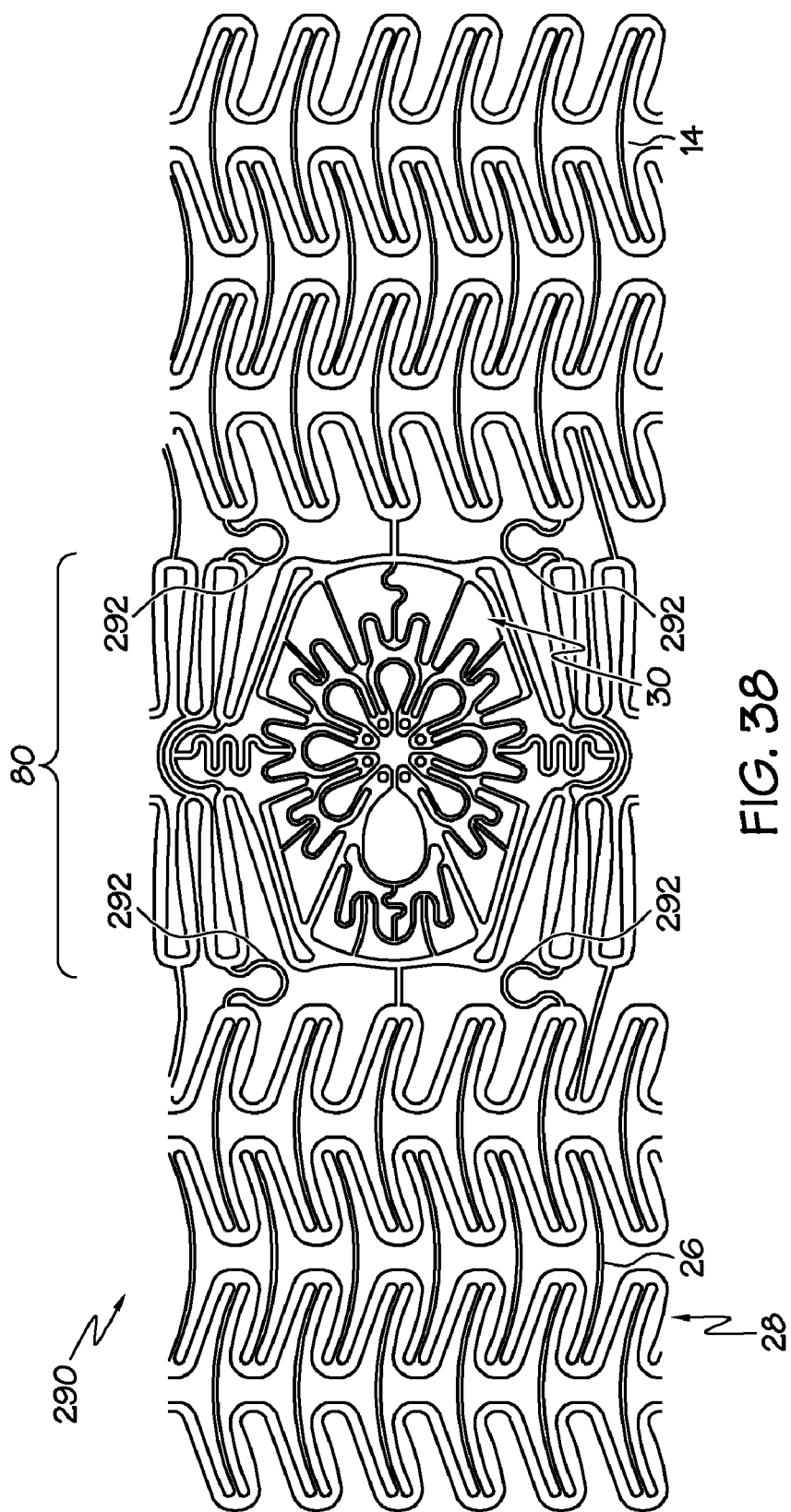
FIG. 38 is a flat view of another embodiment of an unexpanded stent in accordance with the present invention.
Figure 39:
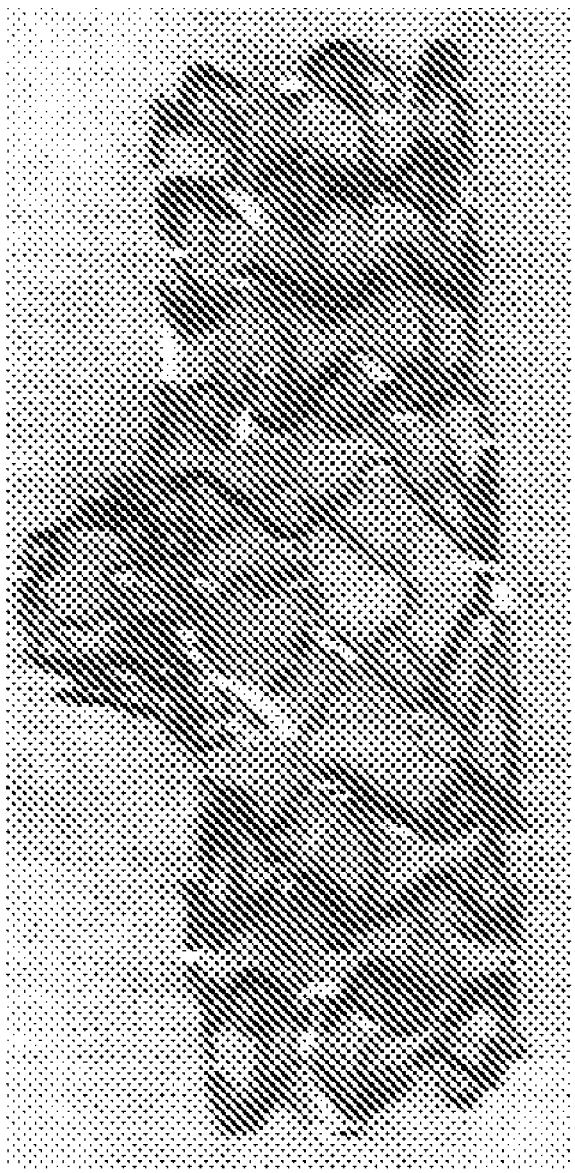
FIG. 39 is a perspective view of the stent of FIG. 38 in the expanded configuration.

Referring to FIGS. 38 and 39, an alternate embodiment of a stent 290 is shown that is similar to stent 280, described above, and generally includes at least one omega shaped connecting member 292 extending longitudinally outside branch portion 30 and connecting the midsection 80 to the repeatable ring 28 and connector 26 pattern of main stent body 14. As with prior embodiments, branch portion 30 is configured to be extendable into the branch vessel such that the branch portion 30 contacts the entire periphery or circumference of the inner wall of the branch vessel in the expanded configuration. Also, because midsection 80 has a different pattern than the main stent body, midsection 80 may expand radially to a different extent than the main stent pattern when branch portion 30 is extended into the side branch vessel Connecting members 292 are configured to expand or contract accordingly to accommodate differential expansion of midsection 80 with respect to the main stent body. In this regard, connecting members 292 provide a cushion, dampening member, or act as a buffer between the expansion of the main stent body 14 and midsection 80 so that the expansion of main stent body 14 has a limited effect on the midsection 80 in operation and vice versa. In particular, the generally omega shape of connecting members 292 allow for greater expansion of connecting members 292 as compared to straight or substantially straight connector geometries. In alternate embodiments, other geometries of connecting members 292 may be used to accomplish the same purpose, that is to provide a cushion, dampen, or buffer the expansion of the midsection 80 with respect to the main stent body 14.

Figure 40:
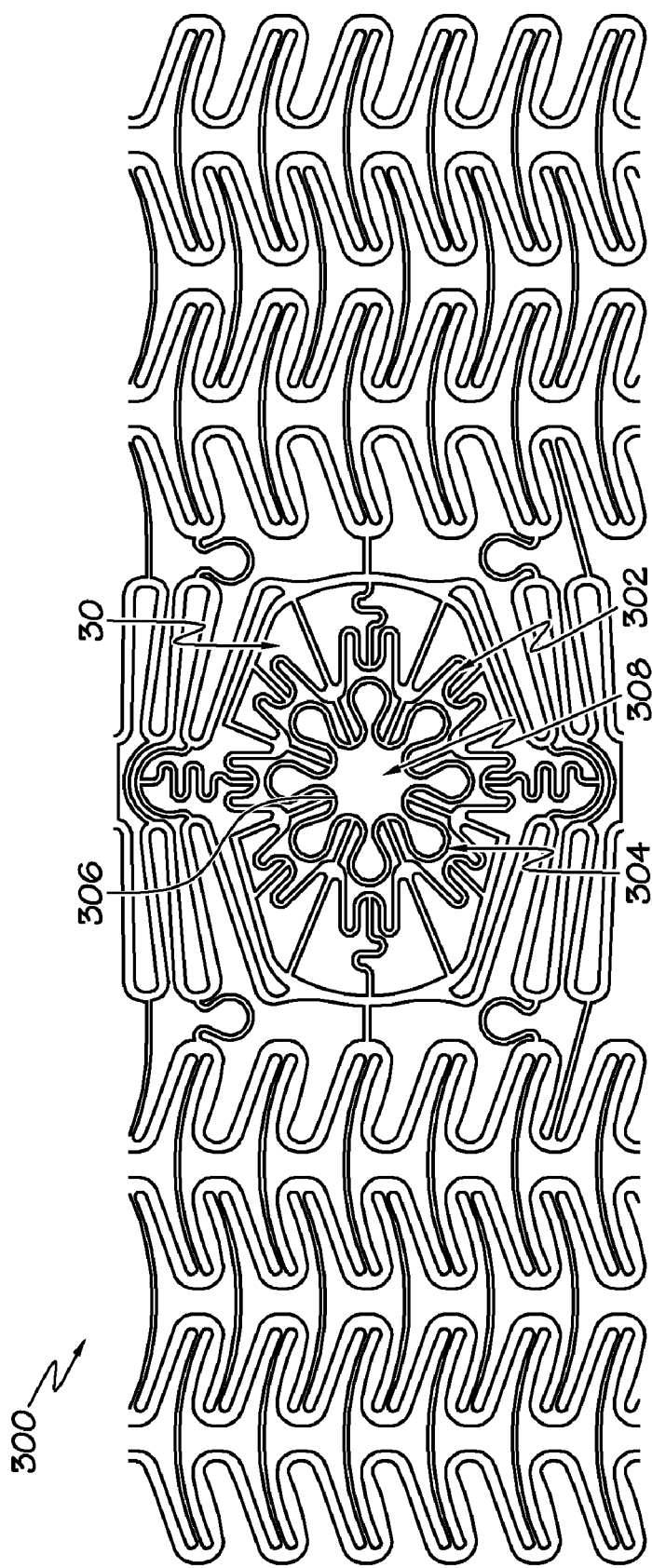
FIG. 40 is a flat view of another embodiment of an unexpanded stent in accordance with the present invention.
Figure 41:
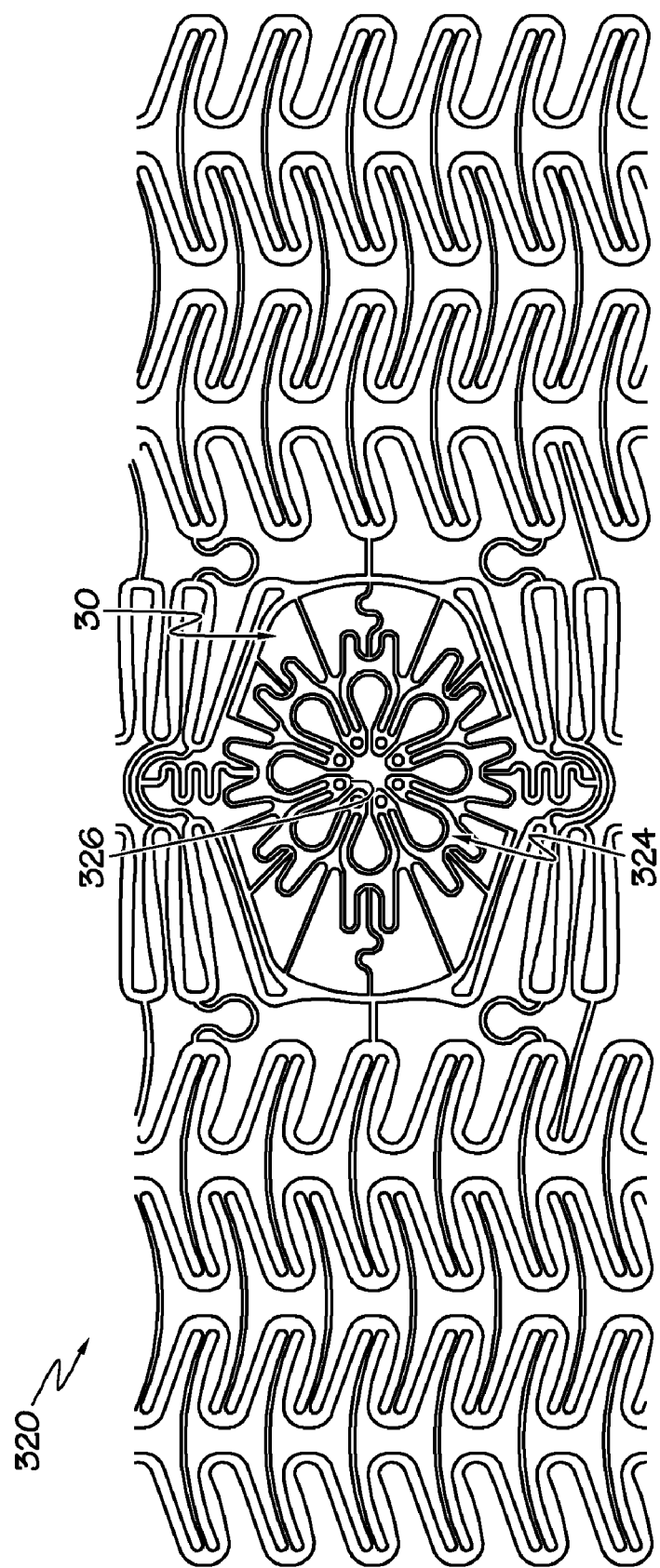
FIG. 41 is a flat view of another embodiment of an unexpanded stent in accordance with the present invention.
Figure 42:
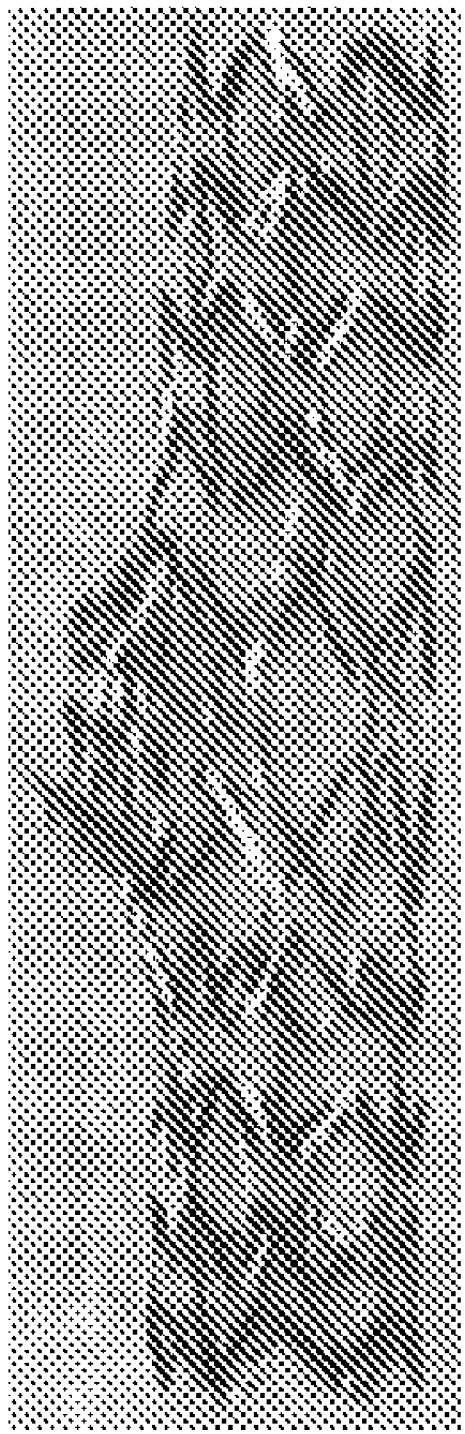
FIG. 42 is a perspective view of the stent of FIG. 41 in the expanded configuration.

Referring to FIG. 40, an alternate embodiment of a stent 300 is shown that is similar to stent 290, described above, and generally includes a branch portion 30 including an outer ring 302, and an inner ring 304. The inner ring defines undulation petals, prongs, or peaks 306 surrounding a central branch opening 308. Branch opening 308 provides access to the side branch vessel when stent 300 is in the unexpanded condition. In this embodiment, undulation peaks 306 of inner ring 304 have a relatively larger radius of curvature, i.e. they are less pointed, than, for example, the corresponding peaks 238 of inner ring 228 of stent 220, described above. For example, in a preferred embodiment peaks 306 may have a radius of curvature in the range of about 0.125 mm to about 0.225 mm, and preferably about 0.170 mm. In comparison, in a preferred embodiment peaks 238 of stent 220 may generally have a radius of curvature between about 0.025 mm to about 0.125 mm. In this regard, the geometry of peaks 306 may permit and/or facilitate the use of particular balloon types and designs. In particular, the design and shape of peaks 306 in this embodiment are less likely to pinch or puncture certain balloon designs. Although, in this embodiment branch portion 30 does not include an auxiliary access opening 255 to provide access to the side branch vessel, as with stents 240, 260, 280, and 290, in alternative embodiments, branch portion 30 may include such an auxiliary access opening. Referring to FIGS. 41 and 42, an alternative embodiment of a stent 320 is shown that is similar to stent 300, described above, except the inner ring 324 has undulation peaks 326 with a smaller radius of curvature than peaks 308 described above. Also, in this embodiment each peak 326 defines a hole configured and dimensioned to accommodate, for example, a marker.

Figure 43:
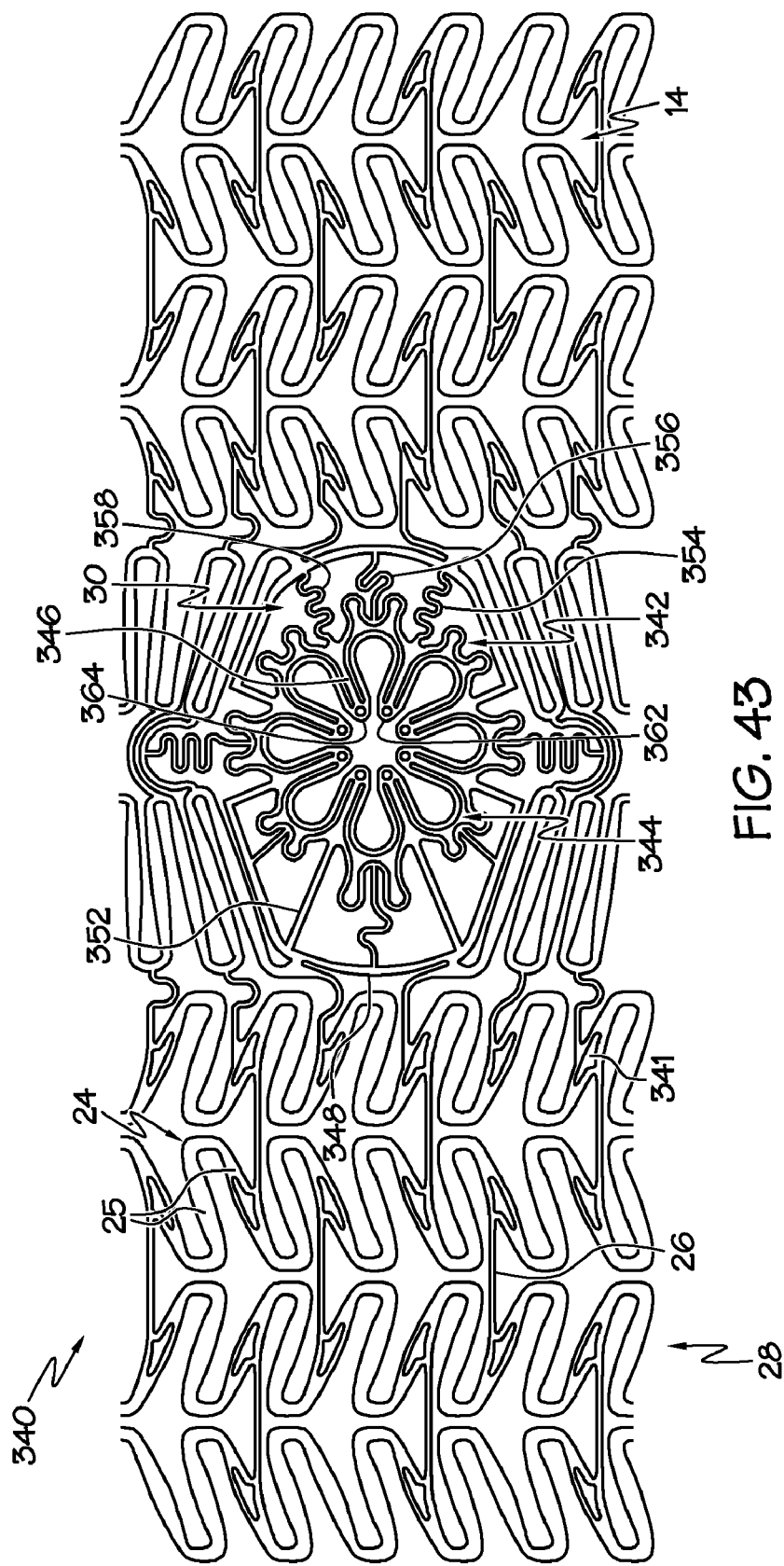
FIG. 43 is a flat view of another embodiment of an unexpanded stent in accordance with the present invention.
Figure 44:
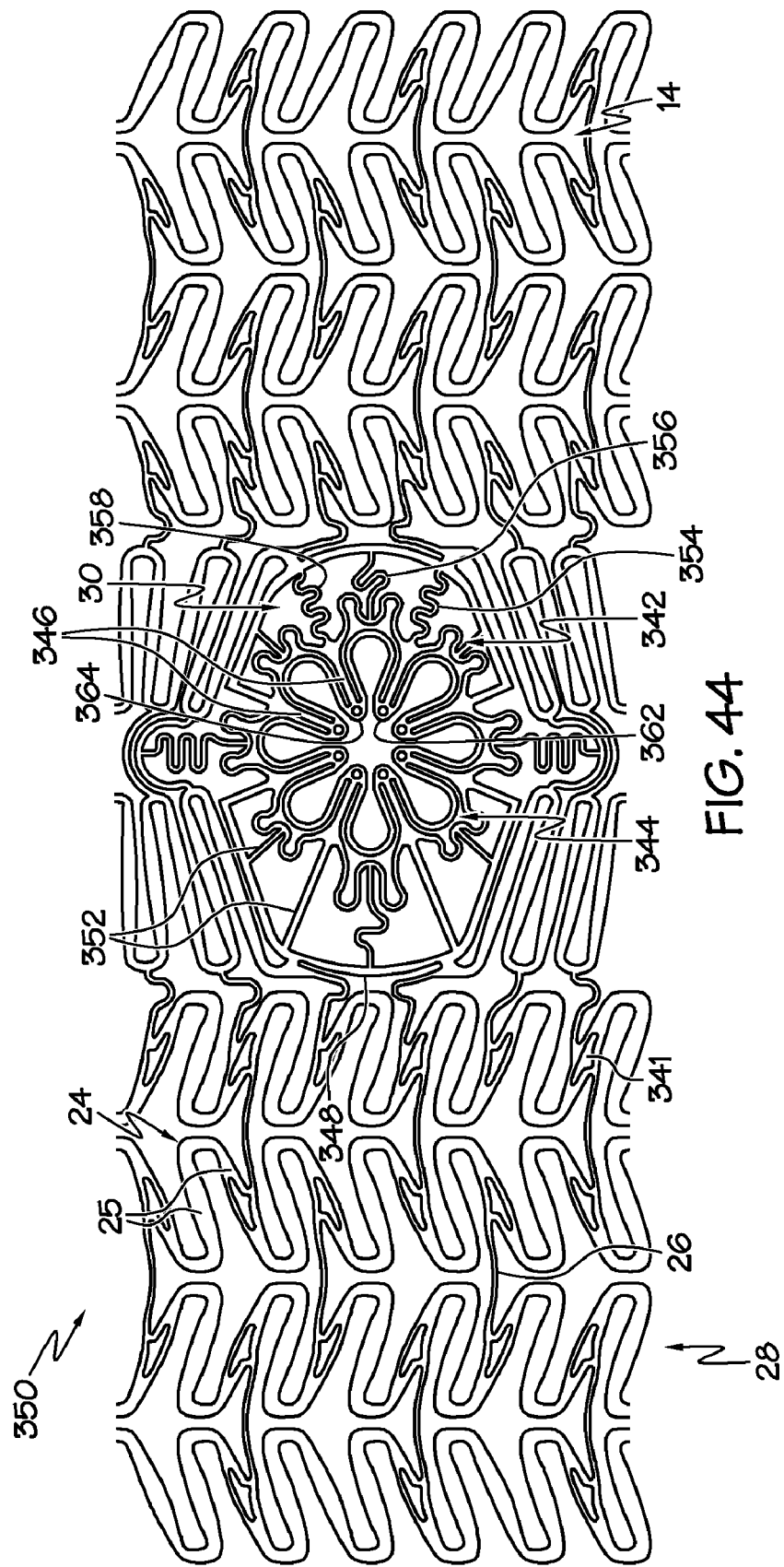
FIG. 44 is a flat view of another embodiment of an unexpanded stent in accordance with the present invention.
Figure 45:
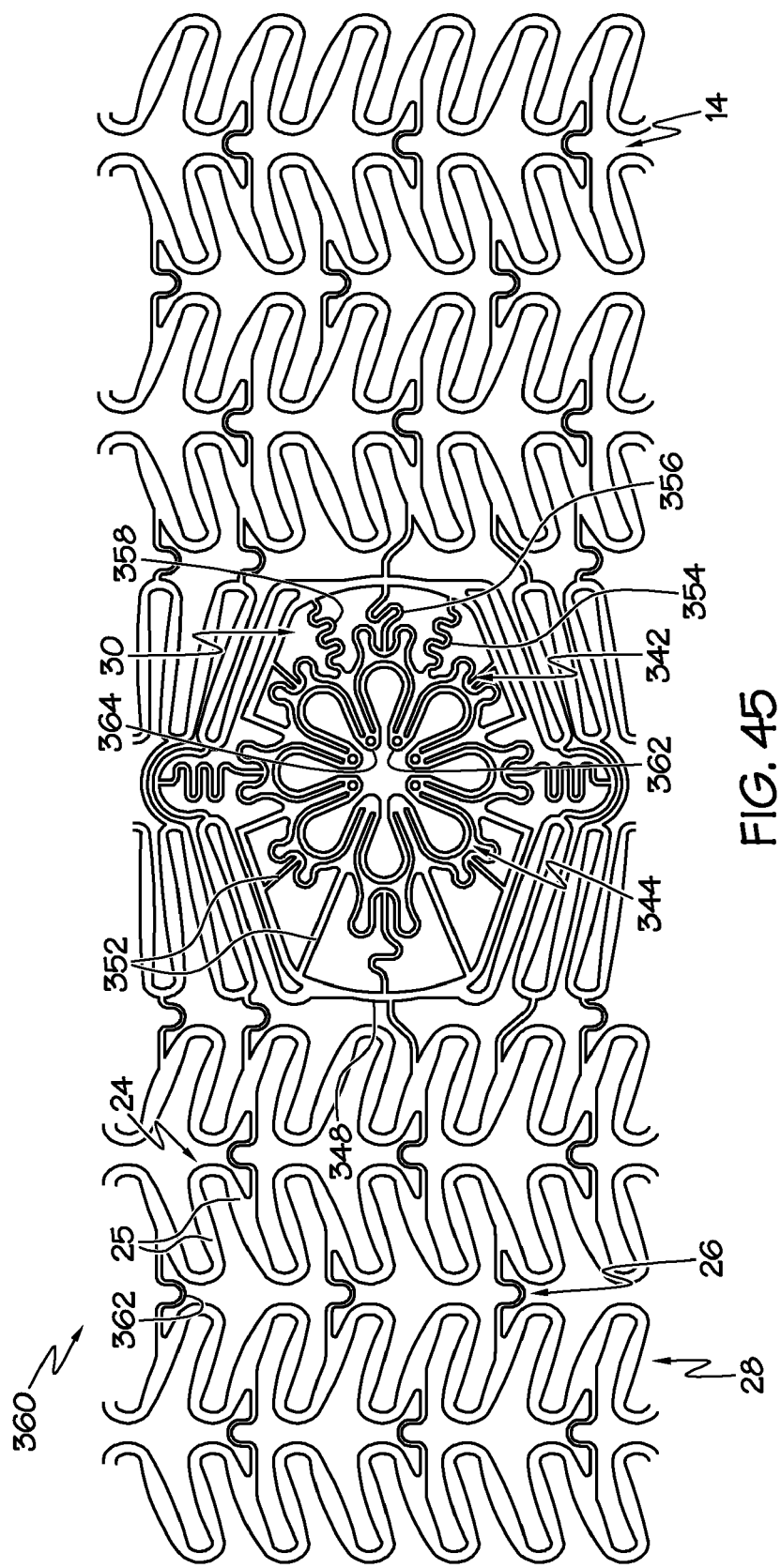
FIG. 45 is a flat view of another embodiment of an unexpanded stent in accordance with the present invention.

Referring to FIGS. 43-45, alternate embodiments of stents are shown having a main stent body 14 with alternative main stent pattern designs. In the embodiments of FIGS. 43-45, the main stent patterns have an open cell structure. For example, stents 340, 350, 360, each have a main stent body 14 having a generally repeatable ring 28 and connector 26 pattern and the connectors 26 are spaced apart and alternate every two or three strut pairs defining a more open cell structure as compared to providing connectors spaced apart or alternating every strut pair. In this regard, stents 340, 350, 360, have less stent material making up the main stent body and can have desirable clinical effects in certain applications. For example, if the stent is made from a metal material, it can be beneficial to have a smaller metal surface area ratio when the stent is installed in a patient. Referring now to FIGS. 43-45, stents 340, 350, 360 each have connectors 26 extending generally longitudinally between adjacent circumferential rings 28 and connecting to respective longitudinal strut portions 25 of longitudinally adjacent struts 24 of adjacent rings 28. Connectors 26 are spaced apart and alternately connect every other pair of longitudinally adjacent struts connectors 26 are spaced apart and alternate every two or three strut pairs defining a more open cell structure. As shown in FIG. 43, one embodiment of a stent 340 may have connectors 26 that are substantially straight and may extend between the midsections of the longitudinal strut portions 25 of longitudinally adjacent struts 24. Also, the midsection of longitudinal strut portions 25 may include a hole, space, or void 341, thus further reducing the amount of material used. In some embodiments, void 341 may be provided adjacent the junction of connector 26 with longitudinal strut portion 25 and in alternate embodiments (e.g. FIG. 46) a void 341 may be provided at the midsection of every longitudinal strut portion. In this regard, the hole, space, or void permits the design of stent patterns utilizing even less material to, for example, further decrease the metal to surface area ratio. As shown in FIG. 44, an alternate embodiment of a stent 350 is shown having connectors 26 that are generally arcuate and extend between the midsections of the longitudinal strut portions 25 of longitudinally adjacent struts 24. Referring to FIG. 45, another embodiment of a stent 360 is shown having connectors 26 that include an omega shaped feature 362 which permits expansion of connectors 26 in the longitudinal direction. In alternate embodiments, other geometries of connectors 26 may be used to accomplish the same purpose.

Stents 340, 350, 360, shown in FIGS. 43-45, generally include a branch portion 30 similar to stent 320 (FIG. 41) including an outer ring 342, and an inner ring 344. Rings 342 and 344 are interconnected by a plurality of inner connectors 346. Outer ring 344 is connected to elliptical transition members 348 by a plurality of outer connectors 352. In these embodiments, outer connectors 352 include a subset of distal outer connectors 354, 356, 358 that extend from the distal side of outer ring 344 to the elliptical transition member on the distal side of branch portion 30. Distal outer connectors 354, 356, 358 are generally S-shaped, zigzag-shaped, or wavelike. In this regard, the wavelike shape of distal outer connectors may be deformed to a greater extent and accommodate more expansion than, for example, a straight outer connector design. In these embodiments, distal outer connectors 354, 356, 358 may generally accommodate large angles of rotation of the distal portion of branch portion 30 into the side branch vessel during implantation For example, the distal petals 362, 364 may rotate more than 90.degree. during implantation in the side branch vessel.

Figure 46:
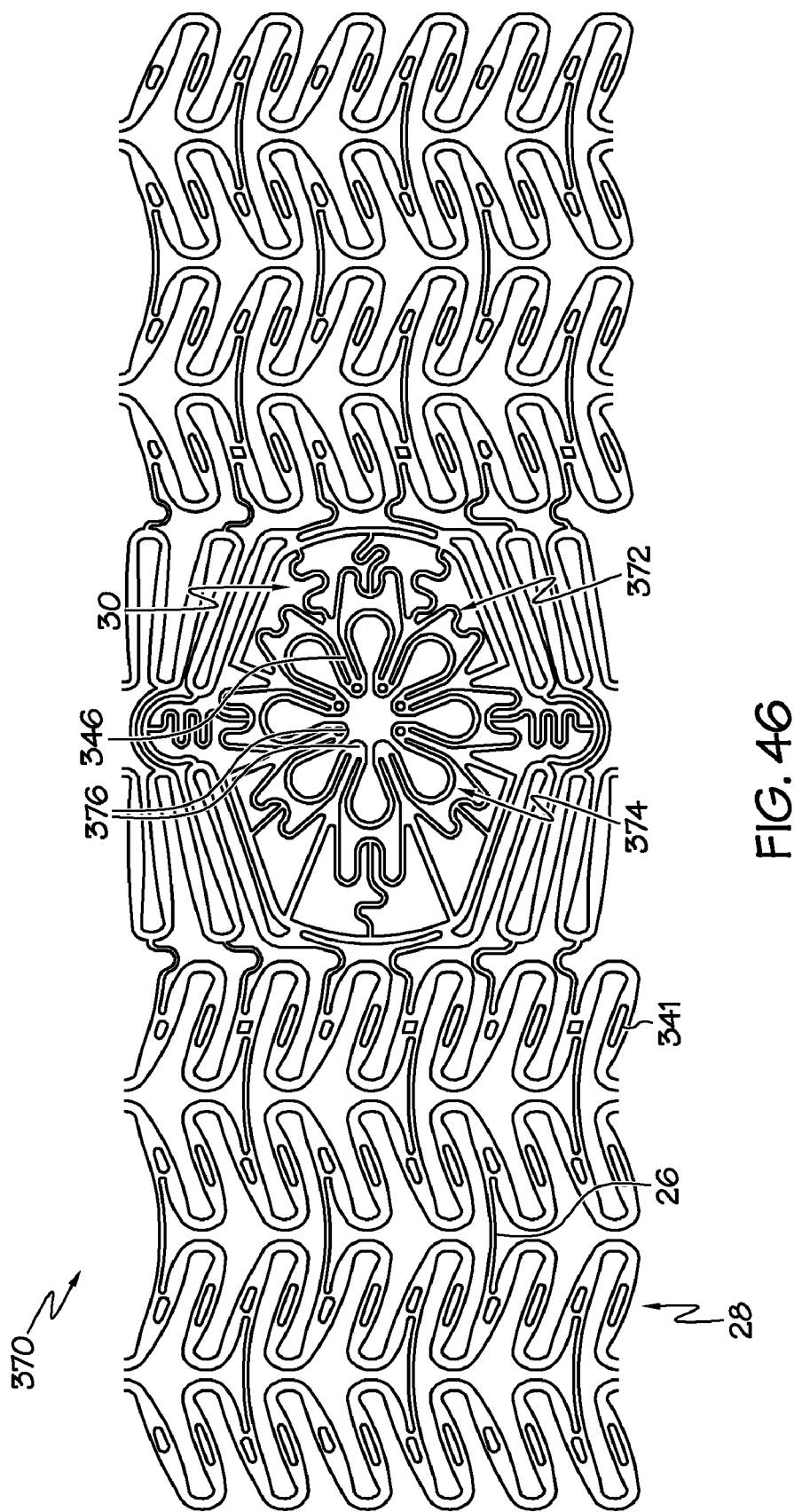
FIG. 46 is a flat view of another embodiment of an unexpanded stent in accordance with the present invention.
Figure 47:
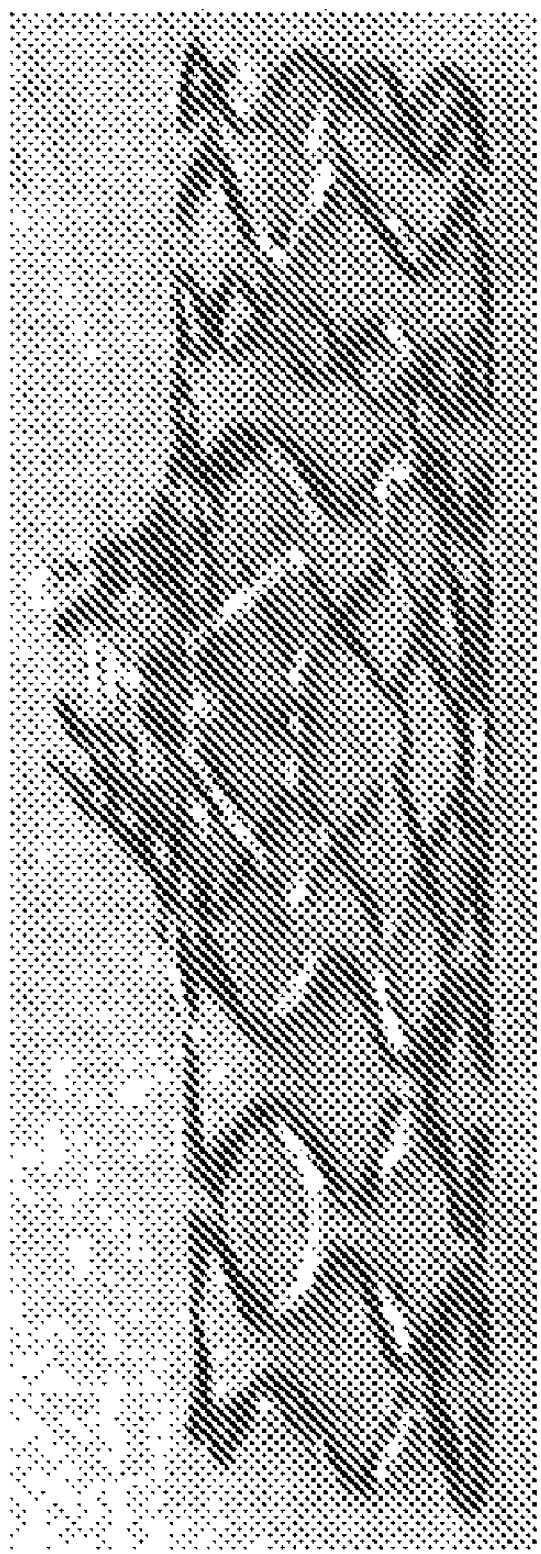
FIG. 47 is a perspective view of the stent of FIG. 46 in the expanded configuration.

Referring to FIGS. 46 and 47, an alternate embodiment of a stent 370 is shown that is similar to stent 360, described above, and generally includes a branch portion 30 including an outer ring 372, and an inner ring 374. Rings 372, 374 are generally curvilinear members and include undulation petals, prongs, or peaks 376. In this embodiment outer ring 372 is generally less curvilinear than outer ring 342 of stents 340, 350, 360 described above. For example as shown in FIG. 46, outer ring 372 can be viewed as a series of interconnected connected W-shaped sections, wherein the legs of the W-shaped sections are straighter than the comparable sections of outer ring 342 described above. In this regard, the geometry of outer ring 372 may permit and/or facilitate different type of expansion characteristics of the branch portion 30 upon installation into a side branch vessel. In alternate embodiments, other geometries of outer ring 372 may be used.

Figure 48:
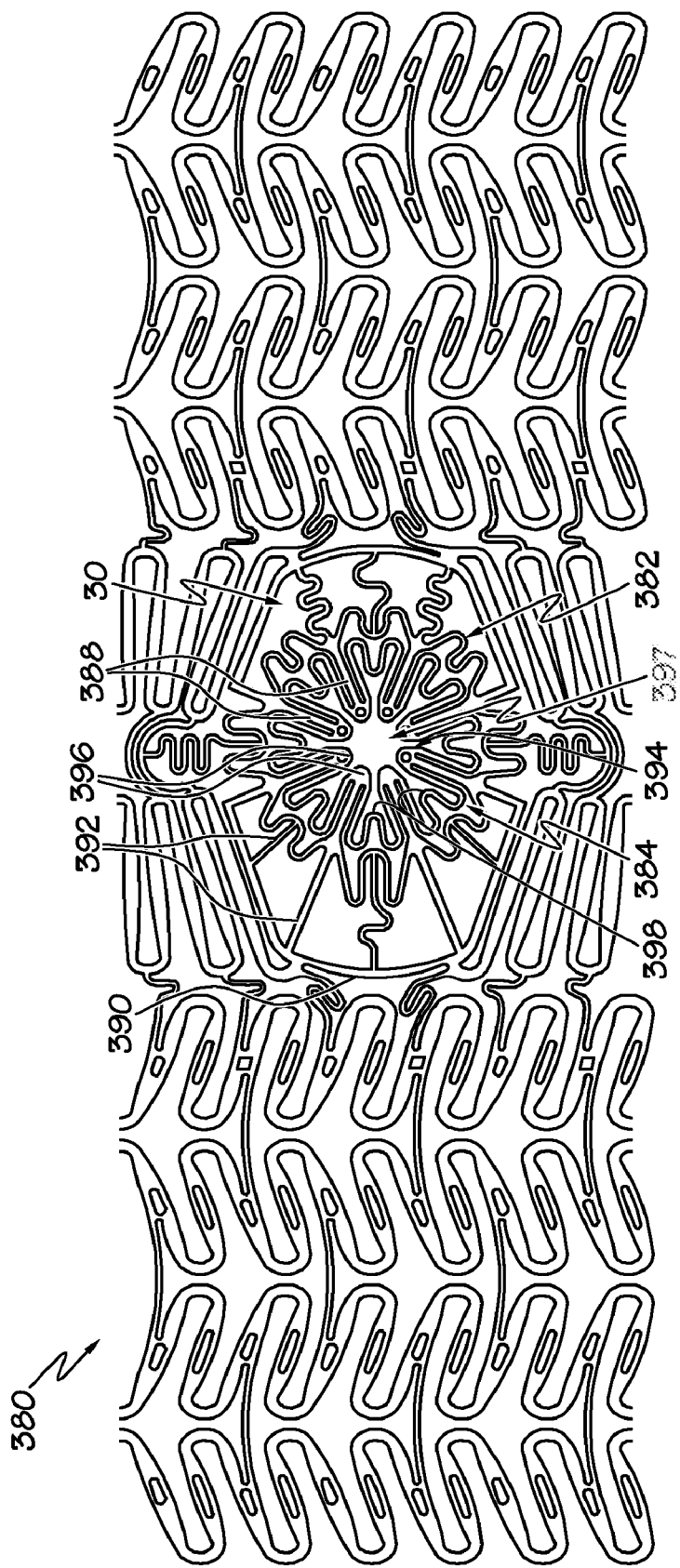
FIG. 48 is a flat view of another embodiment of an unexpanded stent in accordance with the present invention.

Referring to FIG. 48, an alternate embodiment of a stent 380 is shown that is similar to stent 370, described above, and generally includes a branch portion 30 including an outer ring 382, and an inner ring 384. Rings 382 and 384 are interconnected by a plurality of inner connectors 388. Outer ring 382 is connected to elliptical transition members 390 by a plurality of outer connectors 392. Rings 382, 384 are generally curvilinear members and include undulation petals, prongs, or peaks 394. In this embodiment outer ring 382 generally includes the same number of peaks as inner ring 384. For example, inner ring 384 generally includes eight major petals or peaks 396 extending toward and surrounding a central branch opening 397 and eight minor peaks 398 extending and alternating between major peaks 396. Minor peaks 398 extend to a lesser extent toward central branch opening 397. In operation, the intersection of outer connectors 392 with transition members 390 form a pivot point about which major petals 396 may unfold or pivot outward into the side branch vessel. In a preferred embodiment, the inner and outer connectors pivot together such that the major petals 396 open like a flower. Also, the minor peaks 398 of inner ring 384 may undergo deformation and expand when major petals pivot outward into the side branch vessel. In this regard, the geometry of inner ring 384 may permit and/or facilitate different type of expansion characteristics of the branch portion 30 and may also provide for varying degrees of coverage or radial support of the side branch vessel wall upon installation into a side branch vessel. In alternate embodiments, other geometries of inner ring 384 may be used.

Figure 48A:
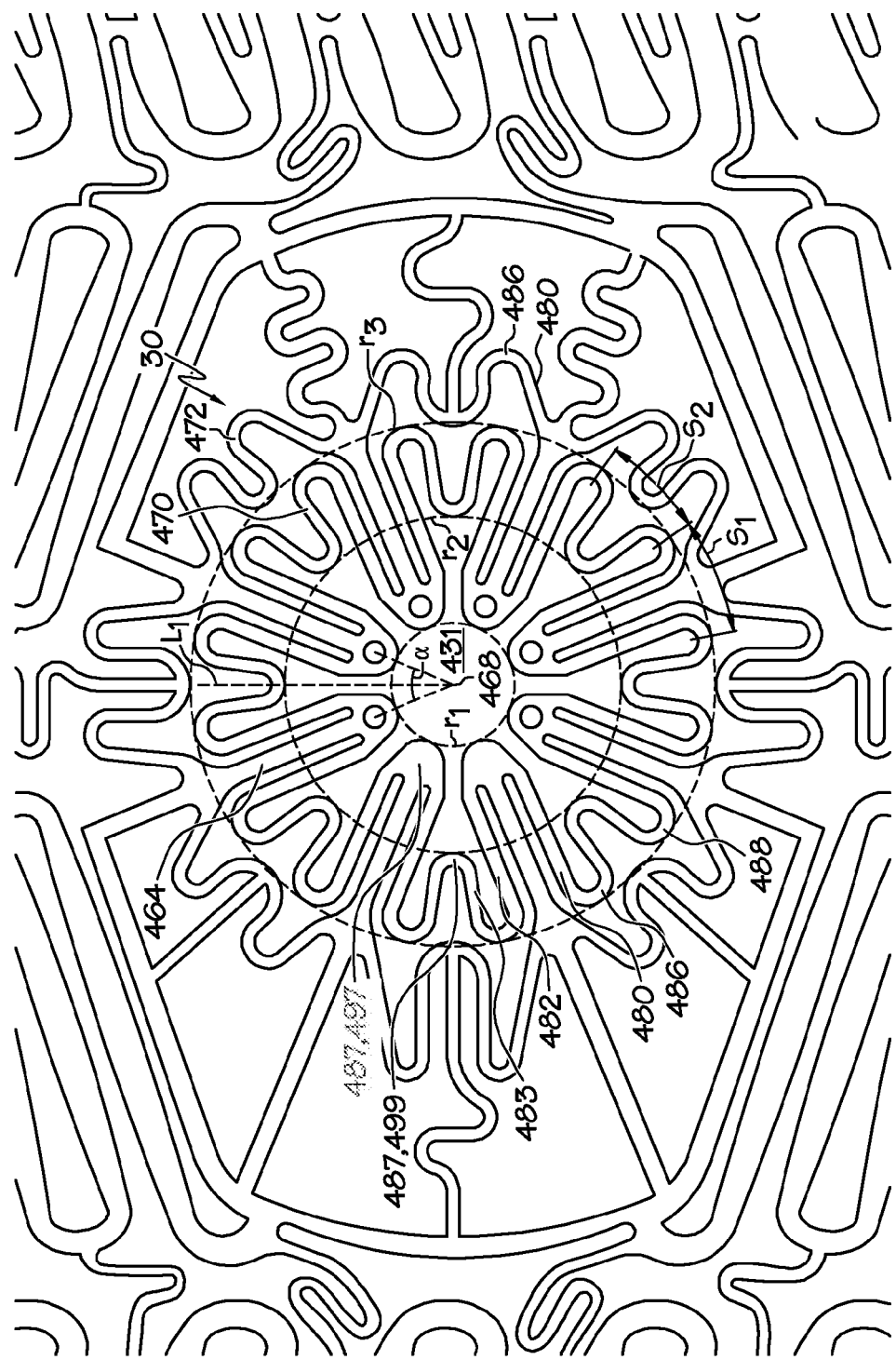
FIG. 48A shows a detail of a portion of FIG. 48.

FIG. 48A shows the branch portion 30 from the embodiment of FIG. 48 in greater detail.

In some embodiments, a branch portion 30 comprises a first serpentine ring 470, a second serpentine ring 472 and a plurality of inner connectors 464. Each serpentine ring 470, 472 is centered upon a side branch center point 468. Each serpentine ring 470, 472 comprises a plurality of alternating struts 480 and turns 486.

The first serpentine ring 470 extends around and defines an inner side branch cell 431. The inner side branch cell 431 is shaped differently from all other cells of the stent. The side branch center point 468 comprises the center of the inner side branch cell 431.

The struts 480 of the first serpentine ring 470 comprise first inner struts 482 and second inner struts 483. The first inner struts 482 are longer than the second inner struts 483. In some embodiments, each first inner strut 482 has the same length, and each second inner strut 483 has the same length.

The struts 480 of the first serpentine ring 470 are arranged in a repeating pattern of two adjacent first inner struts 482 and then two adjacent second inner struts 483. The repeating pattern is encountered as the first serpentine ring 470 is traversed around its periphery. Thus, a reference circle that intersects all of the struts 480 of the first serpentine ring 470 would intersect the struts 480 in a repeating pattern of a first inner strut 482, another first inner strut 482, a second inner strut 483, another second inner strut 483, a first inner strut 482, another first inner strut 482, a second inner strut 483, another second inner strut 483, etc.

The turns 486 of the first serpentine ring 470 comprise alternating inner turns 487 and outer turns 488. Turns 486 that point inward with respect to the side branch, for example pointing toward the side branch center point 468, comprise inner turns 487. Turns 486 that point outward with respect to the side branch, for example pointing away from the side branch center point 468, comprise outer turns 488. Thus, in at least one embodiment, the turns 486 located on either side of an inner turn 487 comprise outer turns 488, and the turns 486 located on either side of an outer turn 488 comprise inner turns 487.

The inner turns 487 further comprise alternating first inner turns 497 and second inner turns 499. Thus, in at least one embodiment, the inner turns 487 located on either side of a first inner turn 497 comprise second inner turns 499, and the inner turns 487 located on either side of a second inner turn 499 comprise first inner turns 497. The first inner turns 497 are located closer to the side branch center point 468 than the second inner turns 499.

In some embodiments, the first inner turns 497 are each located an equal distance away from the side branch center point 468, and thus can be considered aligned around a first reference circle $r_1$ centered upon the side branch center point 468. The first inner turns 497 are also equally distributed around the circumference of the first reference circle $r_1$. In some embodiments, the first inner turns 497 span a greater distance than the second inner turns 499, wherein the ends of the first inner turns 497 are farther away from one another than the ends of the second inner turns 499.

The second inner turns 499 are each located an equal distance away from the side branch center point 468, and thus can be considered aligned around a second reference circle $r_2$ centered upon the side branch center point 468. The second inner turns 499 are equally distributed around the circumference of the second reference circle $r_2$. The second reference circle $r_2$ comprises a larger radius than the first reference circle $r_1$. The first inner turns 497 and the second inner turns 499 are collectively equally spaced around the side branch center point 468. Thus, a reference line 11 oriented in a side branch radial direction that bisects a second inner turn 499 will bisect the angle a between two first inner turns 497. Similarly, a line that bisects a first inner turn 497 will bisect an angle formed between the two second inner turns 499 located on either side of the first inner turn 497.

Each first inner strut 482 is connected at an inner end to a first inner turn 497 and is connected at an outer end to an outer turn 488. Each second inner strut 483 is connected at an inner end to a second inner turn 499 and is connected at an outer end to an outer turn 488.

The outer turns 488 are each located an equal distance away from the side branch center point 468, and thus can be considered aligned around a third reference circle $r_3$ centered upon the side branch center point 468. Adjacent outer turns 488 are spaced around the third reference circle $r_3$ at alternating first spacing $s_1$ and second spacing $s_2$ intervals. Each outer turn 488 is adjacent to two other outer turns 88, one located on a first side (e.g. clockwise around the third reference circle $r_3$) and the other located on the other side (e.g. counter clockwise around the third reference circle $r_3$). The outer turn 488 will be separated from one adjacent outer turn 488 by the first spacing $s_1$ and will be separated from the other adjacent outer turn 488 by the second spacing $s_2$. Adjacent outer turns 488 that are located on opposite sides of a first inner turn 497 are separated by the first spacing $s_1$. Adjacent outer turns 488 that are located on opposite sides of a second inner turn 499 are separated by the second spacing $s_2$. In some embodiments, the second spacing $s_2$ is greater than the first spacing $s_1$.

In some embodiments, an inner connector 464 is straight along its length and is oriented in a side branch radial direction. Thus, an axis of an inner connector 464 can pass through the side branch center point 468. In some embodiments, one inner connector 464 and another inner connector 464 that is located across the inner side branch cell 431 are both oriented upon a common reference line that passes through the side branch center point 468. In some embodiments, all of the inner connectors 464 are evenly distributed around the side branch center point 468.

In some embodiments, each strut 480 of the first side branch ring 470 is parallel to at least one inner connector 464. In some embodiments, an inner connector 464 connects to a first inner turn 497, and the struts 480 that also connect to the first inner turn 497 are parallel to the inner connector 464.

In some embodiments, the first two struts 480 located adjacent to an inner connector 464 in either direction (e.g. a first inner strut 482 and a second inner strut 483) are parallel to the inner connector 464. Thus, the first side branch ring 470 can comprise four adjacent struts 480 that are all parallel to an inner connector 464, wherein some of the struts 480 and the inner connector 464 connect to a common turn 486. The four adjacent struts 480 can comprise two first inner struts 482 and two second inner struts 483. The two first inner struts 482 can comprise mirror images of one another taken across the inner connector 464. The two second inner struts 483 can also comprise mirror images of one another taken across the inner connector 464.

The second side branch ring 472 extends around the first side branch ring 470. In some embodiments, the second side branch ring 472 can comprise the same number of struts 480 and turns 486 as the first side branch ring 470. In some embodiments, the turns 486 of the second side branch ring 472 comprise alternating inner turns 487 and outer turns 488, wherein the inner turns 487 are located closer to the side branch center point 468 than the outer turns 488.

In some embodiments, an inner connector 464 is connected at an inner end to a turn 486 of the first side branch ring 470 and is connected at an outer end to a turn 486 of the second side branch ring 472. In some embodiments, an inner connector 464 spans between a first inner turn 497 of the first side branch ring 470 and an inner turn 487 of the second side branch ring 472.

FIGS. 49-90 each show a flat pattern for another embodiment of a stent 410. Each stent 410 is formed from a plurality of structural framework elements that can define a substantially tubular framework structure that extends around a stent longitudinal axis 411. In some embodiments, a stent 410 comprises a plurality of serpentine bands 420, a side branch structure 460 and a support ring 442 that extends around the side branch structure 460.

A stent 410 further comprises a plurality of cells 430. A cell 430 comprises an opening in the wall portion of the stent 410 oriented between the structural framework elements. The cells 430 of a stent 410 can comprise a variety of shapes and sizes.

A stent 410 can comprise a proximal end 412, a first end region 450, a central region 452, a second end region 454 and a distal end 414. Each region 450, 452, 454 extends across a portion of the length of the stent 410. Each region 450, 452, 454 includes a plurality structural framework elements, for example a plurality of serpentine bands 420. The side branch structure 460 and at least a portion of the support ring 442 are located in the central region 452 of the stent 410. In some embodiments, the support ring 442 extends the entire length of the central region 452.

Each serpentine band 420 extends around at least a portion of a circumference of the stent 410. In some embodiments, a serpentine band 420 comprises a plurality of alternating struts 422 and turns 428. Circumferentially adjacent struts 422 within a serpentine band 420 are connected by a turn 428. Turns 428 that point toward the proximal end 412 of the stent 410 comprise proximal peaks 424, and turns 428 that point toward the distal end 414 of the stent 410 comprise distal valleys 426. The proximal peaks 424 and distal valleys 426 can alternate along the length of the serpentine band 420. Thus, each strut 422 can be connected at one end to a proximal peak 424 and can be connected at the other end to a distal valley 426.

In some embodiments, all of the serpentine bands 420 within a given region 450, 452, 454 are similar in size and shape. In some embodiments, various serpentine bands 420 within a given region 450, 452, 454 may be different in size, shape, strut width, wavelength X, etc. For example, in some embodiments, serpentine bands 420 located in the central region 452 span a greater distance along the length of the stent 410 than serpentine bands 420 located in the end regions 450, 454. In some embodiments, the struts 422 of serpentine bands 420 located in the central region 452 have a greater length than struts 422 located in the end regions 450, 454. In some embodiments, the struts 422 of serpentine bands 420 located in the end regions 450, 454 are wider than struts 422 located in the central region 452. In some embodiments, the wavelength λ of serpentine bands 420 located in the central region 452 is less than the wavelength λ of serpentine bands 420 located in the end regions 450, 454.

In some embodiments, the proximal peaks 424 of a given serpentine band 420 are aligned around a circumference of the stent 410, and can further be equally spaced around the circumference. Similarly, the distal valleys 426 of a given serpentine band 420 can be aligned around another circumference of the stent 410, and can further be equally spaced around the circumference. In some embodiments, various proximal peaks 424 can be longitudinally offset from other proximal peaks 424 within a given serpentine band 420, and various distal valleys 426 can be longitudinally offset from other distal valleys 426 within the band 420.

Each strut 422 comprises a width, which can be measured in a direction normal to the length of the strut 422. In some embodiments, all struts 422 within a given serpentine band 420 have the same width. In some embodiments, the width of various struts 422 within a serpentine band 420 can change. In some embodiments, the width of a strut 422 can change along the length of the strut 422. In some embodiments, the width of struts 422 of one serpentine band 420 can be different from the width of struts 422 of another serpentine band 420.

Each turn 428 has a width, which can be measured in a direction normal to the side of the turn 428 (e.g. normal to a tangent line). In some embodiments, the width of a turn 428 can be greater than the width of one or more struts 422 of the stent 410. In some embodiments, the width of a turn 428 can be less than the width of one or more struts 422 of the stent 410. In some embodiments, the width of a turn 428 varies from one end of the turn 428 to the other. For example, a turn 428 can connect to a strut 422 at one end having the same width as the strut 422. The width of the turn 428 increases, and in some embodiments reaches a maximum at a midpoint of the turn 428. The width of the turn 428 then decreases to the width of another strut 422, which can be connected to the second end of the turn 428.

In some embodiments, serpentine bands 420 that are adjacent to one another along the length of the stent 410 are connected by at least one connector strut 416. Connector struts 416 can connect to any portion of a serpentine band 420, such as a turn 428, or in some embodiments, a strut 422. In some embodiments, a connector strut 16 is linear or straight along its length. In some other embodiments, a connector strut 416 can include curvature along its length, and can further include multiple portions of curvature, for example a convex portion and a concave portion that may be connected at an inflection point.

In some embodiments, a connector strut 416 spans between a proximal peak 424 of one serpentine band 420 and a distal valley 426 of another serpentine band 420.

In some embodiments, connector struts 416 can comprise a first type of connector strut 436 and a second type of connector strut 438. A first connector strut 36 may extend in a first direction. The first connector strut 436 can be oriented at a first angle to the stent lengthwise axis 411. A second connector strut 438 can extend in a second direction that is different from or non-parallel to the first direction, at a second angle to the stent lengthwise axis 411. In some embodiments, the first angle and the second angle can have the same magnitude but different orientations. For example, a first connector strut 436 can form a 70° angle with a stent lengthwise axis 411, while a second connector strut 438 can form a negative 70° angle with the stent lengthwise axis 411. In some embodiments, a first type of connector strut 436 can have a different shape than second type of connector strut 438.

In some embodiments, an area of the stent 410 located between two adjacent serpentine bands 420 can be considered a connector column 444. Each connector column 444 comprises a plurality of connector struts 416. In some embodiments, each connector strut 416 in a connector column 444 can be similar to one another. For example, each connector strut 416 in a first connector column 44a can comprise a first type of connector strut 436. Each connector strut 416 in a second connector column 444b can comprise a second type of connector strut 438.

In some embodiments, first connector columns 444a and second connector columns 444b can alternate along the length of the stent 410. Thus, a serpentine band 420 can be positioned between a first connector column 444a and a second connector column 444b. Accordingly, connector struts 416 that connect to one side of a serpentine band 420 can comprise first connector struts 436, and connector struts 416 that connect to the other side of the serpentine band 420 can comprise second connector struts 438.

Turns 428 can comprise connected turns 458 or unconnected turns 455 depending upon whether the turn 428 connects to a connector strut 416.

In some embodiments, a stent 410 further comprises additional types of connector struts 416. For example, some connector struts 416 that are located in the central region 452 of the stent 410 can comprise sizes and shapes that are different from the sizes and shapes of connector struts 416 located in either end region 450, 454.

In some embodiments, a serpentine band 420 comprises one or more shorter struts 432. A shorter strut 32 is generally shorter than other struts 22 of the serpentine band 20. Shorter struts 32 can be located in proximity to the side branch structure 460, and in some embodiments, a shorter strut 432 can connect to a portion of the side branch structure 460. A serpentine band 420 can also comprise one or more offset turns 434, which can connect to one or more shorter struts 432 and, in some embodiments, can connect to the support ring 442. An offset turn 434 is generally offset from other turns 428 of the serpentine band 420 that face the same direction (e.g. point toward the same direction). For example, most of the distal valleys 426 of a serpentine band 420 may be aligned about a reference circumference of the stent 410, while an offset distal valley 434 located in the same serpentine band 420 is not aligned on the aforementioned reference circumference.

In various embodiments, serpentine bands 420 located in the central region 452 can comprise any suitable combination of struts 422 and turns 428, including struts of varying length, struts having curvature and turns having any suitable location and orientation.

The central region 452 further comprises a side branch structure 460 and a side branch support ring 442. In various embodiments, some or all of the serpentine bands 420 located in the central region 452 extend about a portion of the stent circumference, while the remainder of the circumference is occupied by the side branch structure 460 and the support ring 442.

In some embodiments, serpentine bands 420 located in the central region 452 attach directly to a portion of the support ring 442.

Figure 49:
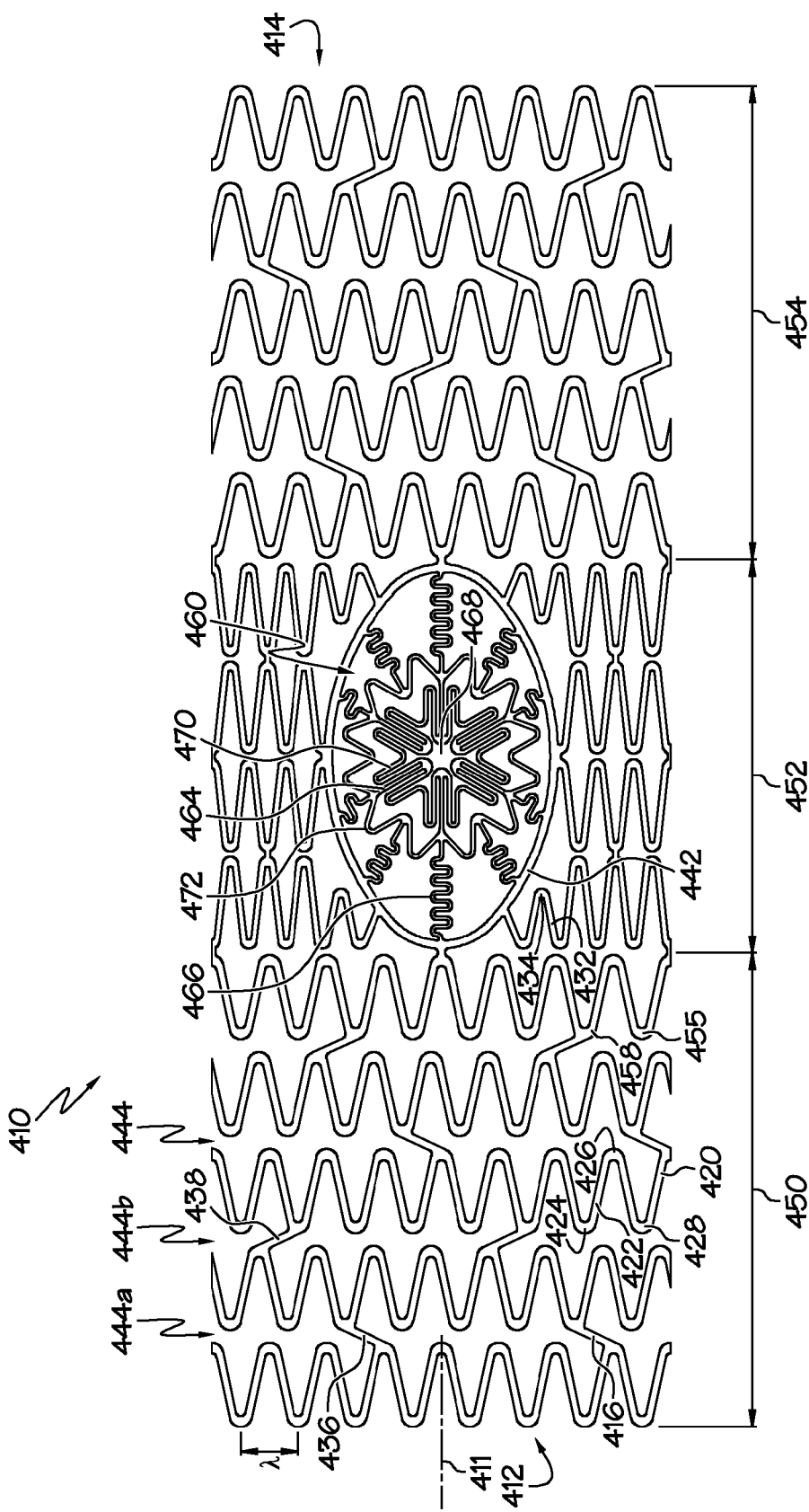
FIGS. 49-90 each show a flat pattern for another embodiment of a stent.

Referring to FIG. 49, the side branch structure 460 comprises a first serpentine ring 470, a second serpentine ring 472, a plurality of side branch inner connectors 464 and a plurality of side branch outer connectors 466. The second serpentine ring 472 extends around the first serpentine ring 470. Each side branch inner connector 464 connects between the first serpentine ring 470 and the second serpentine ring 472. Each side branch outer connector 466 connects between the second serpentine ring 472 and the support ring 442.

The support ring 442 extends around the side branch structure 460 and provides a more rigid support to the side branch structure 460 than would otherwise be provided by the serpentine bands 420 alone. In some embodiments, the support ring 442 comprises a substantially constant strut width, and in some embodiments, struts of the support ring 442 have a greater width than elements of the serpentine bands 420 or other side branch structure 460.

In some embodiments, the support ring 442 extends continuously around the side branch structure 460 and side branch outer connectors 466. In some embodiments, the support ring 442 comprises a structure that is continuously concave with respect to the side branch center point 468. In some embodiments, the support ring 442 comprises a substantially elliptical shape. Thus, in some embodiments, the support ring 442 does not include any portions of curvature that are convex with respect to the side branch center point 468.

Figure 49A:
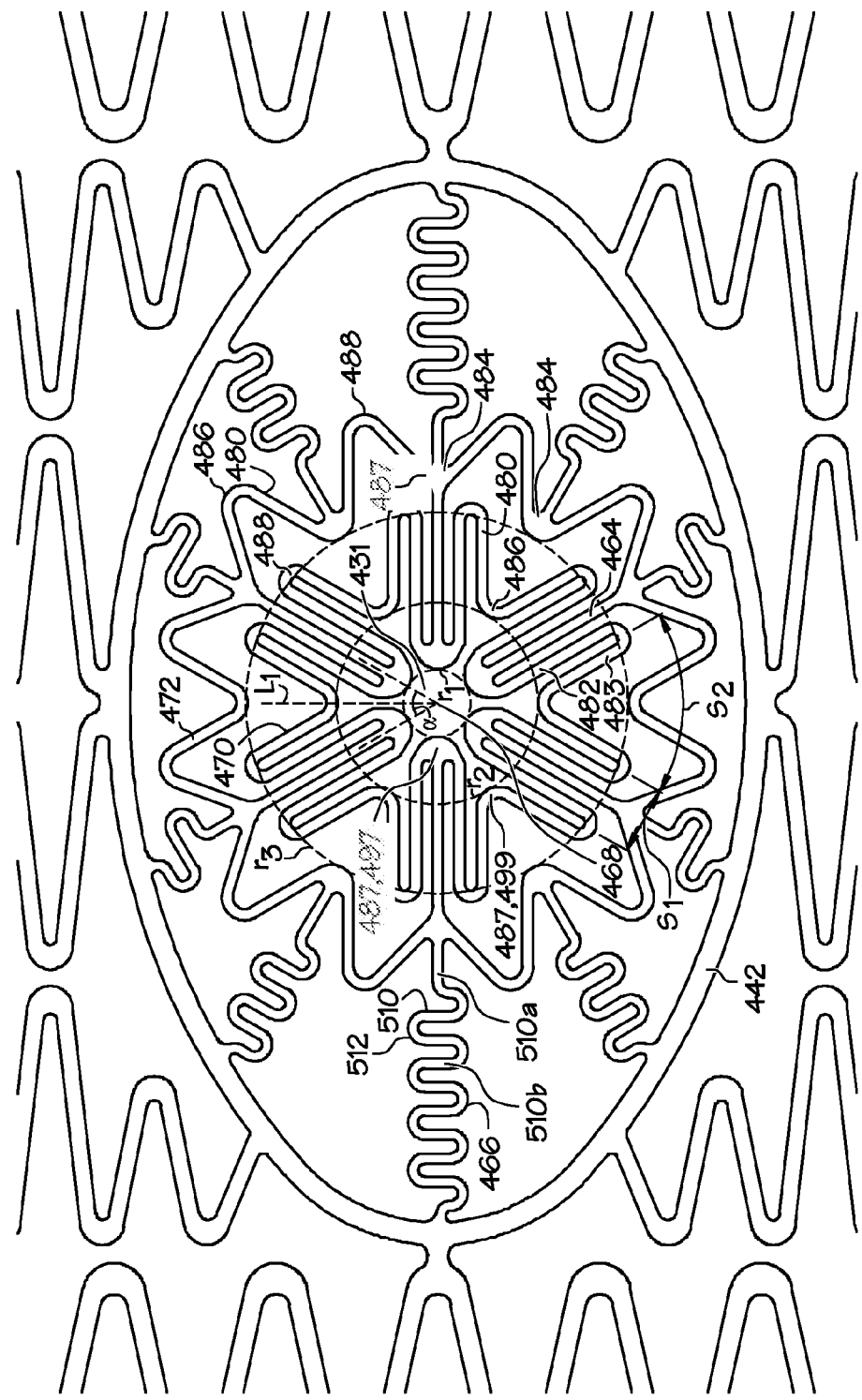
FIG. 49A shows a detail of a portion of FIG. 49.

FIG. 49A shows the side branch structure 460 from the embodiment of FIG. 49 in greater detail. Each serpentine ring 470, 472 is centered upon the side branch center point 468. Each serpentine ring 470, 472 comprises a plurality of alternating struts 480 and turns 486. The serpentine rings 470, 472 are also referred to herein as side branch rings.

The first serpentine ring 470 extends around and defines an inner side branch cell 431. The inner side branch cell 431 is shaped differently from all other cells 430 of the stent 410. The side branch center point 468 comprises the center of the inner side branch cell 431.

The struts 480 of the first serpentine ring 470 comprise first inner struts 482 and second inner struts 483. The first inner struts 482 are longer than the second inner struts 483. In some embodiments, each first inner strut 482 has the same length, and each second inner strut 483 has the same length.

The struts 480 of the first serpentine ring 470 are arranged in a repeating pattern of two adjacent first inner struts 482 and then two adjacent second inner struts 483. The repeating pattern is encountered as the first serpentine ring 470 is traversed around its periphery. Thus, a reference circle that intersects all of the struts 480 of the first serpentine ring 470 would intersect the struts 480 in a repeating pattern of a first inner strut 482, another first inner strut 482, a second inner strut 483, another second inner strut 483, a first inner strut 482, another first inner strut 482, a second inner strut 483, another second inner strut 483, etc.

The turns 486 of the first serpentine ring 470 comprise alternating inner turns 487 and outer turns 488. Turns 486 that point inward with respect to the side branch, for example pointing toward the side branch center point 468, comprise inner turns 487. Turns 486 that point outward with respect to the side branch, for example pointing away from the side branch center point 468, comprise outer turns 488. Thus, in at least one embodiment, the turns 486 located on either side of an inner turn 487 comprise outer turns 488, and the turns 486 located on either side of an outer turn 488 comprise inner turns 487.

The inner turns 487 further comprise alternating first inner turns 497 and second inner turns 499. Thus, in at least one embodiment, the inner turns 487 located on either side of a first inner turn 497 comprise second inner turns 499, and the inner turns 487 located on either side of a second inner turn 499 comprise first inner turns 497. The first inner turns 497 are located closer to the side branch center point 468 than the second inner turns 499.

In some embodiments, the first inner turns 497 are each located an equal distance away from the side branch center point 468, and thus can be considered aligned around a first reference circle $r_1$ centered upon the side branch center point 468. The first inner turns 497 are also equally distributed around the circumference of the first reference circle $r_1$. In some embodiments, the first inner turns 497 span a greater distance than the second inner turns 499, wherein the ends of the first inner turns 497 are farther away from one another than the ends of the second inner turns 499.

The second inner turns 499 are each located an equal distance away from the side branch center point 468, and thus can be considered aligned around a second reference circle $r_2$ centered upon the side branch center point 468. The second inner turns 499 are equally distributed around the circumference of the second reference circle $r_2$. The second reference circle $r_2$ comprises a larger radius than the first reference circle $r_1$. The first inner turns 497 and the second inner turns 499 are collectively equally spaced around the side branch center point 468. Thus, a reference line 11 oriented in a side branch radial direction that bisects a second inner turn 499 will bisect the angle a between two first inner turns 497. Similarly, a line that bisects a first inner turn 497 will bisect an angle formed between the two second inner turns 499 located on either side of the first inner turn 497.

Each first inner strut 482 is connected at an inner end to a first inner turn 497 and is connected at an outer end to an outer turn 488. Each second inner strut 483 is connected at an inner end to a second inner turn 499 and is connected at an outer end to an outer turn 488.

The outer turns 488 are each located an equal distance away from the side branch center point 468, and thus can be considered aligned around a third reference circle $r_3$ centered upon the side branch center point 468. Adjacent outer turns 488 are spaced around the third reference circle $r_3$ at alternating first spacing $s_1$ and second spacing $s_2$ intervals. Each outer turn 488 is adjacent to two other outer turns 88, one located on a first side (e.g. clockwise around the third reference circle $r_3$) and the other located on the other side (e.g. counter clockwise around the third reference circle $r_3$). The outer turn 488 will be separated from one adjacent outer turn 488 by the first spacing $s_1$ and will be separated from the other adjacent outer turn 488 by the second spacing $s_2$. Adjacent outer turns 488 that are located on opposite sides of a first inner turn 497 are separated by the first spacing $s_1$. Adjacent outer turns 488 that are located on opposite sides of a second inner turn 499 are separated by the second spacing $s_2$. In some embodiments, the second spacing $s_2$ is greater than the first spacing $s_1$.

In some embodiments, an inner connector 464 is straight along its length and is oriented in a side branch radial direction Thus, an axis of an inner connector 464 can pass through the side branch center point 468. In some embodiments, one inner connector 464 and another inner connector 464 that is located across the inner side branch cell 431 are both oriented upon a common reference line that passes through the side branch center point 468. In some embodiments, all of the inner connectors 464 are evenly distributed around the side branch center point 468.

In some embodiments, each strut 480 of the first side branch ring 470 is parallel to at least one inner connector 464. In some embodiments, an inner connector 464 connects to a first inner turn 497, and the struts 480 that also connect to the first inner turn 497 are parallel to the inner connector 464.

In some embodiments, the first two struts 480 located adjacent to an inner connector 464 in either direction (e.g. a first inner strut 482 and a second inner strut 483) are parallel to the inner connector 464. Thus, the first side branch ring 470 can comprise four adjacent struts 480 that are all parallel to an inner connector 464, wherein some of the struts 480 and the inner connector 464 connect to a common turn 486. The four adjacent struts 480 can comprise two first inner struts 482 and two second inner struts 483. The two first inner struts 482 can comprise mirror images of one another taken across the inner connector 464. The two second inner struts 483 can also comprise mirror images of one another taken across the inner connector 464.

The second side branch ring 472 extends around the first side branch ring 470. In some embodiments, the second side branch ring 472 can comprise the same number of struts 480 and turns 486 as the first side branch ring 470. In some embodiments, the turns 486 of the second side branch ring 472 comprise alternating inner turns 487 and outer turns 488, wherein the inner turns 487 are located closer to the side branch center point 468 than the outer turns 488.

In some embodiments, an inner connector 464 is connected at an inner end to a turn 486 of the first side branch ring 470 and is connected at an outer end to a turn 486 of the second side branch ring 472. In some embodiments, an inner connector 464 spans between a first inner turn 497 of the first side branch ring 470 and an inner turn 487 of the second side branch ring 472.

In some embodiments, the side branch structure 60 further comprises a junction area 484 where a side branch connector 464, 466 connects to a turn 486. The junction area 484 comprises additional stent material connected to the turn 486 and/or to the side branch connector 464, 466 that provides a greater scaffolding than would be provided by a turn 486 of constant width connected to a side branch connector 464, 466 of constant width.

In some embodiments, each outer connector 466 connects between the second serpentine ring 472 and the support ring 442. In some embodiments, each outer connector 466 connects between an inner turn 487 and the support ring 442.

In some embodiments, each outer connector 466 comprises struts 510 and turns 512. Some outer connectors 466 can comprise more struts 510 and turns 512 than other outer connectors 466. In some embodiments, an outer connector 466 can comprise at least one strut 510a oriented in a side branch radial direction, and at least one strut 510b oriented perpendicular to a side branch radial direction. In some embodiments, an outer connector 466 can include a plurality of struts 510b that are oriented perpendicular to a side branch radial direction.

Figure 50:
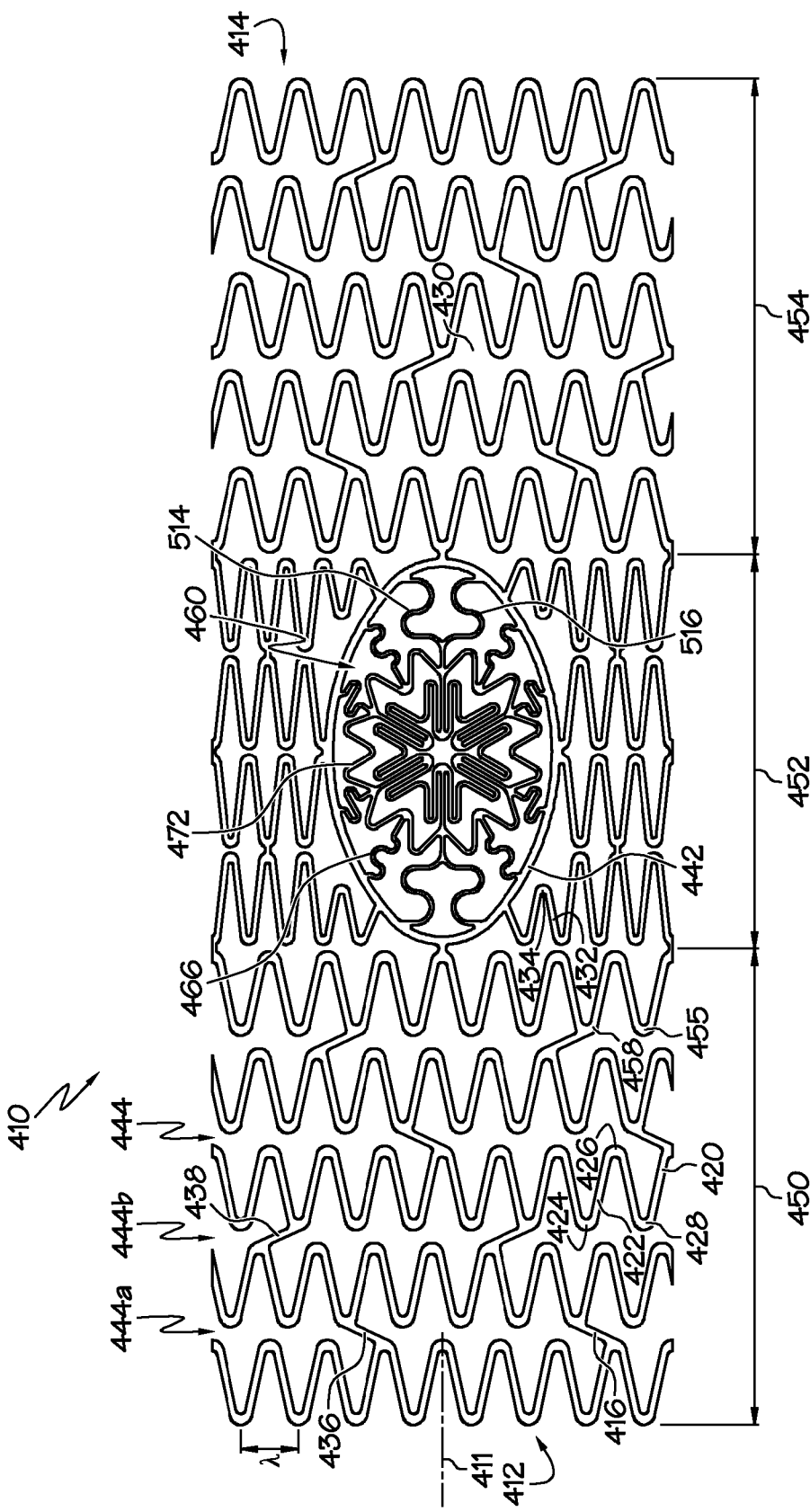

FIG. 50 shows a flat pattern for another embodiment of a stent 410. FIG. 50 shows further embodiments of outer side branch connectors 466.

In some embodiments, a side branch outer connector 466 can connect to a side branch ring 472 at one end and can split into a first portion 514 and a second portion 516. Each portion 514, 516 can attach to the support ring 442. The first portion 514 can comprise a mirror image of the second portion 516 taken across a side branch axis that is parallel to the stent longitudinal axis 411.

Figure 51:
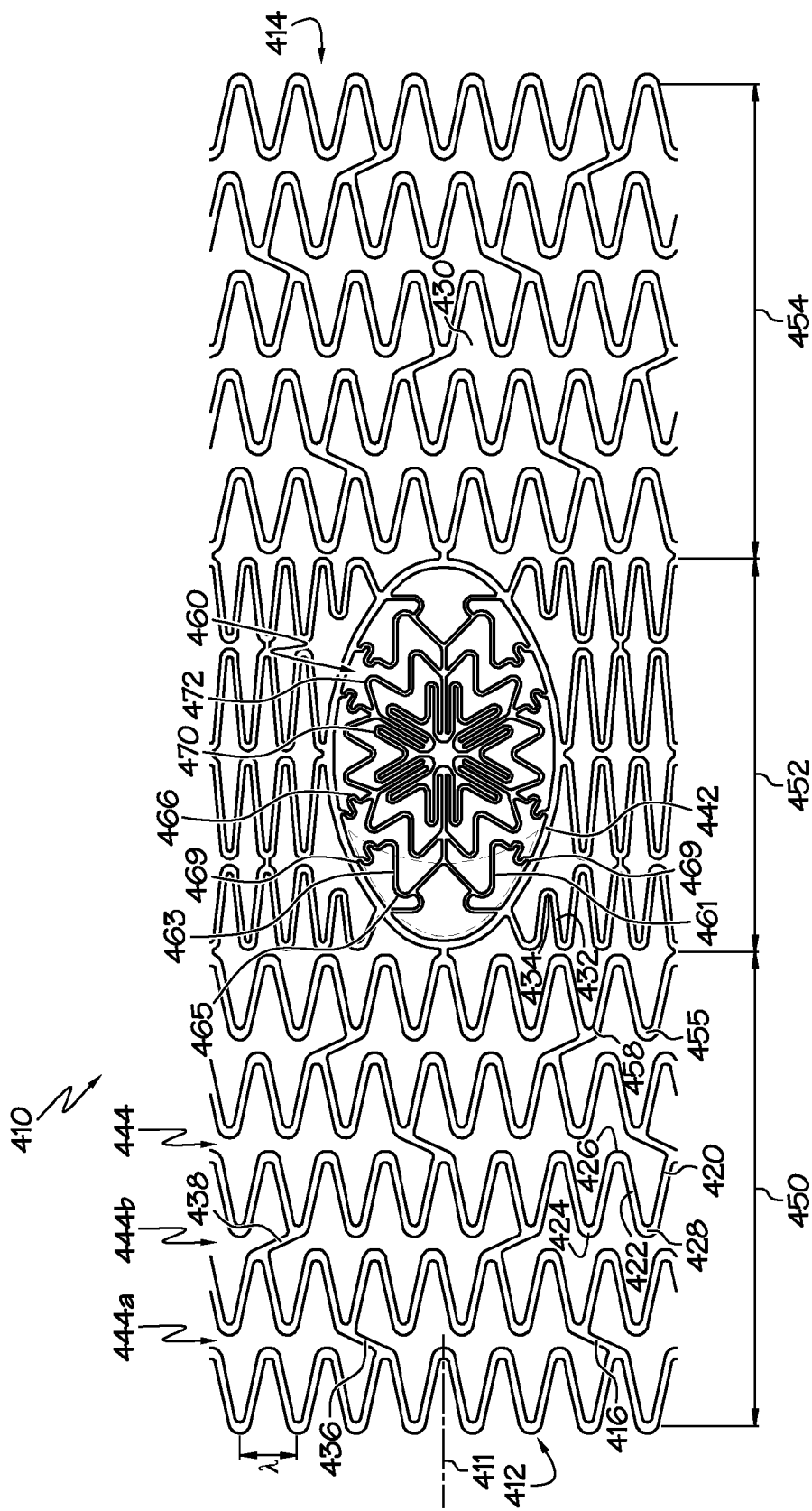

FIG. 51 shows a flat pattern for another embodiment of a stent 410. The stent 410 further comprises an ancillary side branch structure 461. In some embodiments, the ancillary side branch structure 61 can be considered a part of the side branch structure 60. In some embodiments, the ancillary side branch structure 461 can comprise various embodiments of outer side branch connectors 466. In some embodiments, the ancillary side branch structure 461 can be considered any stent structure located within an ancillary side branch area 520. The ancillary side branch area 520 comprises area located within the support ring 442 that is adjacent to the side branch rings (e.g. 472).

The ancillary side branch structure 461 comprises additional stent structure adjacent to the side branch rings 470, 472 that is located within the support ring 442. The ancillary side branch structure 461 can have any suitable configuration of stent elements, and in some embodiments comprises a plurality of ancillary struts 463 and a plurality of ancillary turns 465. Various embodiments of ancillary turns 465 can span differing distances, can comprise different arc lengths and can have different radii of curvature. A plurality of the ancillary struts 463 can be oriented parallel to a longitudinal axis 411. A plurality of the ancillary struts 463 can be oriented parallel to an inner connector 464 or at least a portion of an outer connector 466.

In some embodiments, circumferentially opposed outer ends 469 of an ancillary side branch structure 461 can connect to the support ring 442.

Figure 52:
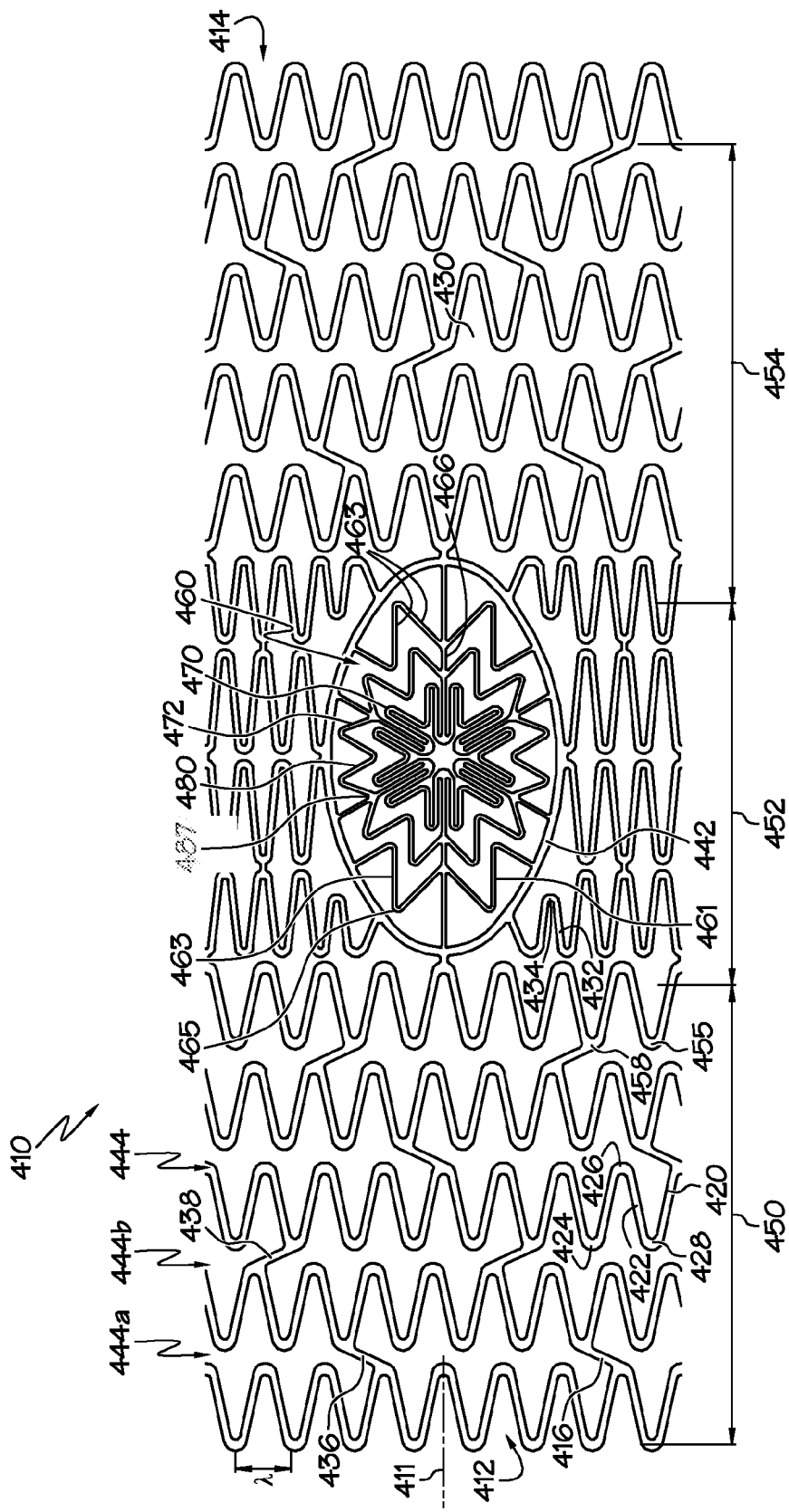

FIG. 52 shows a flat pattern for another embodiment of a stent 410 comprising an ancillary side branch structure 461. Each ancillary side branch strut 463 is parallel to a plurality of struts 480 of the first serpentine ring 470 and also parallel to a plurality of struts 480 of the second serpentine ring 472.

Each outer side branch connector 466 is connected at one end to the second side branch ring 472. Each outer side branch connector 466 is connected at the other end to either the support ring 442 or to the ancillary side branch structure 461.

In some embodiments, every other inner turn 487 of the second side branch ring 472 is connected to an outer side branch connector 466, and every other inner turn 487 of the second side branch ring 472 is not connected to any side branch connectors 464, 466.

Figure 53:
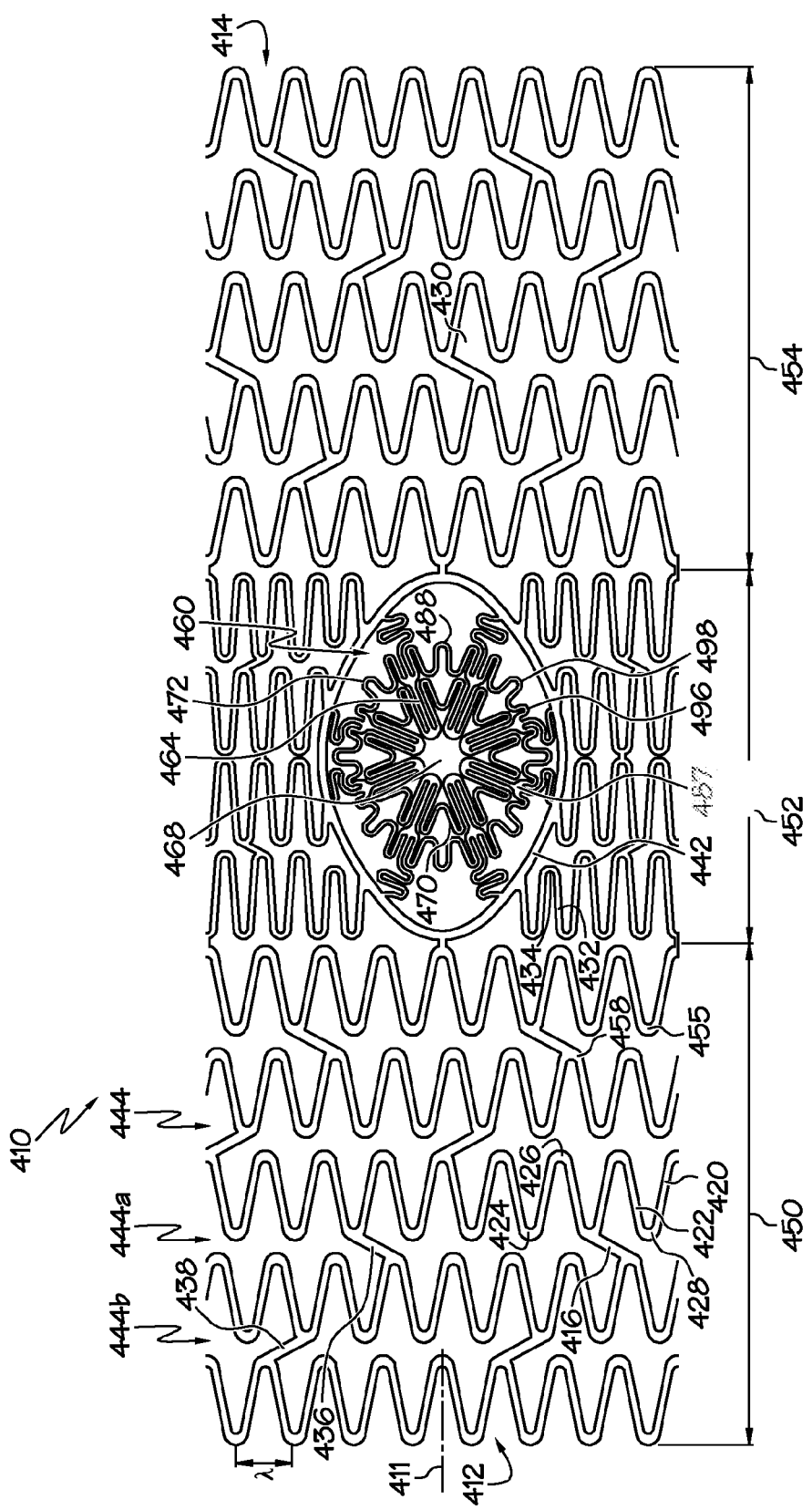

FIG. 53 shows a flat pattern for another embodiment of a stent 410, wherein the second serpentine ring 472 comprises more struts 480 and more turns 486 than the first side branch ring 470.

The outer turns 488 of the second serpentine ring 472 can further comprise first outer turns 496 and second outer turns 498, wherein the first outer turns 496 are located closer to the side branch center point 468 than the second outer turns 498. Various embodiments of turns 486 of the second side branch ring 472 can span differing distances, can comprise different arc lengths and can have different radii of curvature.

An inner turn 487 of the second side branch ring 472 that connects to an inner connector 464 can be different from other inner turns 487 of the second side branch ring 472. For example, an inner turn 487 that connects to an inner connector 464 can span a greater distance than other inner turns 487. An inner turn 487 of the second side branch ring 472 that connects to an inner connector 464 can span the same distance and have the same curvature as a first inner turn 497 of the first side branch ring 470.

Figure 54:
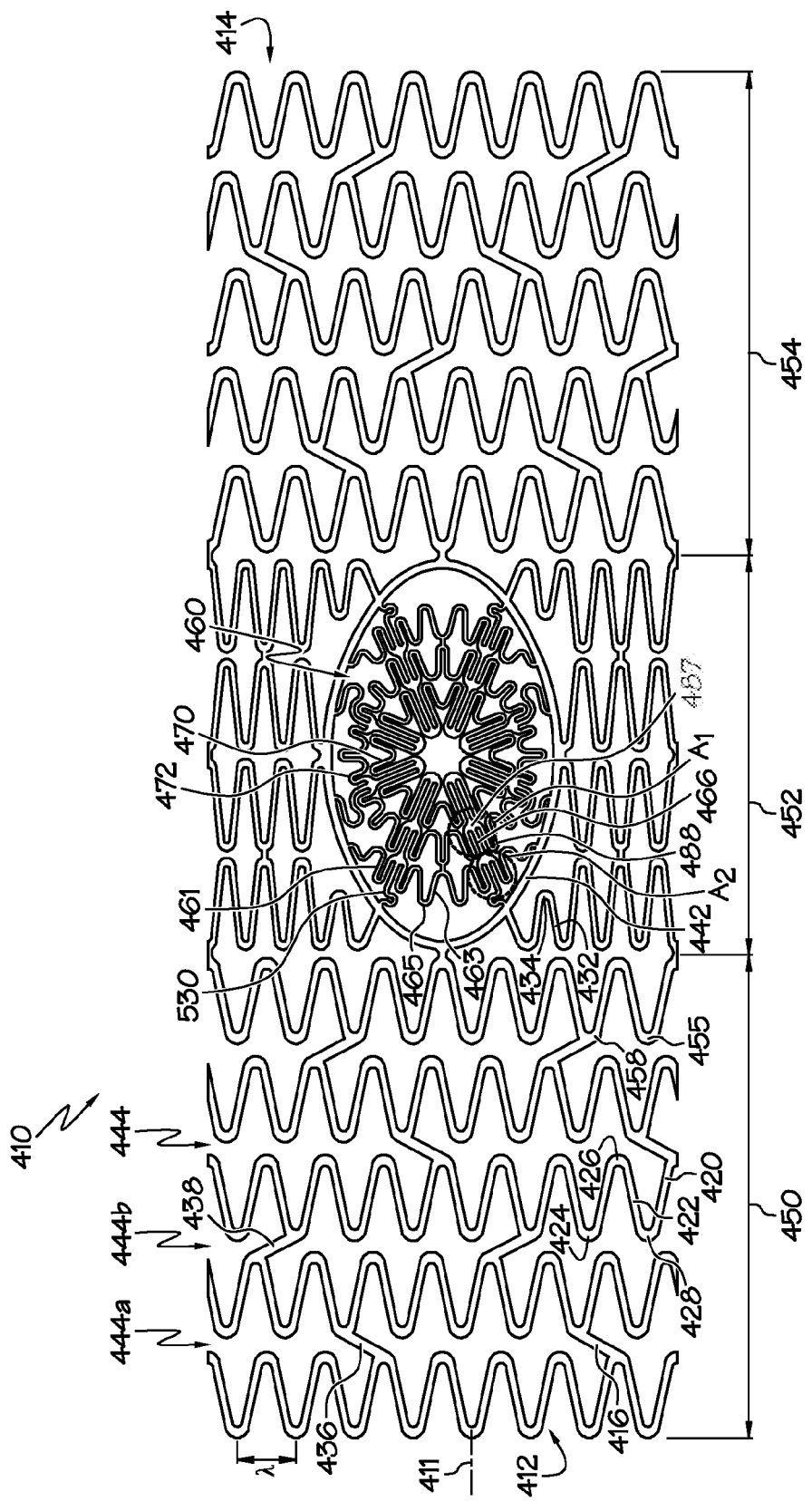

FIG. 54 shows a flat pattern for another embodiment of a stent 410 comprising an ancillary side branch structure 461.

In some embodiments, the ancillary side branch structure 461 comprises struts 463 and turns 465 that mimic the configuration of other portions of the side branch structure 460. For example, area $A_1$ of FIG. 54 includes an inner turn 487, two outer turns 488 and a plurality of struts 480 of the second side branch ring 472. Area $A_1$ also includes a side branch outer connector 466. Area $A_2$ includes struts 463 and turns 465 of the ancillary side branch structure 461. The struts 463 of the ancillary side branch structure 461 in area $A_2$ are parallel to the struts 480 of the second side branch ring 472 in area $A_1$. The turns 465 of the ancillary side branch structure 461 in area $A_2$ are similar to the turns 487, 488 of the second side branch ring 472 in area $A_1$.

The stent 410 further comprises a plurality of ancillary side branch connectors 530 that connect between the ancillary side branch structure 461 and the support ring 442.

The ancillary side branch connector 530 in area $A_2$ comprises a straight portion that is parallel to the side branch outer connector 466 included in area $A_1$.

Figure 55:
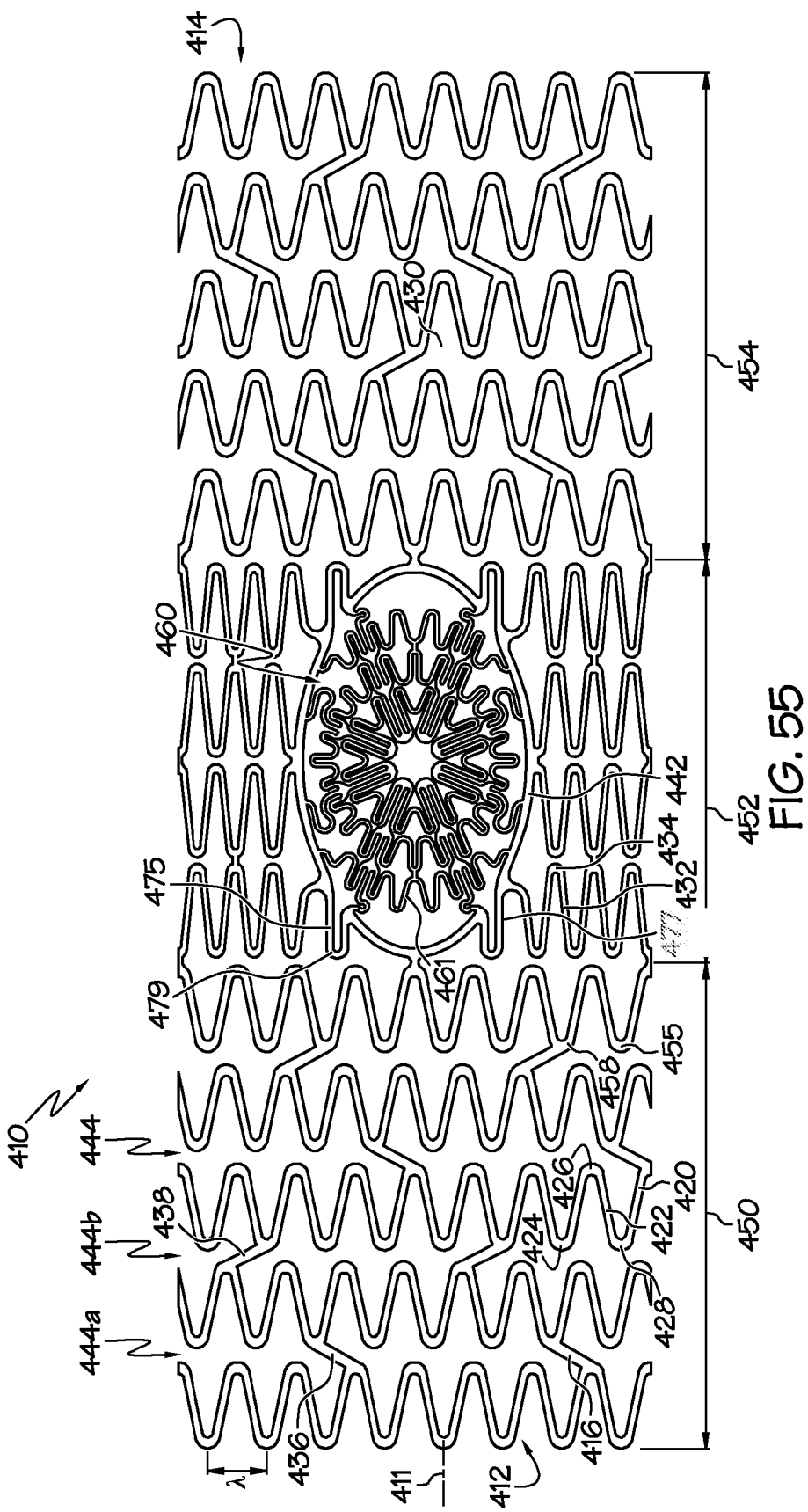

FIG. 55 shows a flat pattern for another embodiment of a stent 410 comprising an ancillary side branch structure 461. The stent 410 further comprises a support ring 442 having a plurality of loop portions 477.

The support ring 442 extends continuously around the side branch structure 460 and the ancillary side branch structure 461. In some embodiments, each loop portion 477 comprises a loop turn 479 and a plurality of loop struts 475. In some embodiments, a loop strut 475 is straight and is oriented parallel to the stent longitudinal axis. In some embodiments, a loop turn 479 is oriented with a peak (e.g. a maximum or minimum) pointed in a stent longitudinal direction. This configuration of loop portions 477 allows the support ring 442 to expand in the stent circumferential direction with lessened longitudinal shortening of the support ring 442 than if the support ring 442 did not include loop portions 477. This configuration can also help to provide apposition between the support ring 442 and areas of a vessel bifurcation, such as an elliptical intersection ring between a primary vessel and a branch vessel, while the support ring 442 remains within the primary vessel.

In some embodiments, one loop portion 477 can comprise a mirror image of another loop portion 477 taken across a stent longitudinal axis that intersects the side branch center point 468. A loop portion 477 can also comprise a mirror image of another loop portion 477 taken across an axis oriented in the stent circumferential direction that passes through the side branch center point 468.

Figure 56:
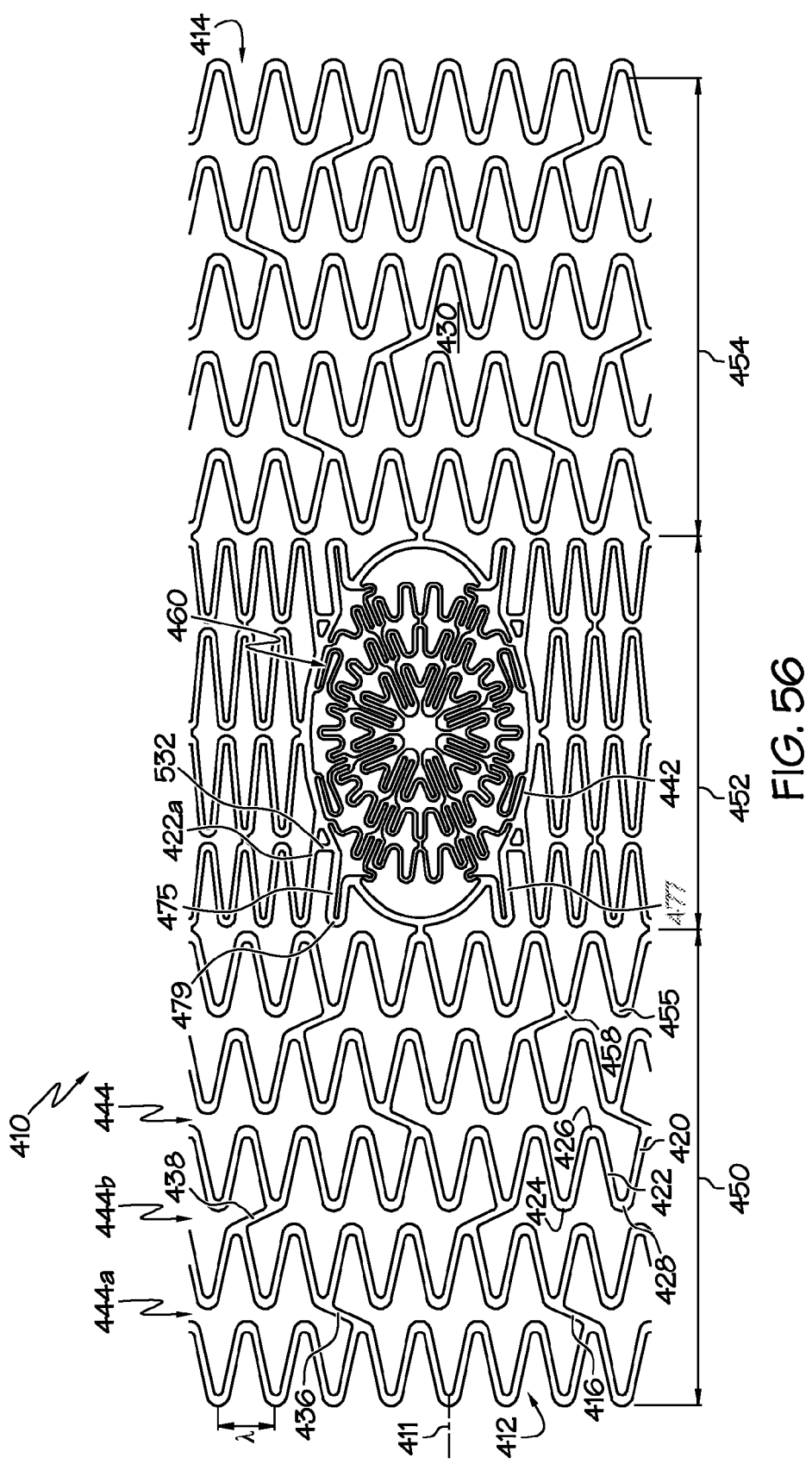

FIG. 56 shows a flat pattern for another embodiment of a stent 410 wherein the support ring 442 comprises a plurality of loop portions 477.

In some embodiments, each loop portion 477 comprises a loop turn 479 and a plurality of loop struts 475. In some embodiments, a loop strut 475 is straight and is oriented non-parallel to the stent longitudinal axis 411. In some embodiments, a loop strut 475 is parallel to a strut 422a of a serpentine band 420 that connects to the support ring 442.

In some embodiments, a strut 422a of a serpentine band 420 that connects to the support ring 442 can be longer than other struts 422 of the serpentine band 420.

In some embodiments, a stent 410 further comprises a stiffening strut 532 that connects between the support ring 442 and the strut 422a of a serpentine band 420 that connects to the support ring 442. In some embodiments, a stiffening strut 532 is oriented in a stent circumferential direction.

Figure 57:
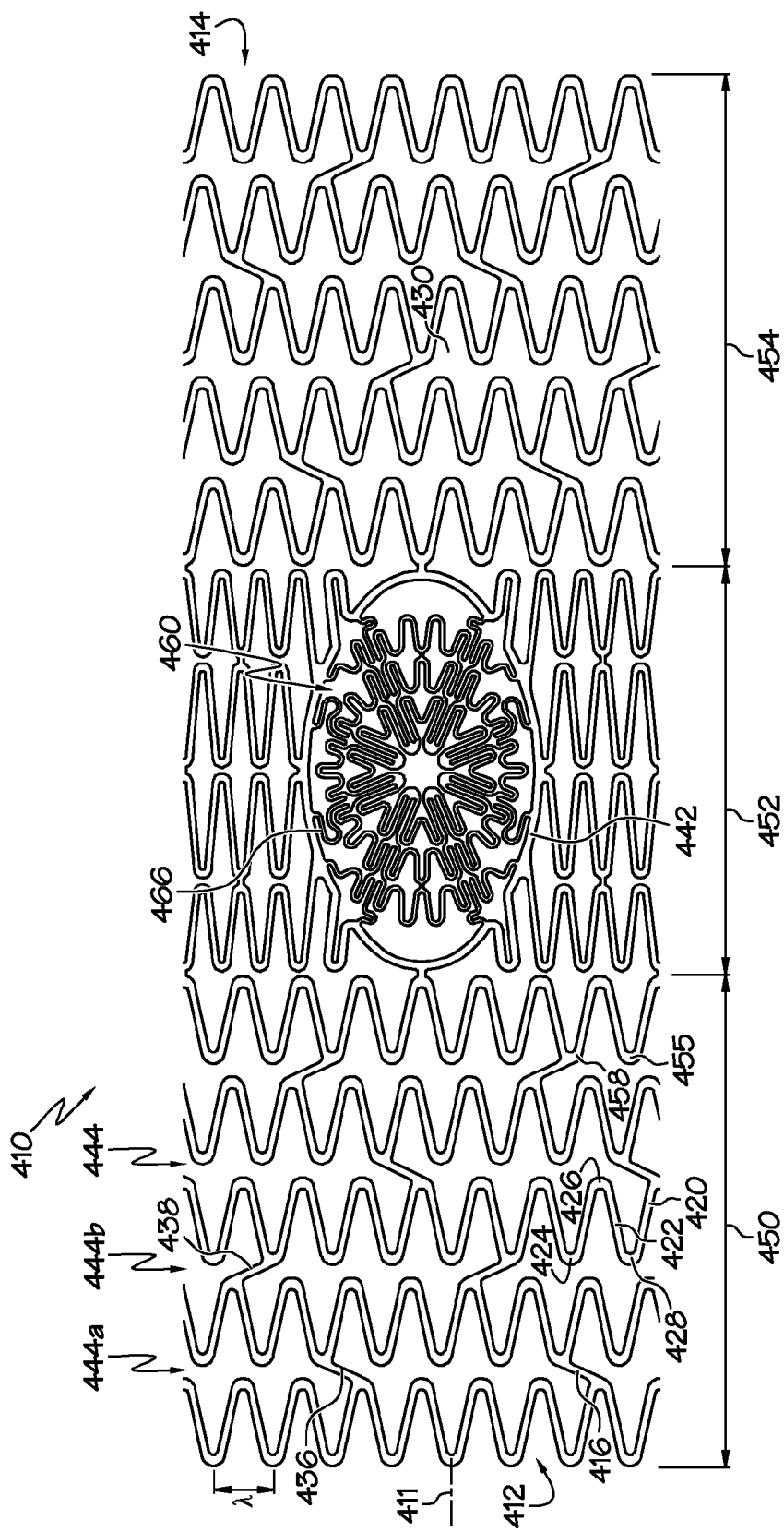

FIG. 57 shows a flat pattern for another embodiment of a stent 410. The pattern is similar to the pattern of FIG. 56 but excludes stiffening struts 532. The pattern of FIG. 57 also comprises outer side branch connectors 466 that are shaped differently from outer side branch connectors 466 of FIG. 56.

Figure 58:
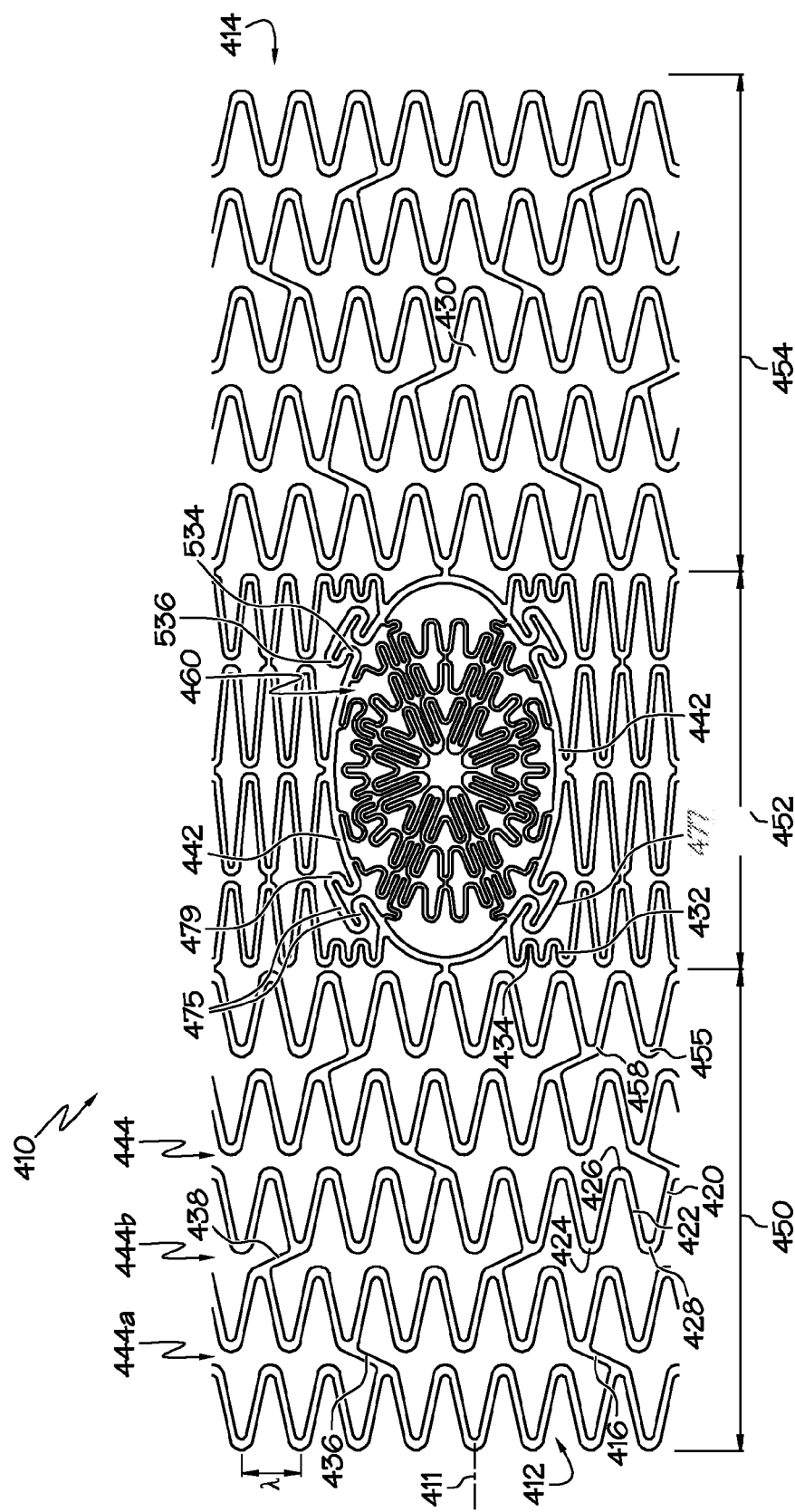

FIG. 58 shows a flat pattern for another embodiment of a stent 410 wherein the support ring 442 comprises a plurality of loop portions 477. In some embodiments, each loop portion 477 comprises a plurality of loop turns 479 and a plurality of loop struts 475.

In some embodiments, a loop strut 475 is oriented substantially parallel to adjacent portions of the support ring 442.

In some embodiments, a loop portion 477 comprises a plurality of first loop turns 534 and a plurality of second loop turns 536, wherein the first loop turns 534 and the second loop turns 536 face opposite directions. In some embodiments, each loop turn 479 extends 180 degrees.

The stent 410 of FIG. 58 further includes serpentine bands 420 that comprise a plurality of shorter struts 432 and a plurality of offset turns 434.

Figure 59:
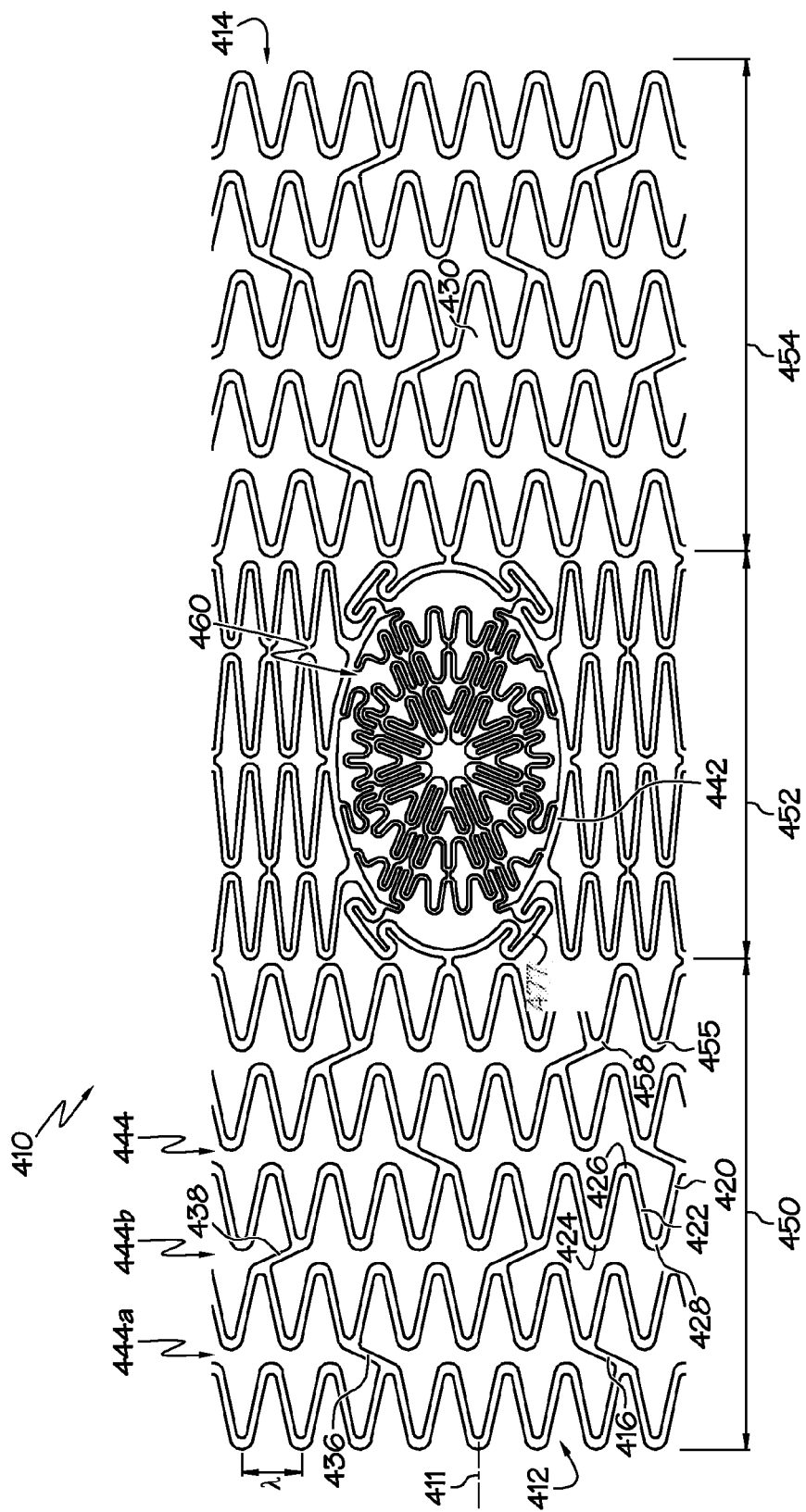

FIG. 59 shows a flat pattern for an embodiment of a stent 410 similar to the pattern of FIG. 58, wherein the support ring 442 comprises a plurality of loop portions 477. However, the serpentine bands 420 located in the central portion 452 of the stent 410 each comprise struts 422 that are the same length as every other strut 422 included in the serpentine band 420.

Figure 60:
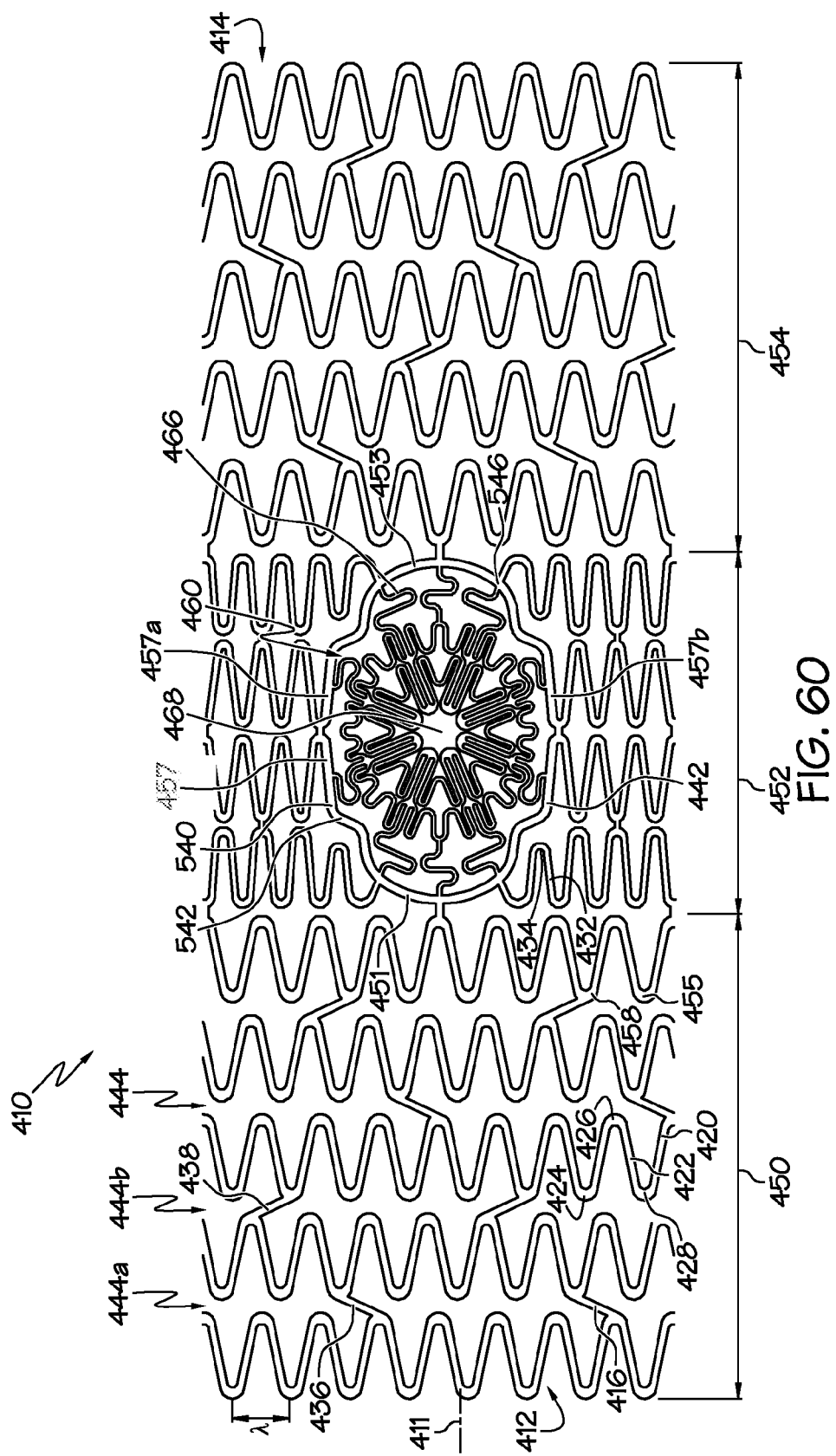

FIG. 60 shows a flat pattern for another embodiment of a stent 410.

In some embodiments, a support ring 442 comprises a plurality of straight struts 540 and curved portions 542. The straight struts 540 and curved portions 542 alternate as the support ring 442 is traversed around its perimeter.

In some embodiments, a curved portion 542 can be convex with respect to the side branch center point 468. In some embodiments, a curved portion 542 can be concave with respect to the side branch center point 468. In some embodiments of a support ring 442, the orientations of adjacent curved portions 542 can alternate between convex and concave as the support ring 442 is traversed around its perimeter.

In some embodiments, the support ring 442 comprises a first portion 451 and a second portion 453. The first portion 451 comprises a mirror image of the second portion 453 taken across a circumference of the stent that intersects the side branch center point 468.

In some embodiments, the support ring 442 comprises at least one continuation strut 457 that comprises a continuation of a serpentine band 420. Thus, the support ring 442 at least partially transitions into the serpentine band 420. A continuation strut 457 is connected at one end to a portion of a serpentine band 420, and is connected at the other end to a portion of the support ring 442, such as a curved portion 542.

Each continuation strut 457 can be substantially straight along its length. In some embodiments, a continuation strut 457 is oriented parallel to a plurality of struts 422 of the serpentine band 420 to which it connects.

In some embodiments, a portion 451, 453 of the support ring 442 comprises a first continuation strut 457a and a second continuation strut 457b. The first continuation strut 457a is parallel to a first plurality of struts 422 of the serpentine band 420. The second continuation strut 457b is parallel to a second plurality of struts 422 of the serpentine band 420. The first continuation strut 257a is further nonparallel to the second continuation strut 257b.

In some embodiments, a continuation strut 457 has a greater width than the struts 422 the serpentine band 420 to which it is attached. In some embodiments, a continuation strut 457 comprises the same width as the rest of the portion 451, 453, or as the rest of the support ring 442.

In some embodiments, a support ring 442 comprises at least one multiple attachment location 546, wherein other stent structure is attached to the support ring 442 on both sides of the multiple attachment location 546. For example, in some embodiments, a side branch outer connector 466 can attach to an inner side of the multiple attachment location 546, and a serpentine band 420 can attach to an outer side of the multiple attachment location 546.

In some embodiments, a curved portion 542 of the support ring 442 comprises at least three multiple attachment locations 546.

Figure 61:
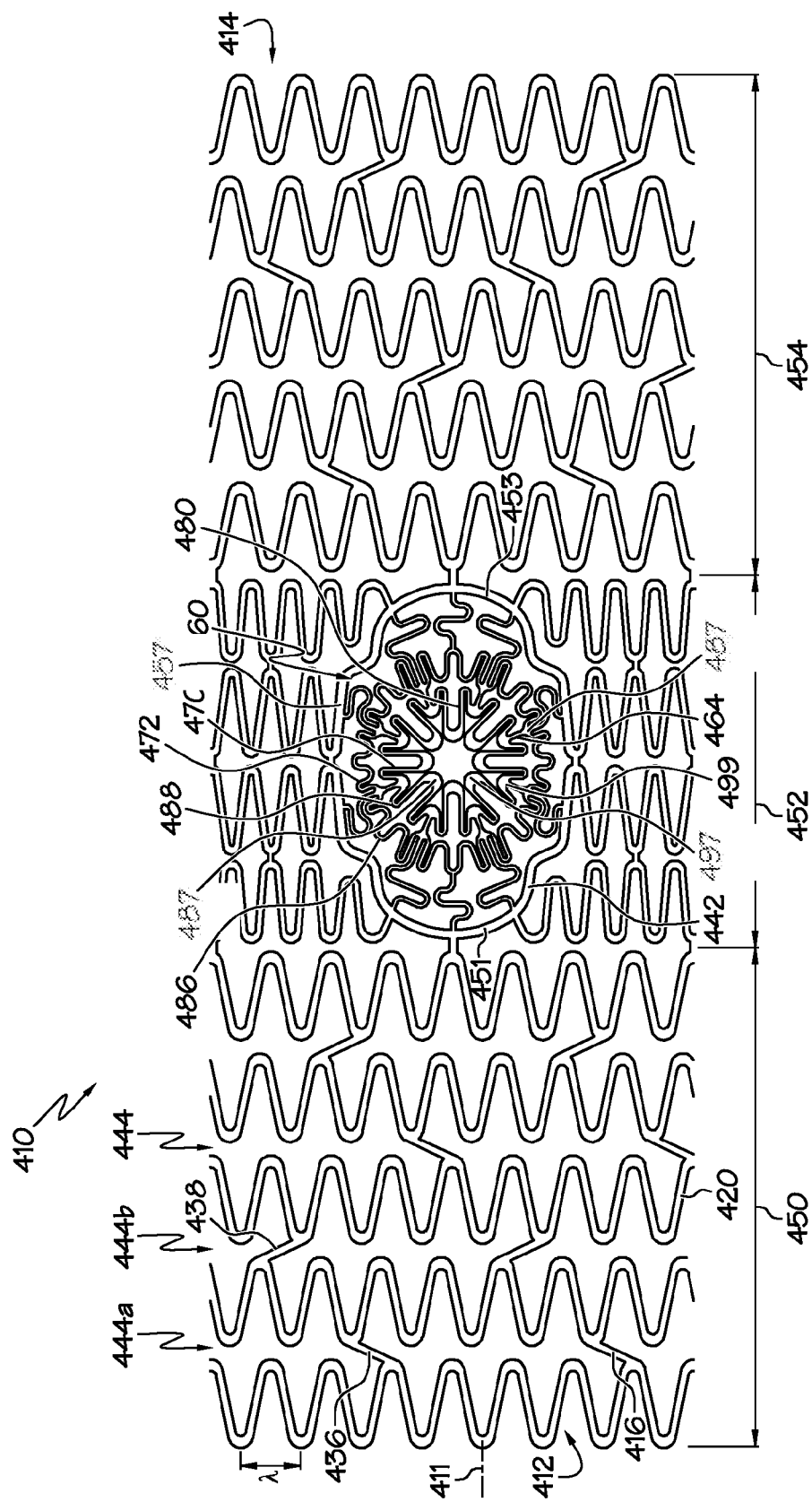

FIG. 61 shows a flat pattern for another embodiment of a stent 410 wherein the support ring 442 is configured similarly to the pattern of FIG. 60.

FIG. 61 shows another embodiment of the side branch structure 460. The turns 486 of the first serpentine ring 470 comprise alternating inner turns 487 and outer turns 488, and the inner turns 487 further comprise alternating first inner turns 497 and second inner turns 499, for example as described with respect to FIG. 49A.

The side branch inner connectors 464 connect between a second inner turn 499 of the first serpentine ring 470 and an inner turn 487 of the second serpentine ring 472.

In some embodiments, the width of an inner turn 487 of the first serpentine ring 470 can be greater than the width of the struts 480 to which the inner turn 487 is connected. In some embodiments, the width of an inner turn 487 of the first serpentine ring 470 is up to four times the width of the struts 480 to which the inner turn 487 is connected.

Figure 62:
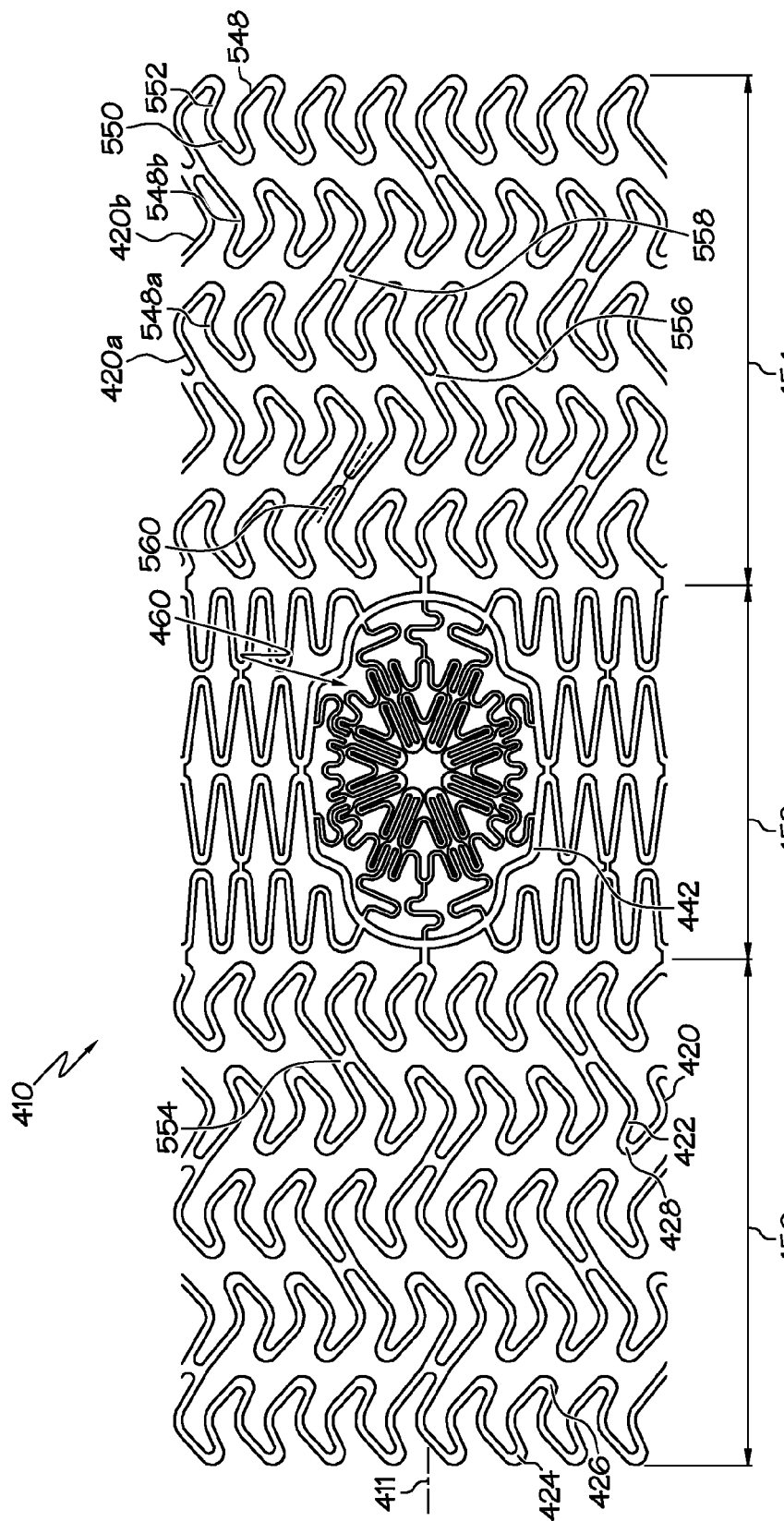

FIG. 62 shows a flat pattern for another embodiment of a stent 410 wherein the support ring 442 is configured similarly to the pattern of FIG. 60.

FIG. 62 shows another embodiment of serpentine bands 420 that are located in either end region 450, 454 of the stent 410.

In some embodiments, the struts 422 of a serpentine band 420 can comprise bent struts 548. Bent struts 548 comprise a first portion 550 and a second portion 552, wherein the first portion 550 is oriented at an angle to the second portion 552.

In some embodiments, adjacent bent struts 548 within a serpentine band 420 are oriented in the same direction such that the adjacent struts 548 will nest or form a nested chevron pattern.

In some embodiments, adjacent serpentine bands 420 comprise bent struts 548 that are oriented in opposite directions. For example, the bent struts 548a of one serpentine band 420a can be oriented in one circumferential direction, and the bent struts 548b of an adjacent serpentine band 420b can be oriented in the opposite circumferential direction.

Adjacent serpentine bands 420 are connected by at least one band connection 554. Band connections 554 can comprise a distal valley 426 of one serpentine band 420 that is attached to a proximal peak 424 of an adjacent serpentine band 420. The distal valley 426 and the proximal peak 424 that comprise the band connection 554 can be offset from other distal valleys 426 or proximal peaks 424 that are included in the same serpentine band 420.

In some embodiments, a band connection 554 comprises an H-shape.

Various struts 422 of a serpentine band 420 can span different distances in the longitudinal direction of the stent 410. Struts 422 that connect to a band connection 554 can be longer than struts 422 that are not connected to a band connection 554.

In some embodiments, the band connections 554 comprise first band connections 556 and second band connections 558. A first band connection 556 can have a first orientation and a second band connection 558 can have a second orientation that is different from the first orientation. For example, a first band connection 556 can have an axis 560 that may comprise a "vertical" axis of the H-shape. The axis 560 can be oriented at a first angle to a stent lengthwise axis 11. An axis 560 of a second band connection 558 can be oriented at a second angle to a stent lengthwise axis 411, the second angle being different than the first angle. In some embodiments, the first angle and the second angle may have the same magnitude but different orientations. For example, an axis 560 of a first band connection 556 can form a 35° angle with a stent lengthwise axis 411, while an axis 560 of a second band connection 558 can form a negative 35° angle with the stent lengthwise axis 411. In some embodiments, a first angle can comprise a mirror image of a second angle across a line parallel to the stent lengthwise axis 411.

Figure 63:
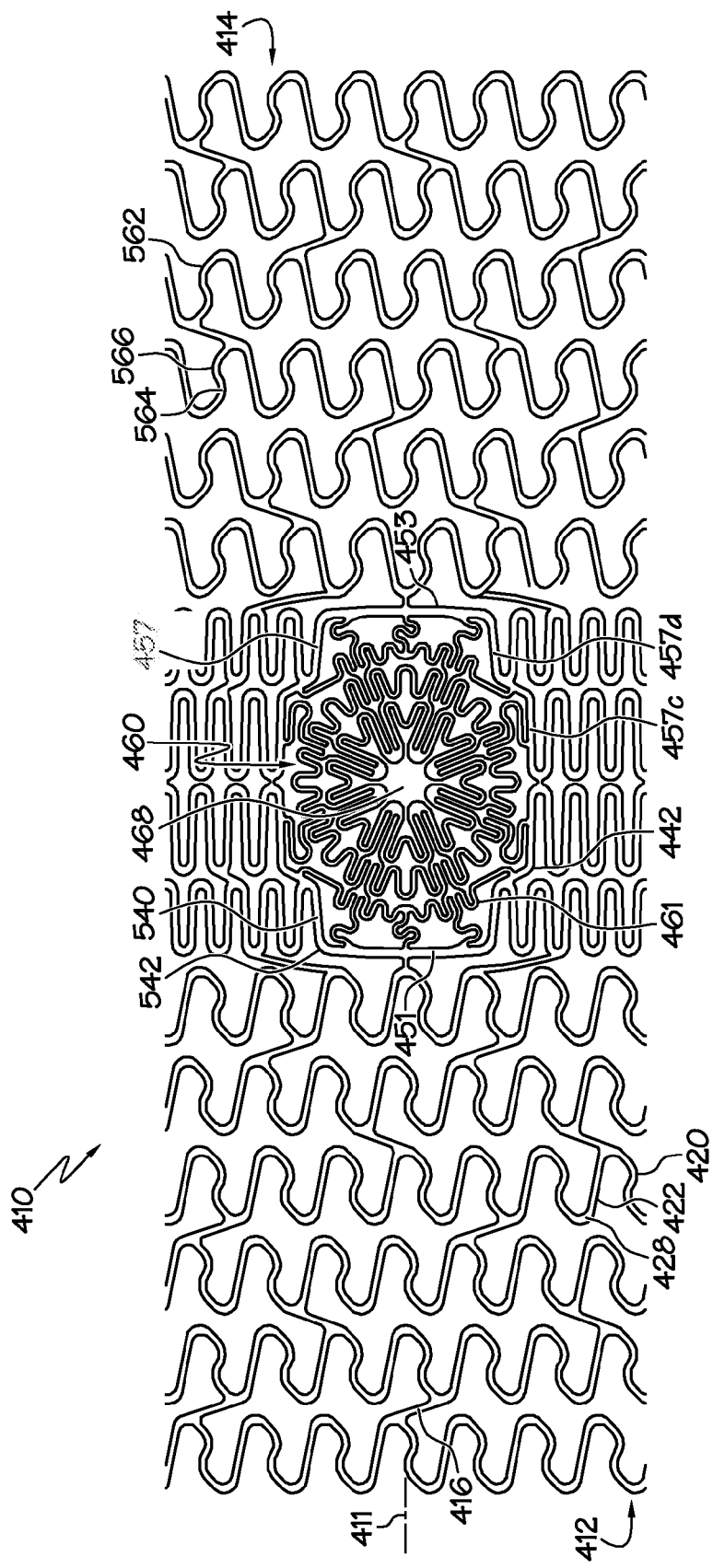

FIG. 63 shows a flat pattern for another embodiment of a stent 410.

In some embodiments, a serpentine band 420 can comprise one or more s-shaped struts 562. In some embodiments, an s-shape comprises a first curved portion 564 and a second curved portion 566. The curvature orientation of the first curved portion 564 is different than the curvature orientation of the second curved portion 566. For example, if the first curved portion 564 can considered convex, the second curved portion 566 can be considered concave. An s-shaped strut 562 can include an inflection point where the curvature changes orientation.

In some embodiments, a serpentine band 20 may comprise alternating straight struts 422 and bent or s-shaped struts 562.

FIG. 63 shows another embodiment of a support ring 442 comprising a plurality of straight struts 540 and curved portions 542. The support ring 442 also comprises a first portion 451 and a second portion 453. The first portion 451 comprises a mirror image of the second portion 453 taken across a circumference of the stent that intersects the side branch center point 468.

In some embodiments, each portion 451, 453 of the support ring 442 comprises a plurality of continuation struts 457 that each comprise a continuation of a serpentine band 420.

In some embodiments, a continuation strut 457 comprises the same width as a strut 422 of the serpentine band 420 to which it connects.

In some embodiments, a portion 451, 453 of the support ring 442 comprises a first continuation strut 457c that connects to one serpentine band 420, and a second continuation strut 457d that connects to another serpentine band 420.

The pattern of FIG. 63 also shows another embodiment of ancillary side branch structure 461.

Figure 64:
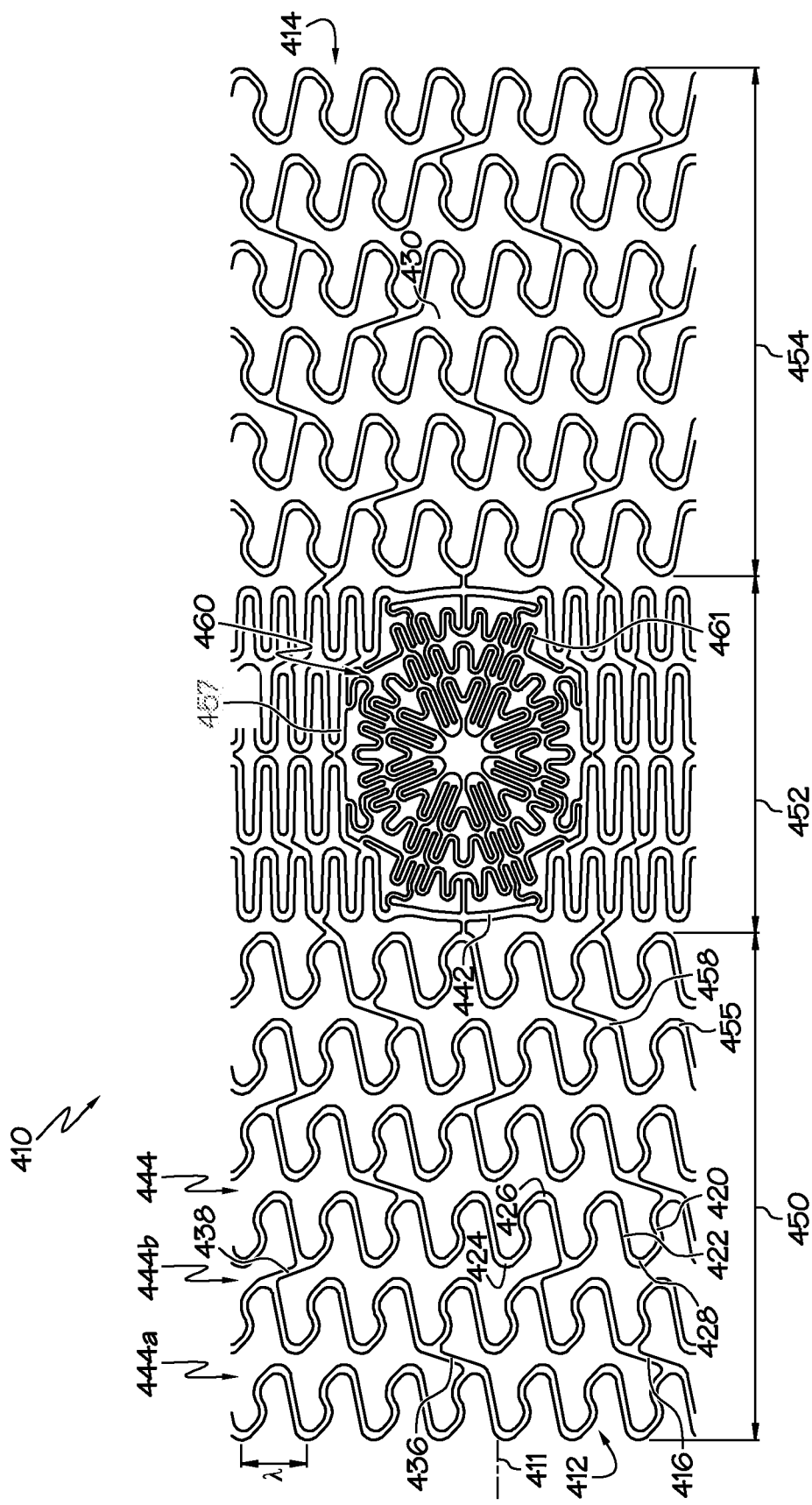
Figure 65:
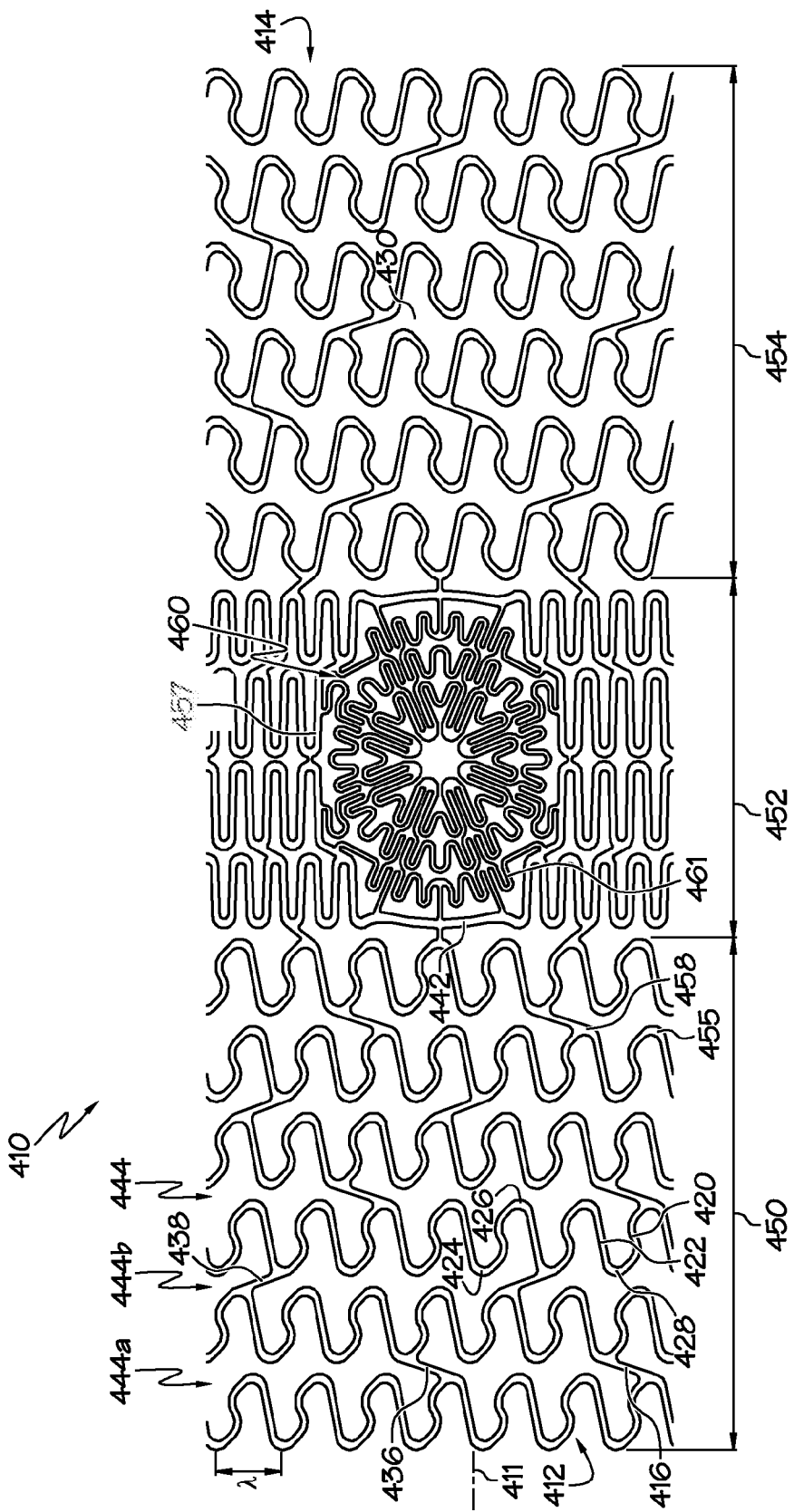

FIGS. 64 and 65 each show a flat pattern for another embodiment of a stent 410. The stent 410 is similar to the pattern of FIG. 63. FIGS. 64 and 65 show additional embodiments of a support ring 442 and additional embodiments of ancillary side branch structure 461.

Figure 66:
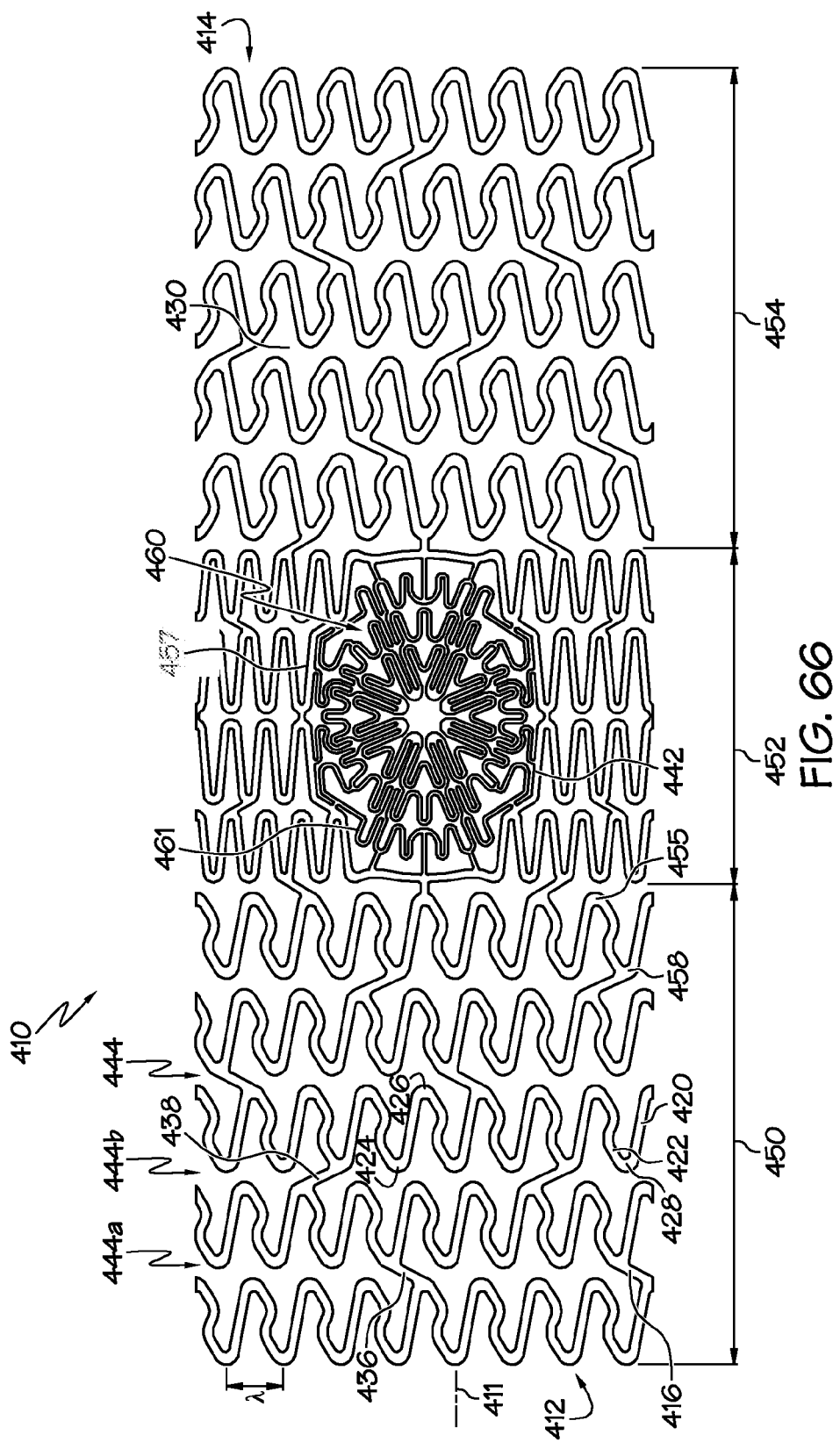
Figure 67:
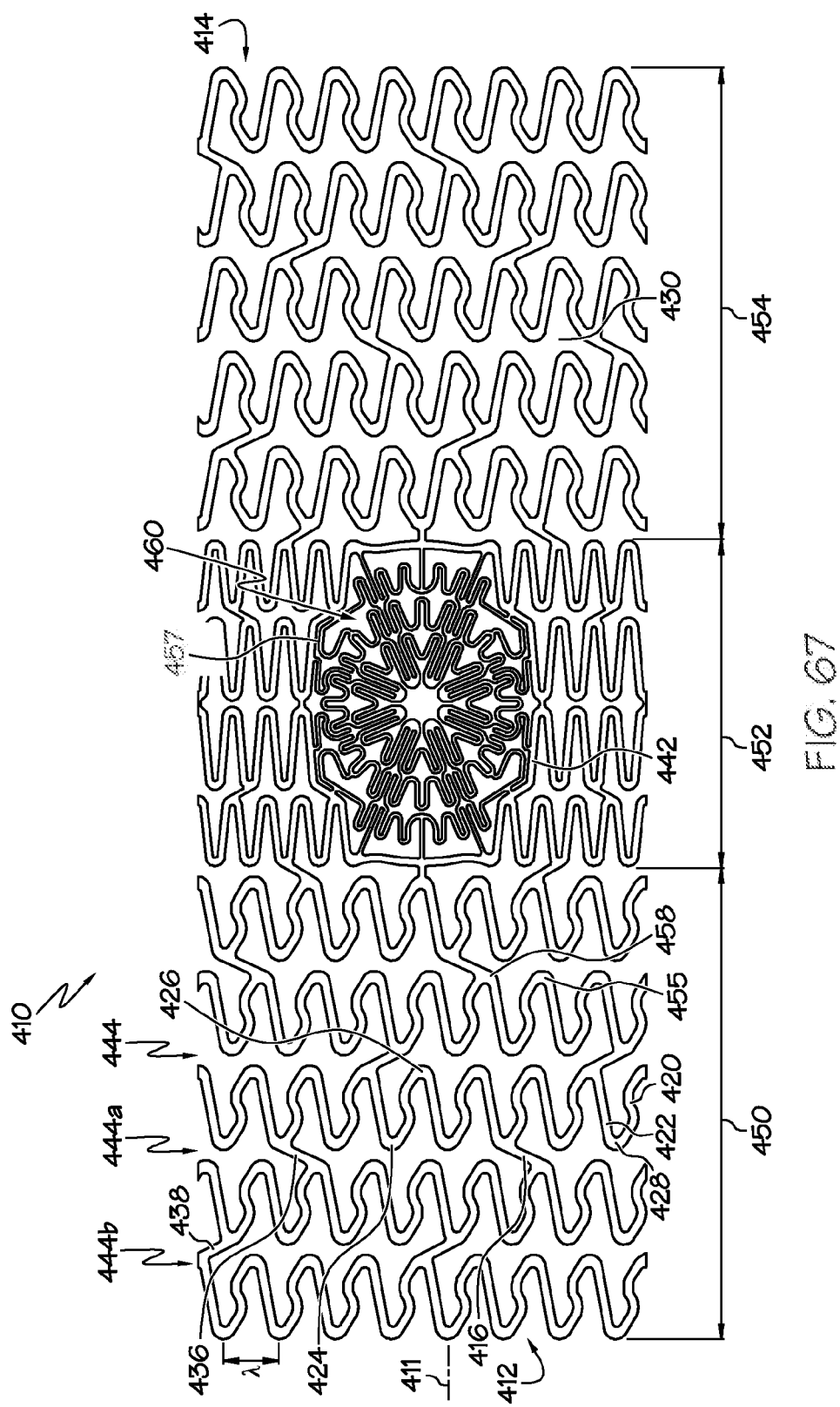
Figure 68:
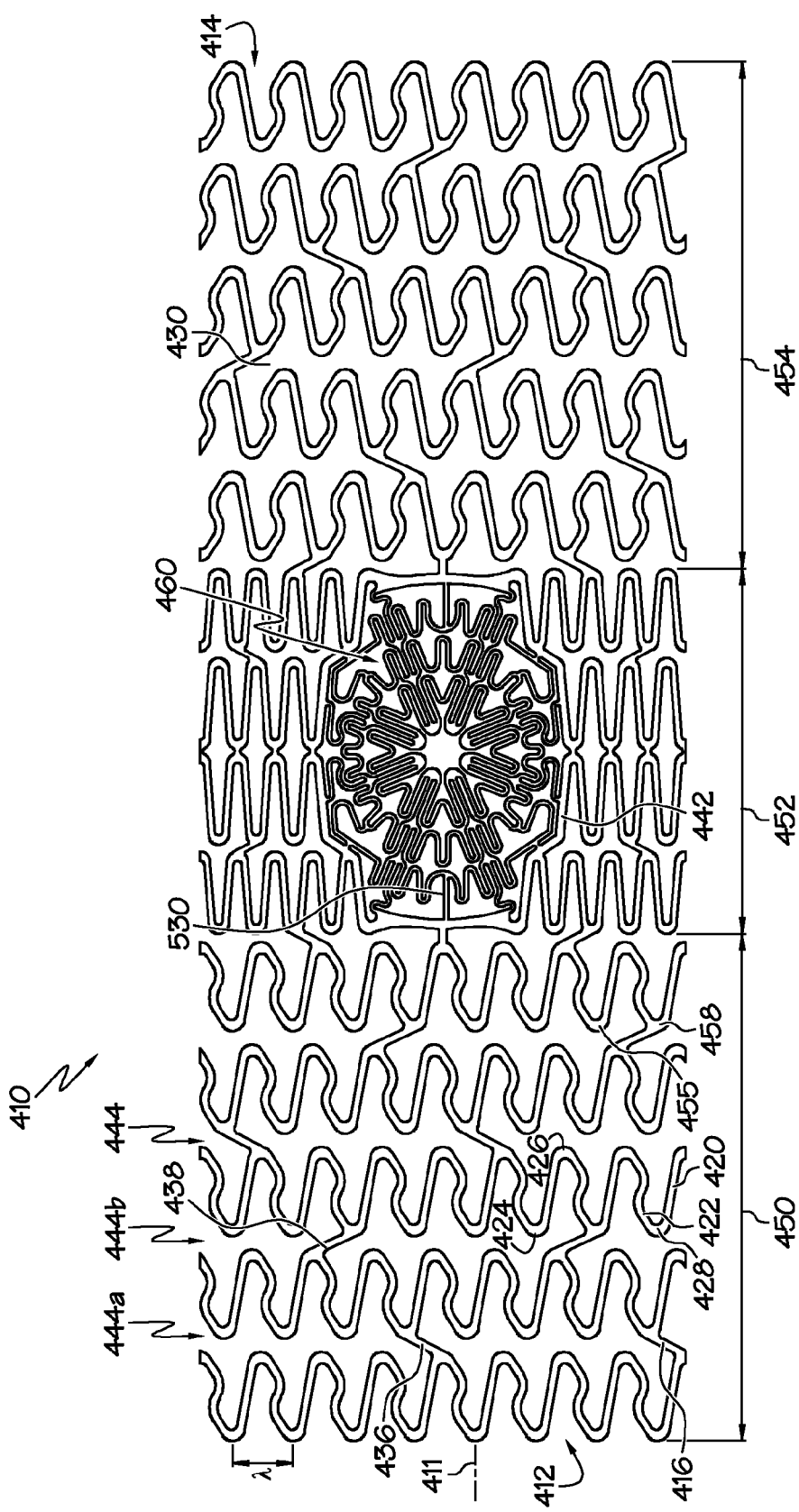

FIGS. 66-68 each show a flat pattern for another embodiment of a stent 410 that is similar to the pattern of FIG. 63. FIGS. 66-68 show additional embodiments of a support ring 442 and additional embodiments of side branch structure 460 and ancillary side branch structure 461. FIGS. 66-68 also show serpentine bands 420 in the end regions 450, 454 that comprise more struts 422 and turns 428 than the serpentine bands 420 shown in FIG. 63. The serpentine bands 420 shown in FIGS. 66 and 67 comprise struts 422 and turns 428 having greater widths than the serpentine bands 420 shown in FIG. 68.

FIG. 68 shows an embodiment comprising at least one straight ancillary side branch connector 530.

Figure 69:
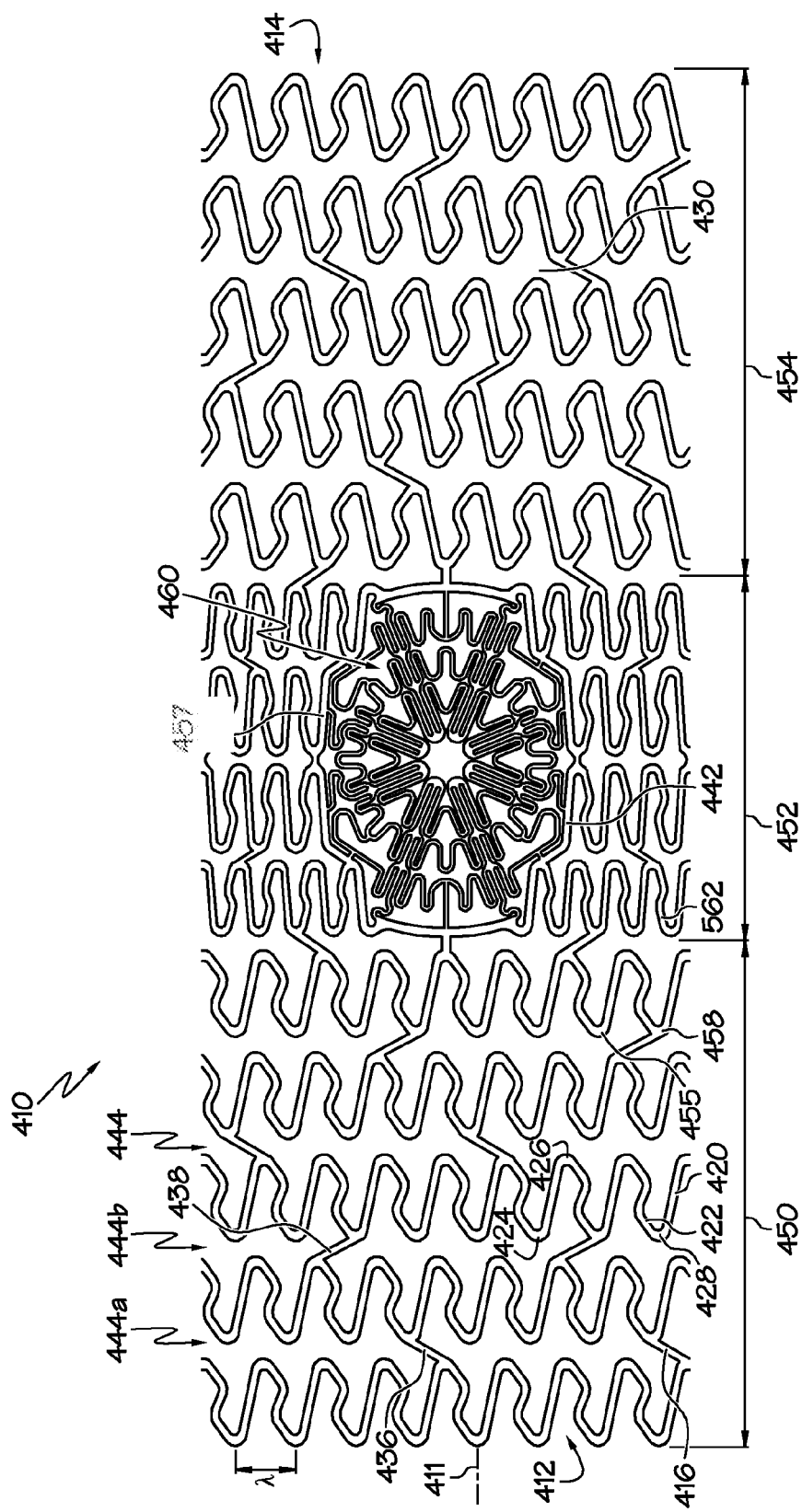

FIG. 69 shows a flat pattern for another embodiment of a stent 410.

In some embodiments, the serpentine bands 420 located in the central region 452 of the stent 410 comprise alternating straight struts 422 and s-shaped struts 562.

The continuation struts 457 of the support ring 442 are straight. Thus, each continuation strut 457 is adjacent to an s-shaped strut 562 in the serpentine band 420 to which it attaches.

Figure 70:
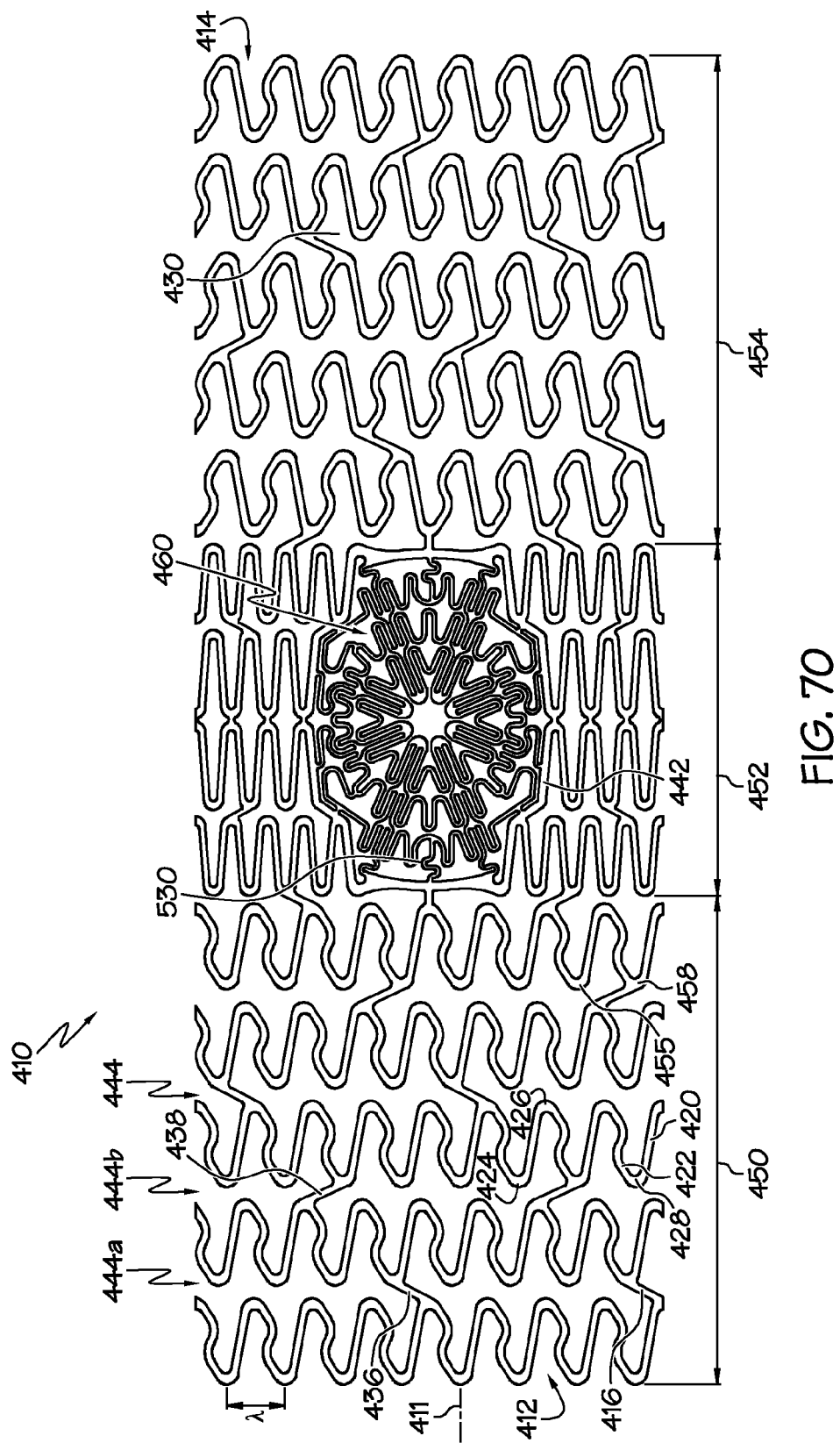

FIG. 70 shows a flat pattern for another embodiment of a stent 410 that is similar to the pattern of FIG. 68. Each ancillary side branch connector 530 of FIG. 70 comprises curved portions.

Figure 71:
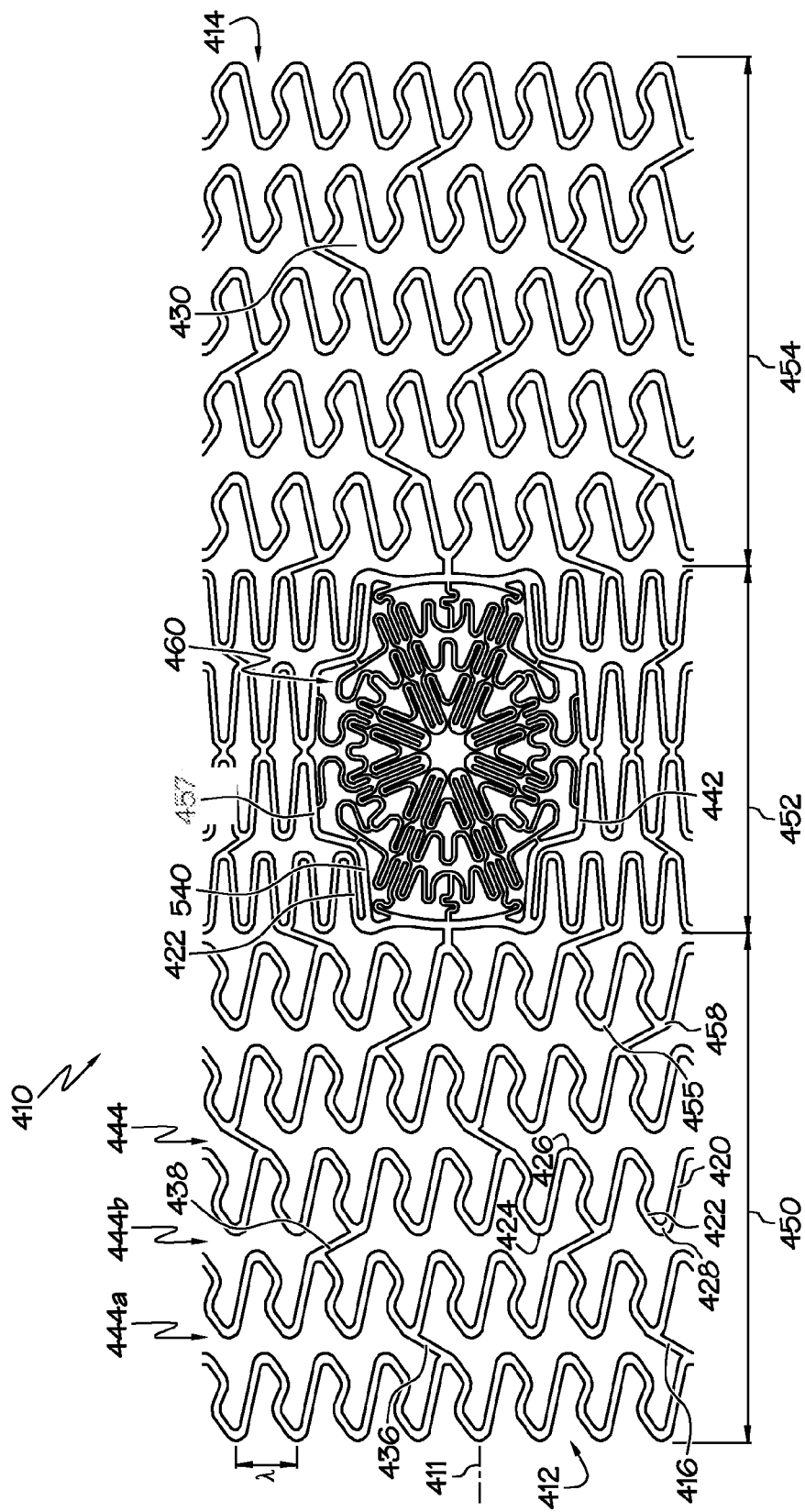

FIG. 71 shows a flat pattern for another embodiment of a stent 410. The support ring 442 comprises a plurality of continuation struts 457. The support ring 442 also comprises a plurality of straight struts 540 that are oriented parallel to the closest strut 422 of the serpentine band 420 nearest the straight strut 540.

Figure 72:
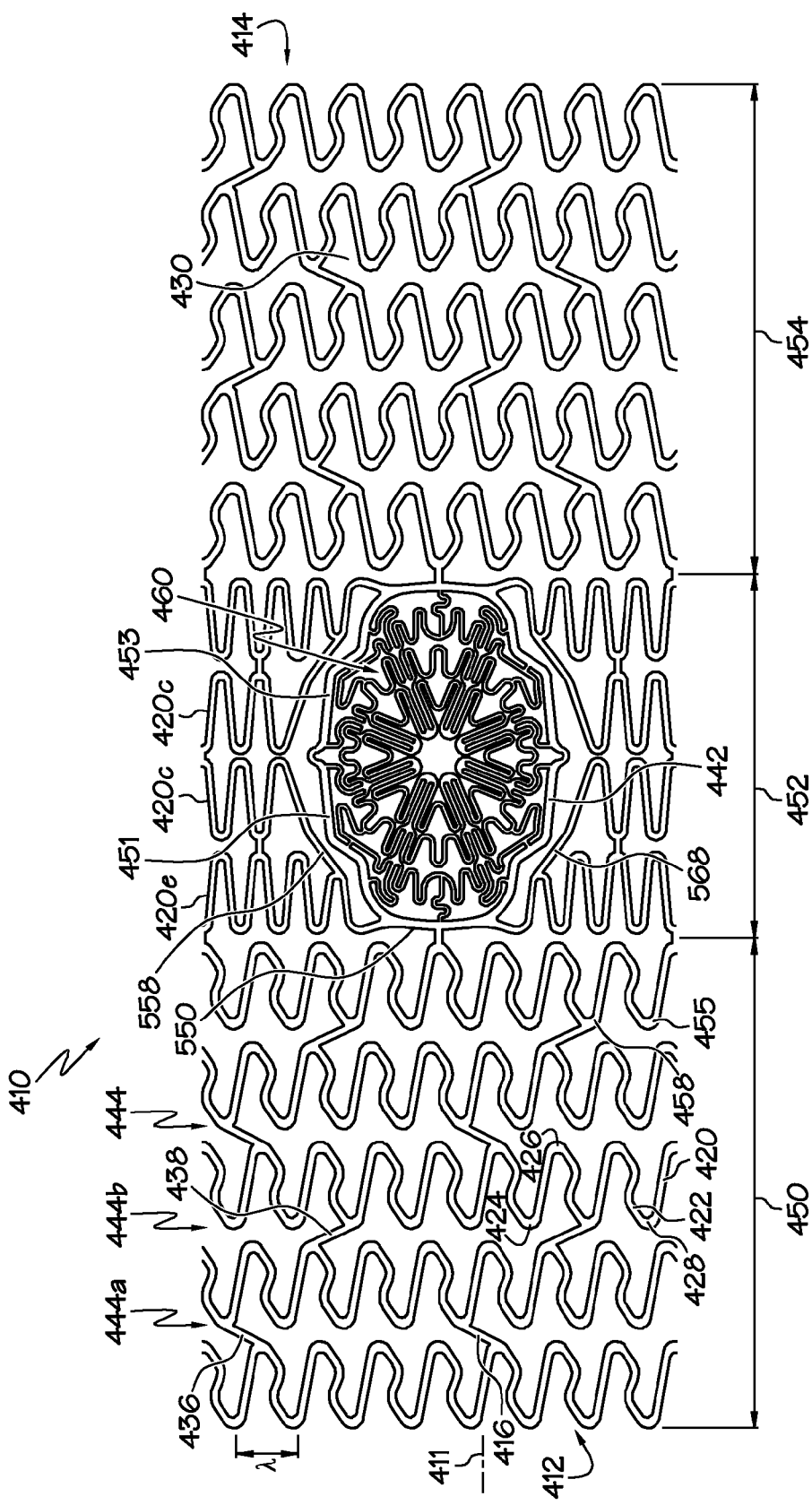
Figure 73:
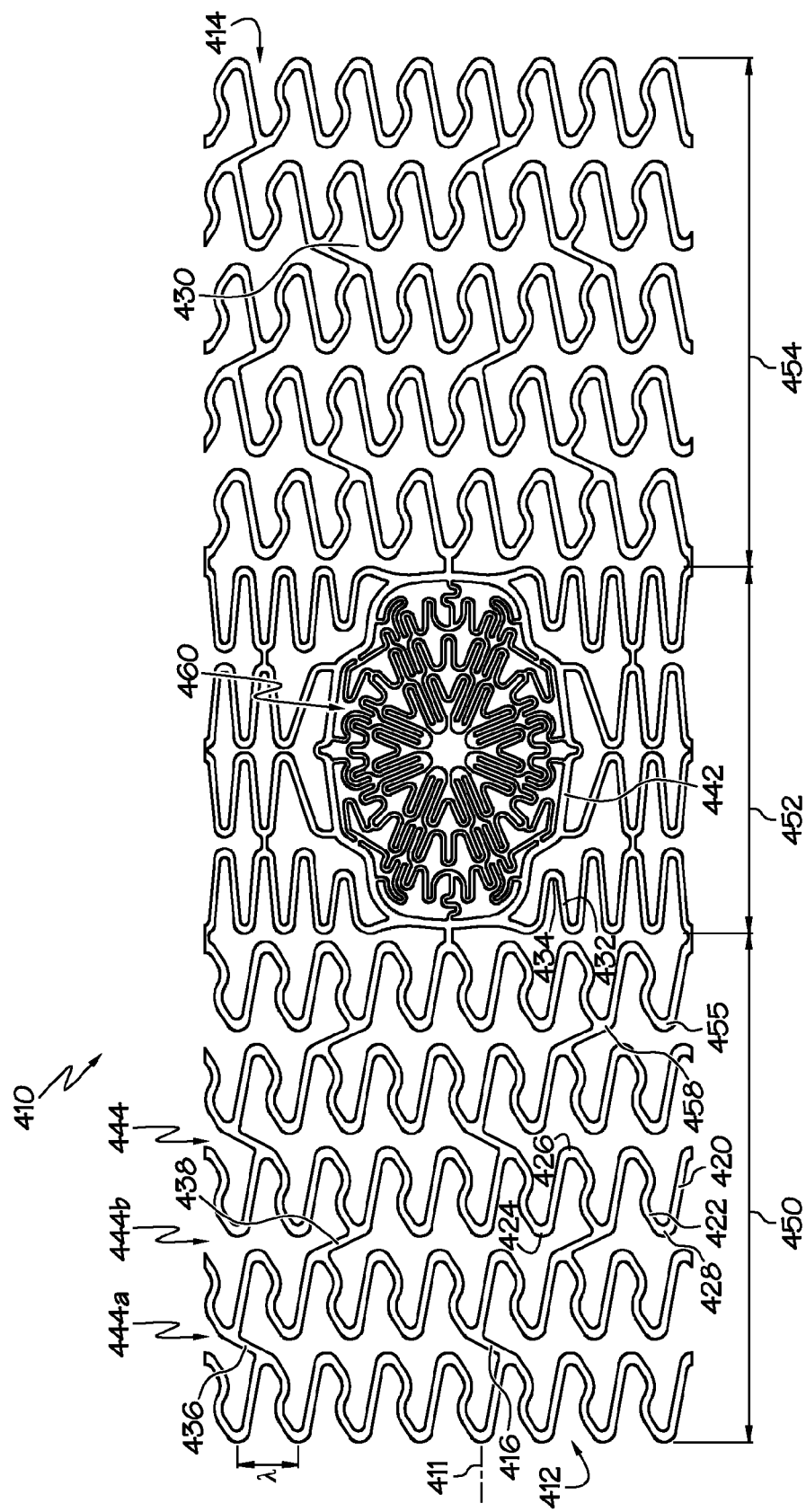
Figure 74:
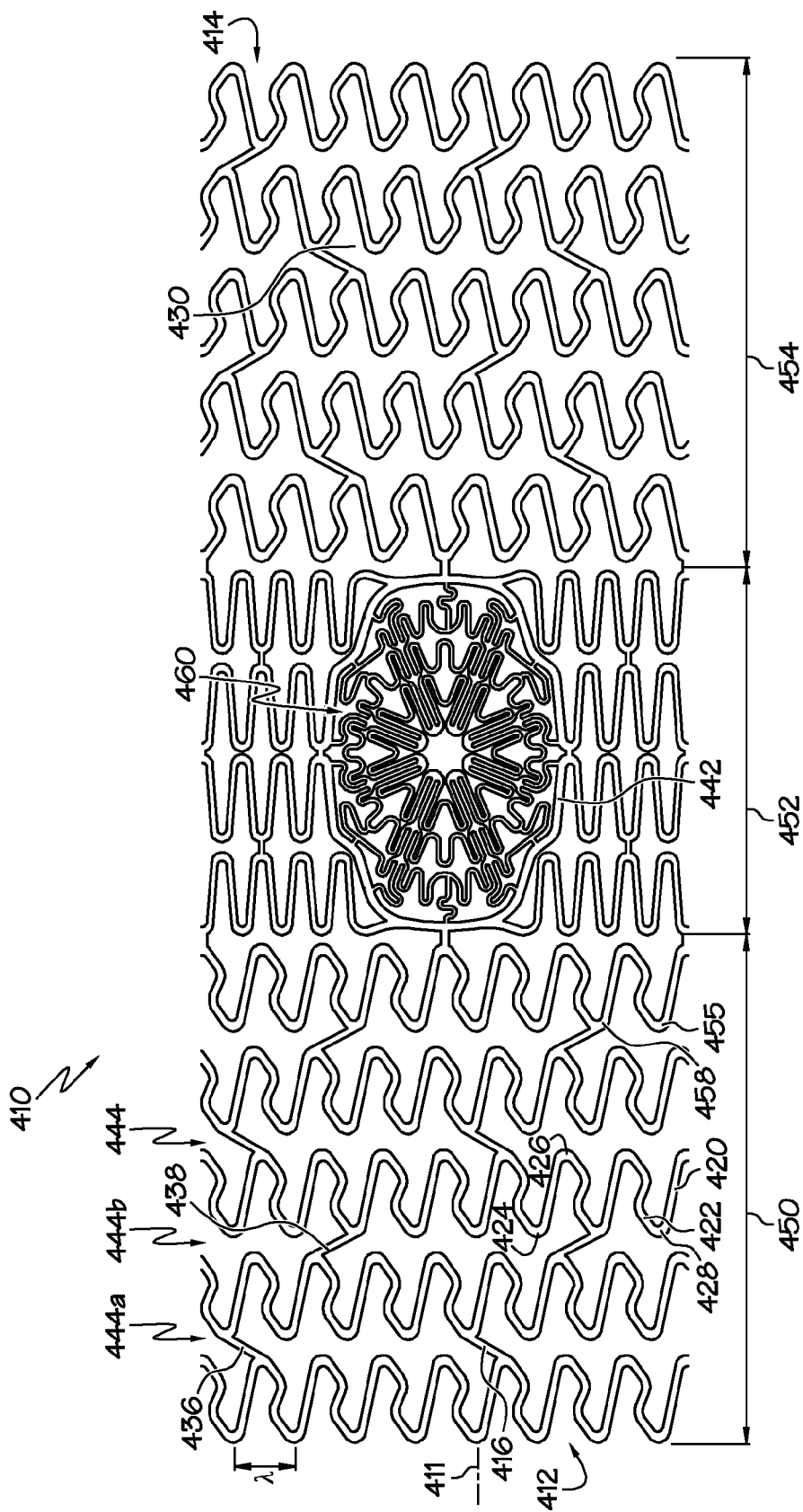
Figure 75:
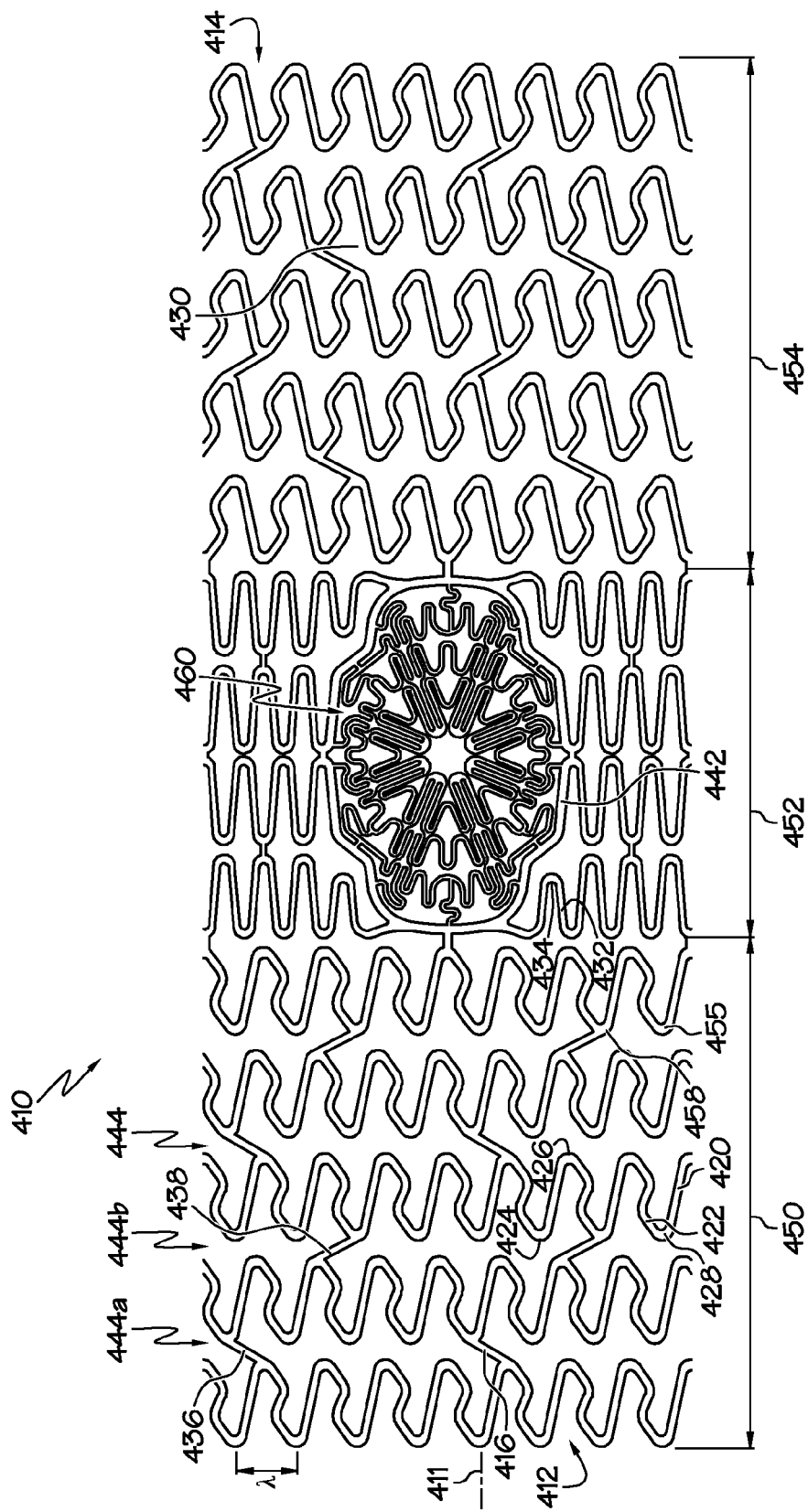
Figure 76:
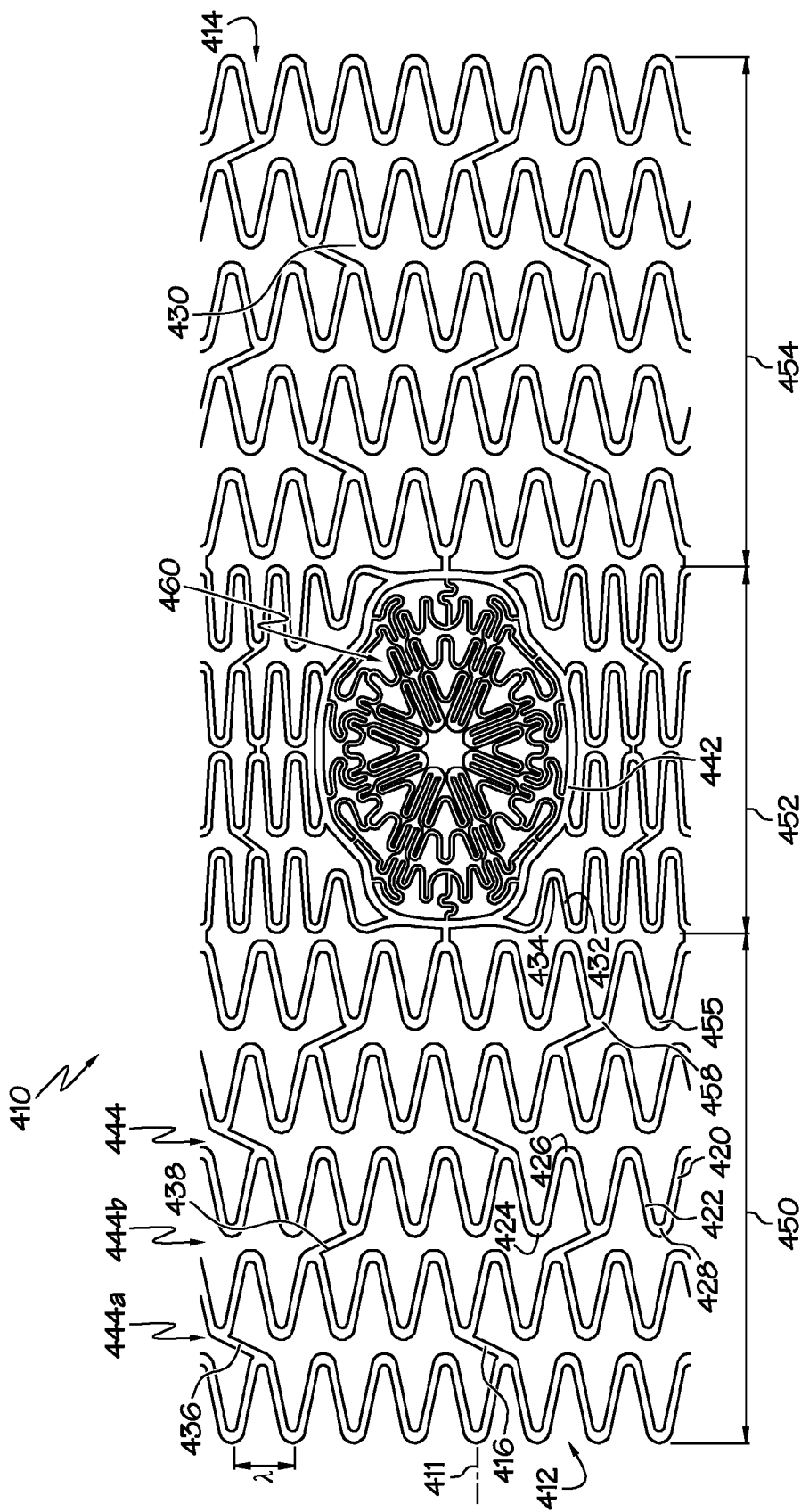
Figure 77:
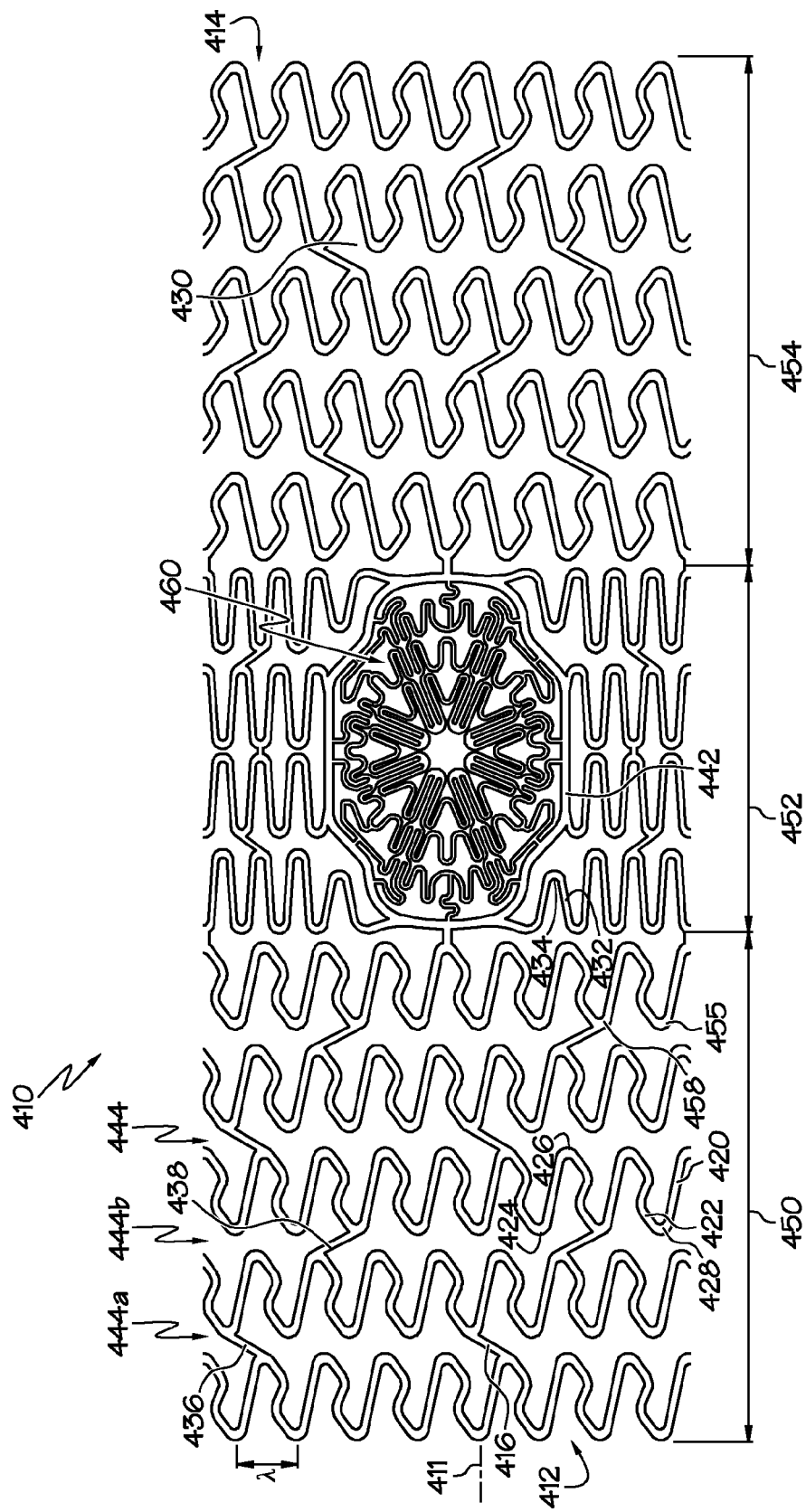

FIG. 72 shows a flat pattern for another embodiment of a stent 410. The support ring 442 only attaches to serpentine bands 420 at its longitudinally opposed ends 550.

The central region 452 of the stent 410 comprises intermediate end serpentine bands 420e and central serpentine bands 420c. The intermediate end serpentine bands 420e are located at either end of the central region 452. The central serpentine bands 420c are not located at either end of the central region 452.

The central serpentine bands 420c do not connect directly to the support ring 442. Each central serpentine band 420c comprises an extension strut 568 that extends beyond the portion of stent length generally occupied by the central serpentine band 420c and into a portion of stent length generally occupied by an intermediate end serpentine band 420e. The extension strut 568 also connects to the intermediate end serpentine bands 420e. In some embodiments, an extension strut 568 connects to an offset turn 434 of an intermediate end serpentine band 420e.

FIGS. 73-77 each show a flat pattern for another embodiment of a stent 410. Each FIG. shows an additional embodiment of a support ring 442 and additional embodiments of side branch structure 460 and ancillary side branch structure 461.

Figure 78:
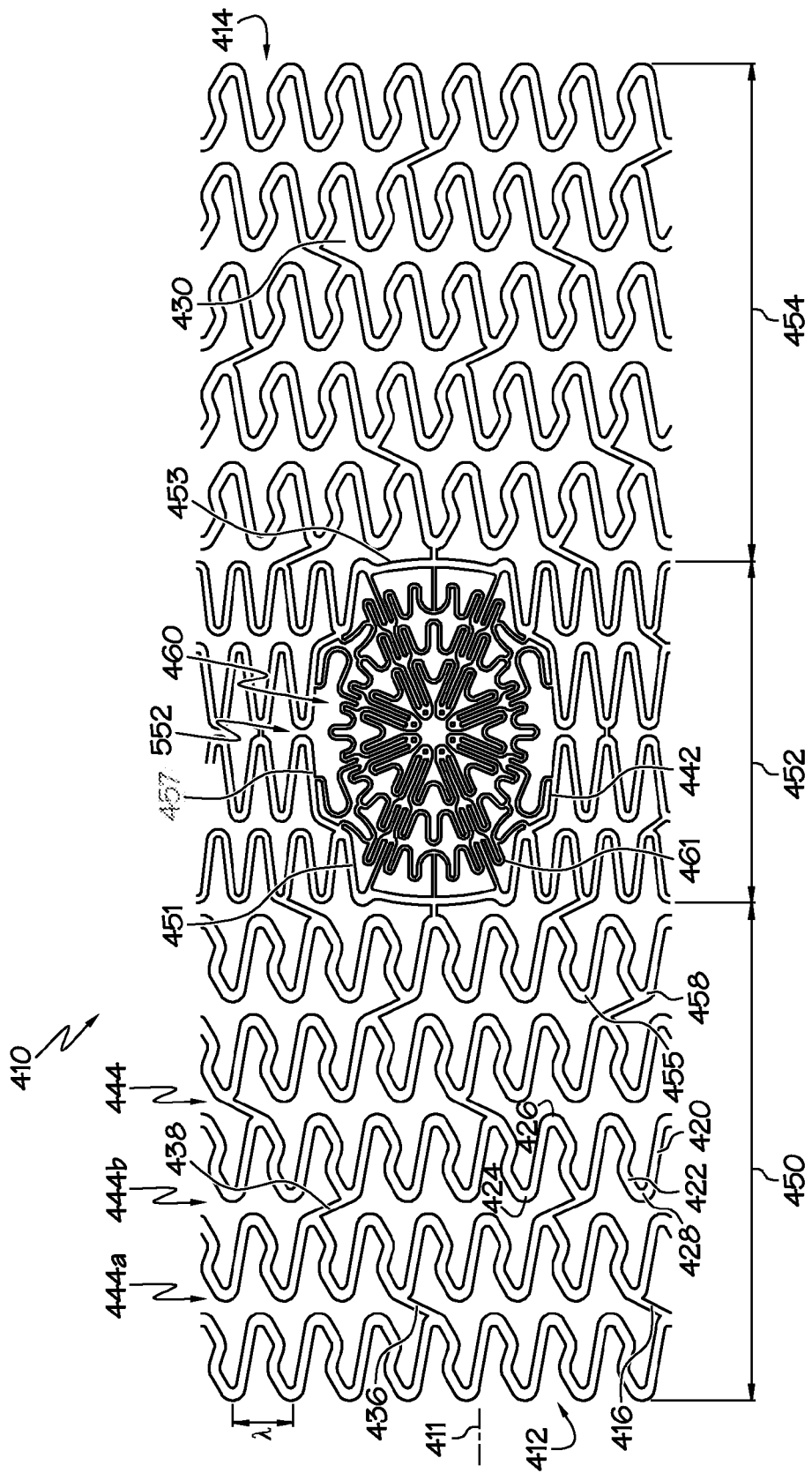
Figure 79:
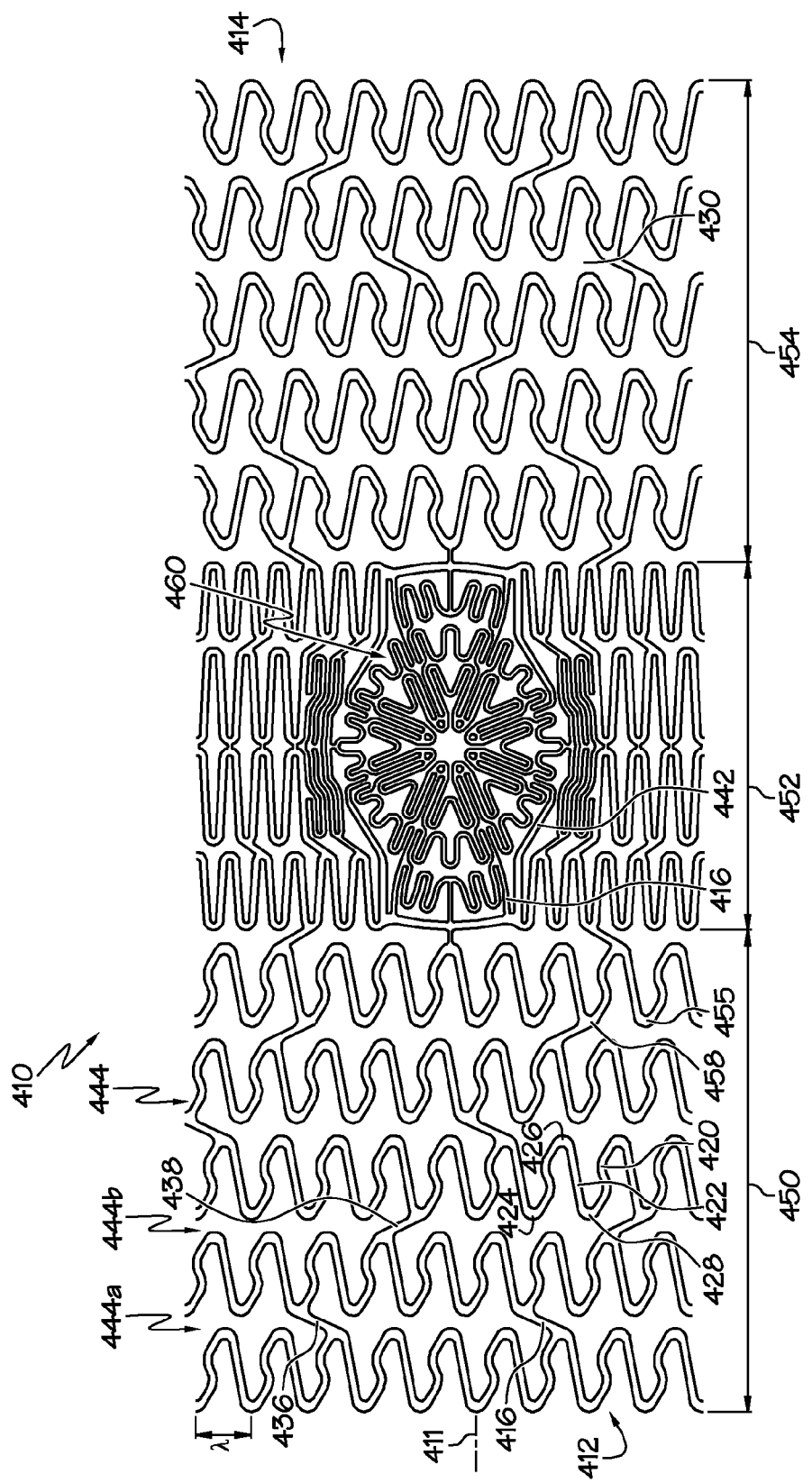
Figure 80:
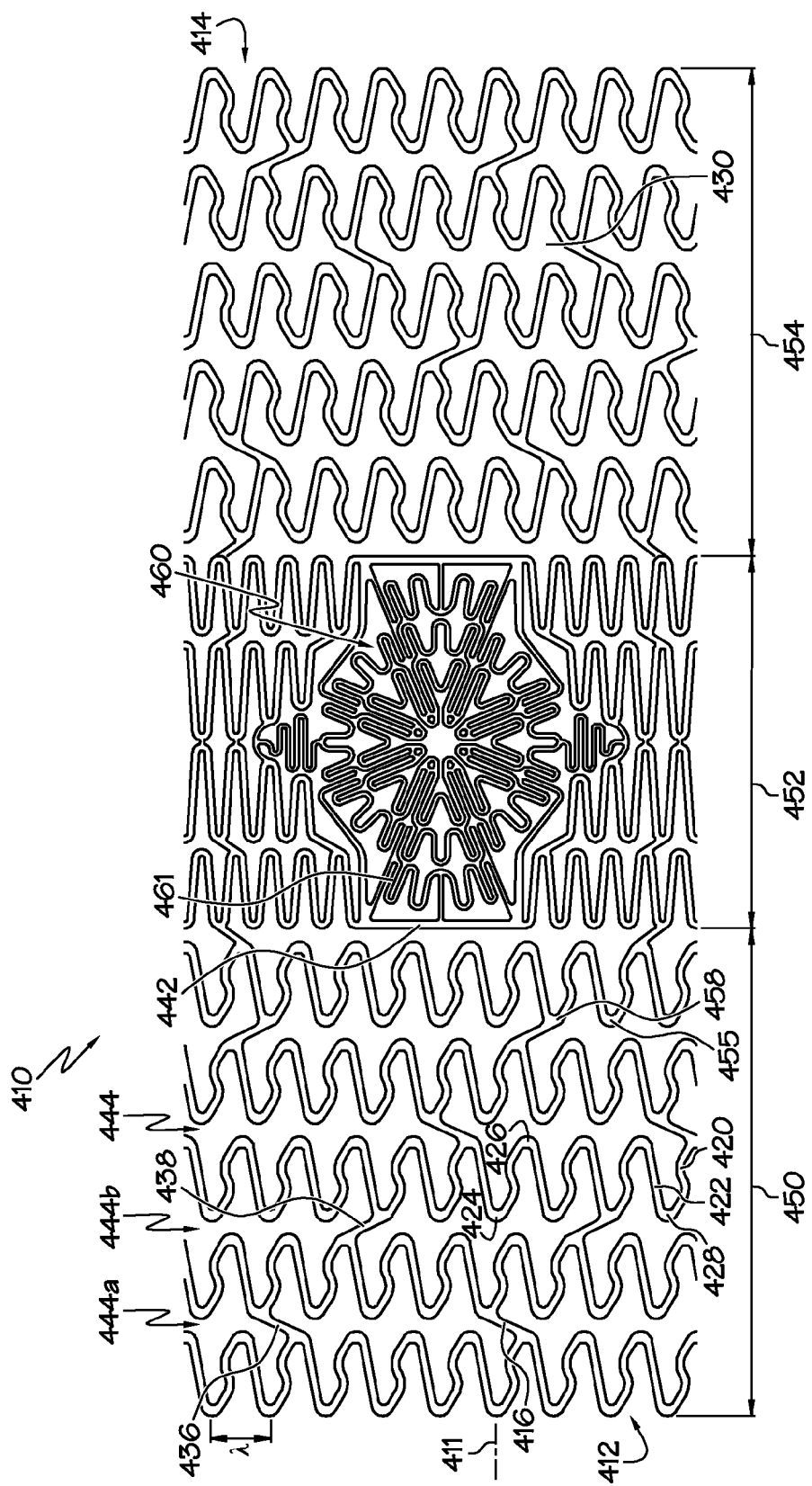
Figure 81:
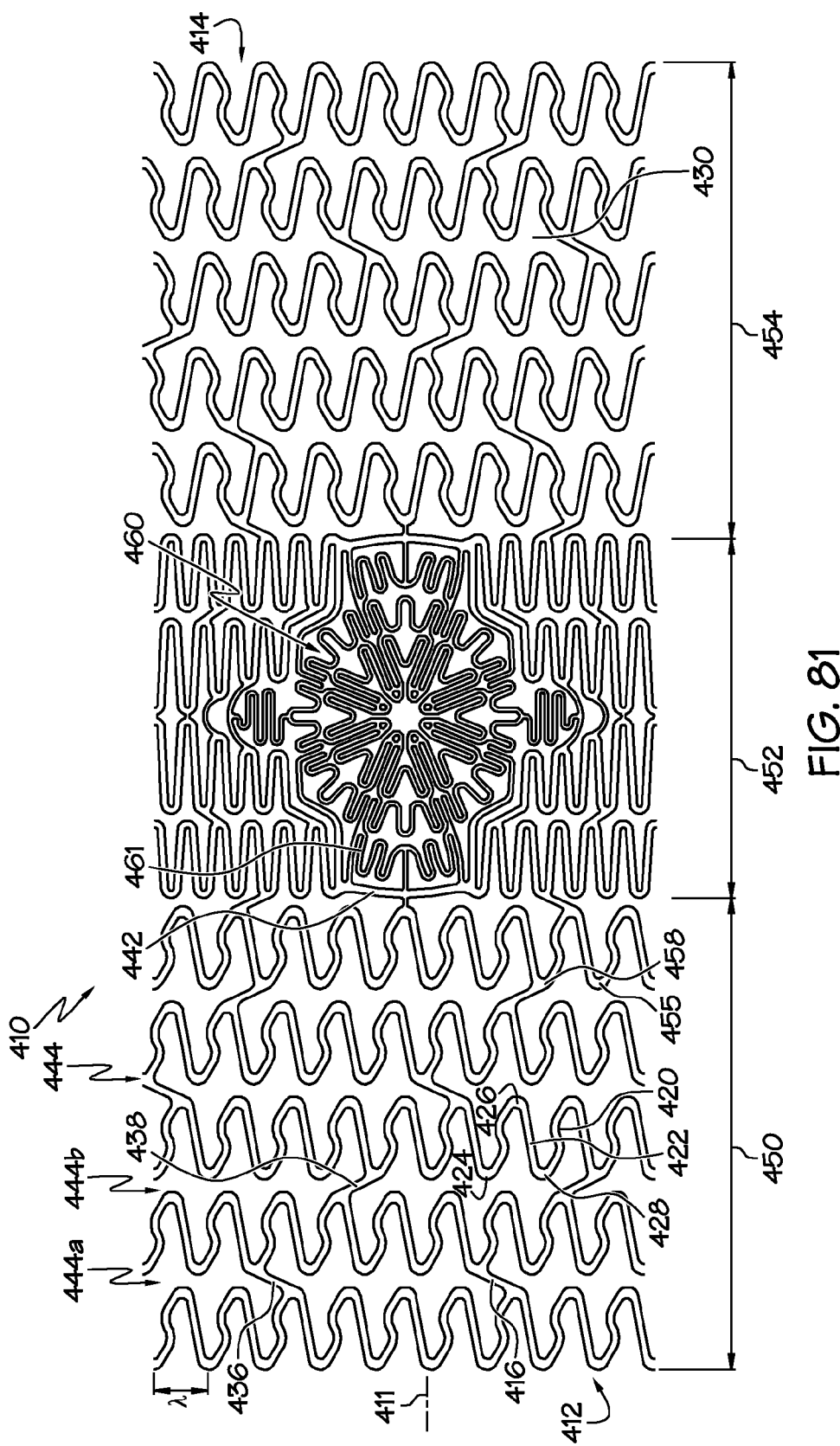
Figure 82:
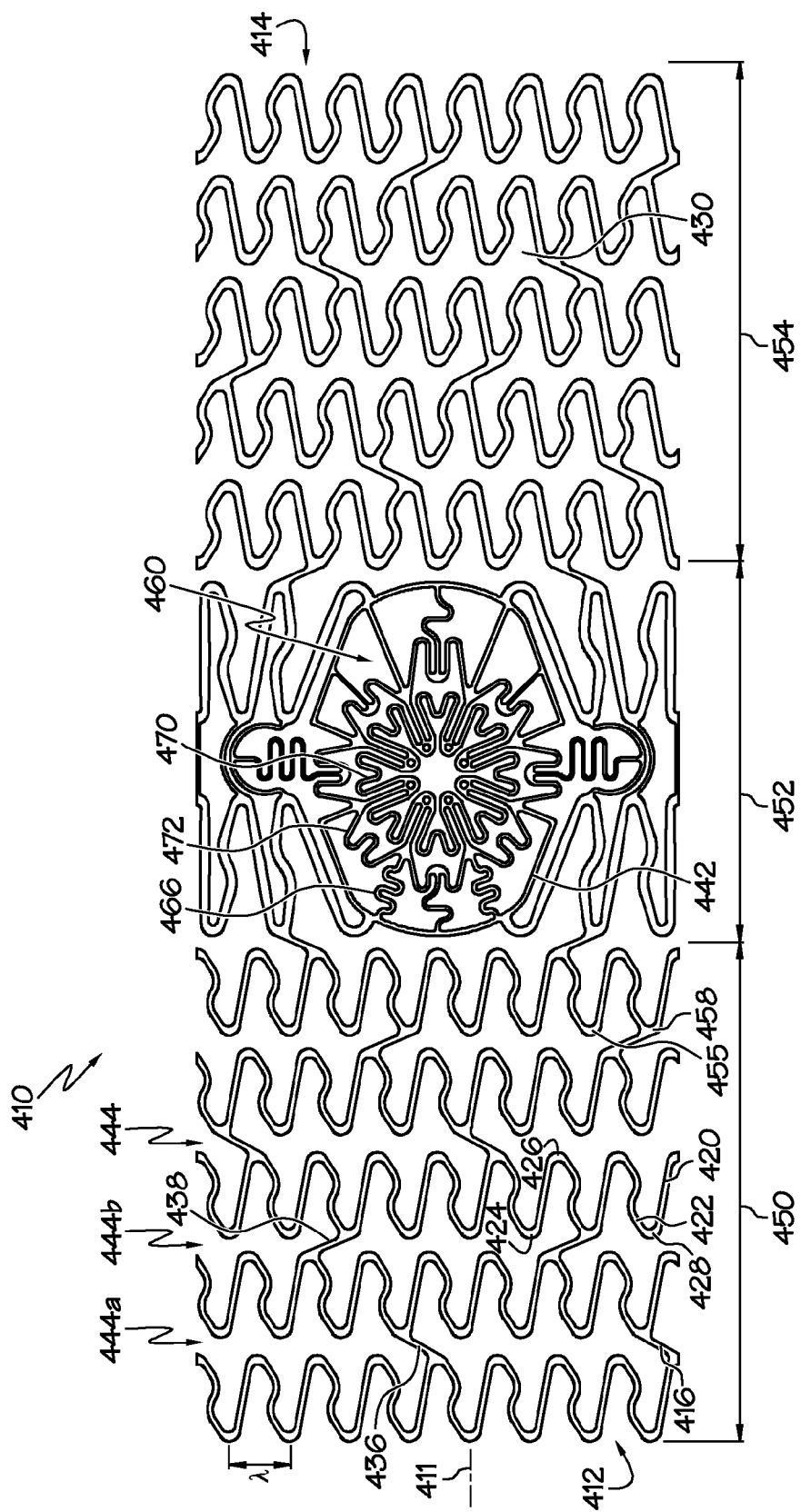
Figure 83:
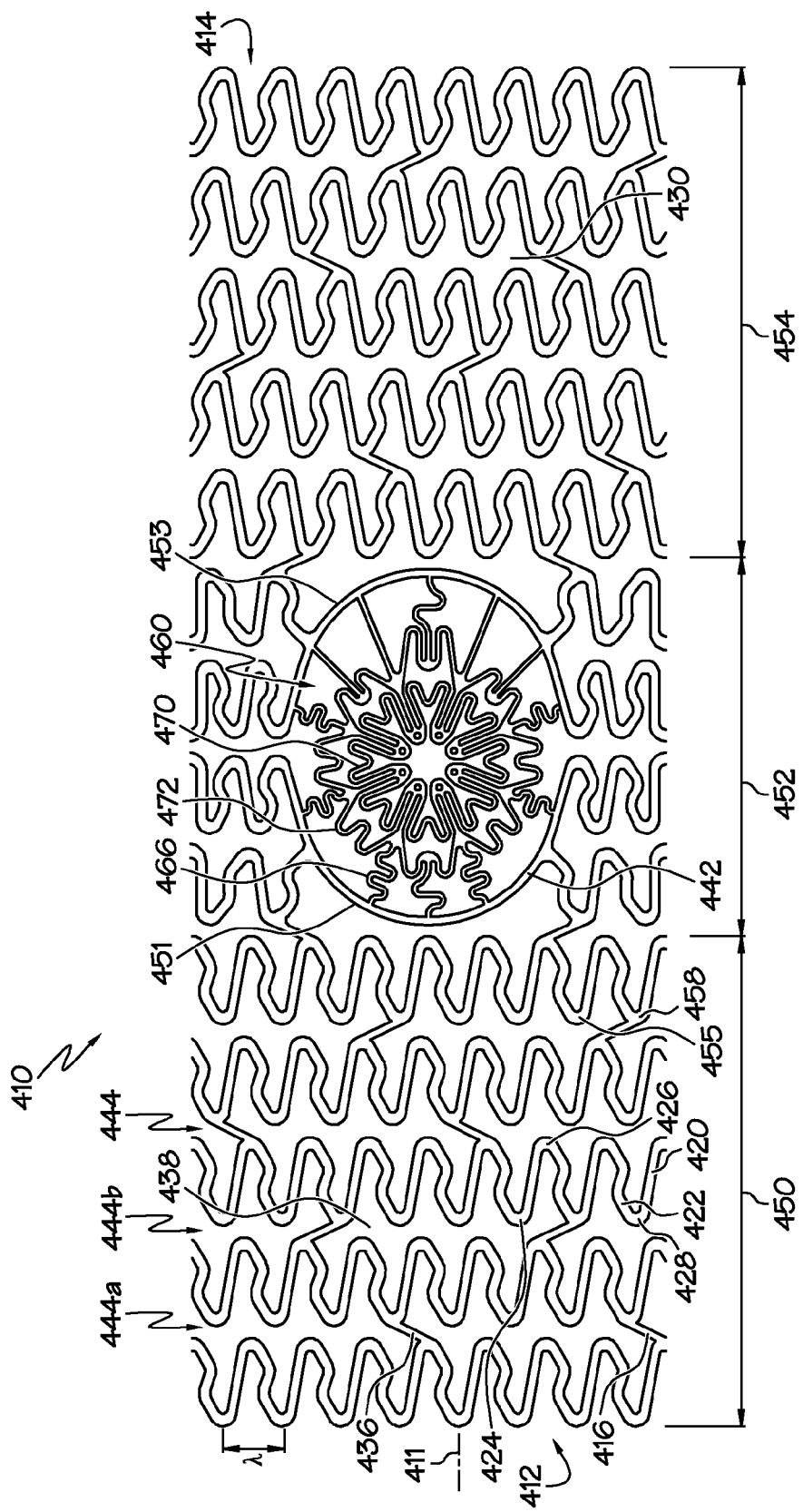
Figure 84:
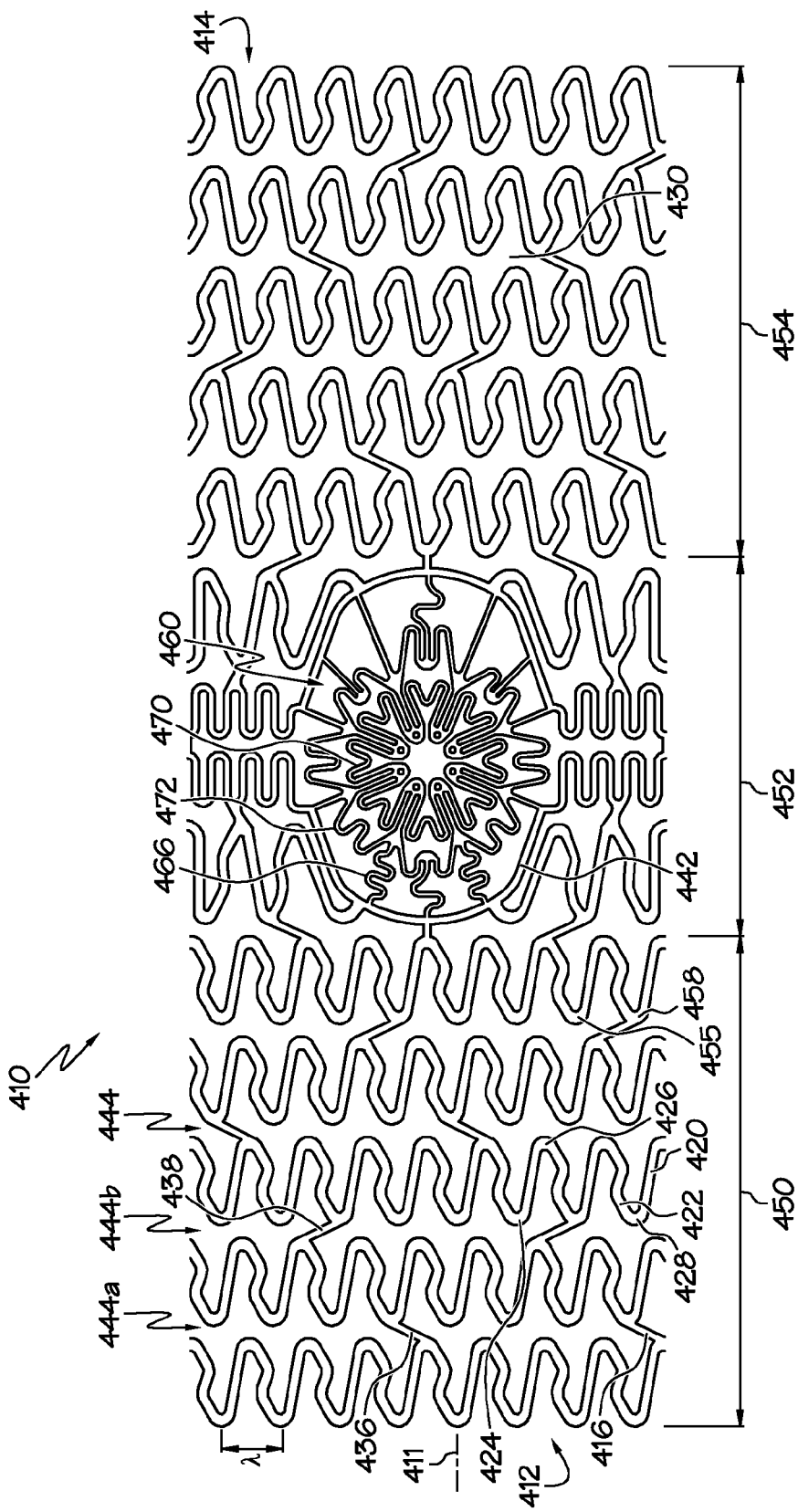
Figure 85:
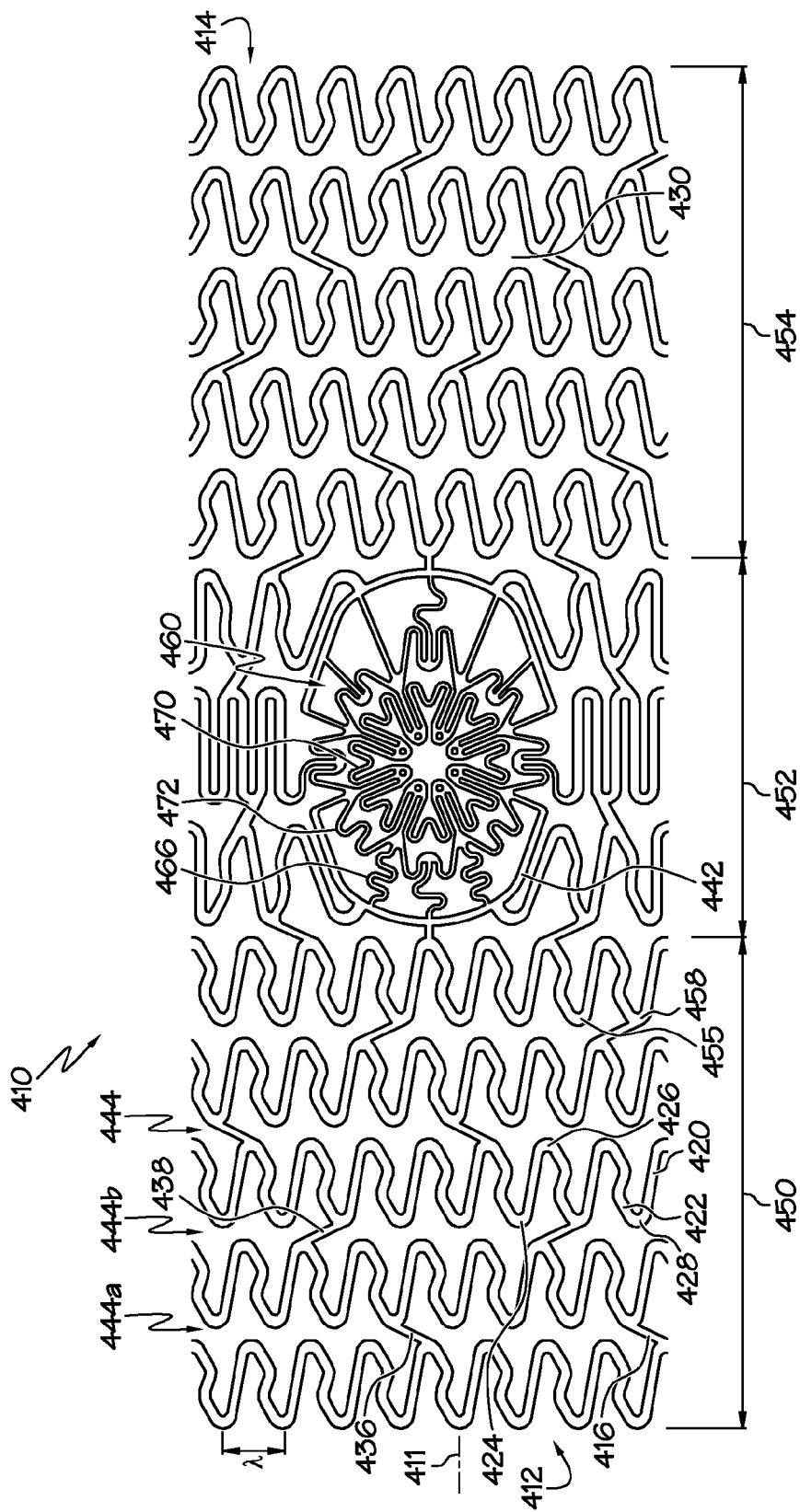

FIG. 78 shows a flat pattern for another embodiment of a stent 410 wherein the support ring 442 is discontinuous. The support ring 442 comprises a first portion 451 and a second portion 453 as herein described. However, the first portion 451 is not directly connected to the second portion 453. A gap 552 exists where the first portion 451 would otherwise be connected to the second portion 453. The gap 552 provides for increased longitudinal flexibility.

FIGS. 79-85 each show a flat pattern for another embodiment of a stent 410 comprising a discontinuous support ring 442. Each pattern shows further embodiments of serpentine bands 420 located in the central region 452. Each pattern shows further embodiments of ancillary side branch structure 461.

FIGS. 82-85 each show an embodiment where the first side branch ring 470 is not centered within the support ring 442. The first side branch ring 470 is axially offset slightly in the direction of the proximal end 412 of the stent 410. The second side branch ring 472 and the side branch outer connectors 466 are asymmetrical across an axis oriented in a stent circumferential direction.

Figure 86:
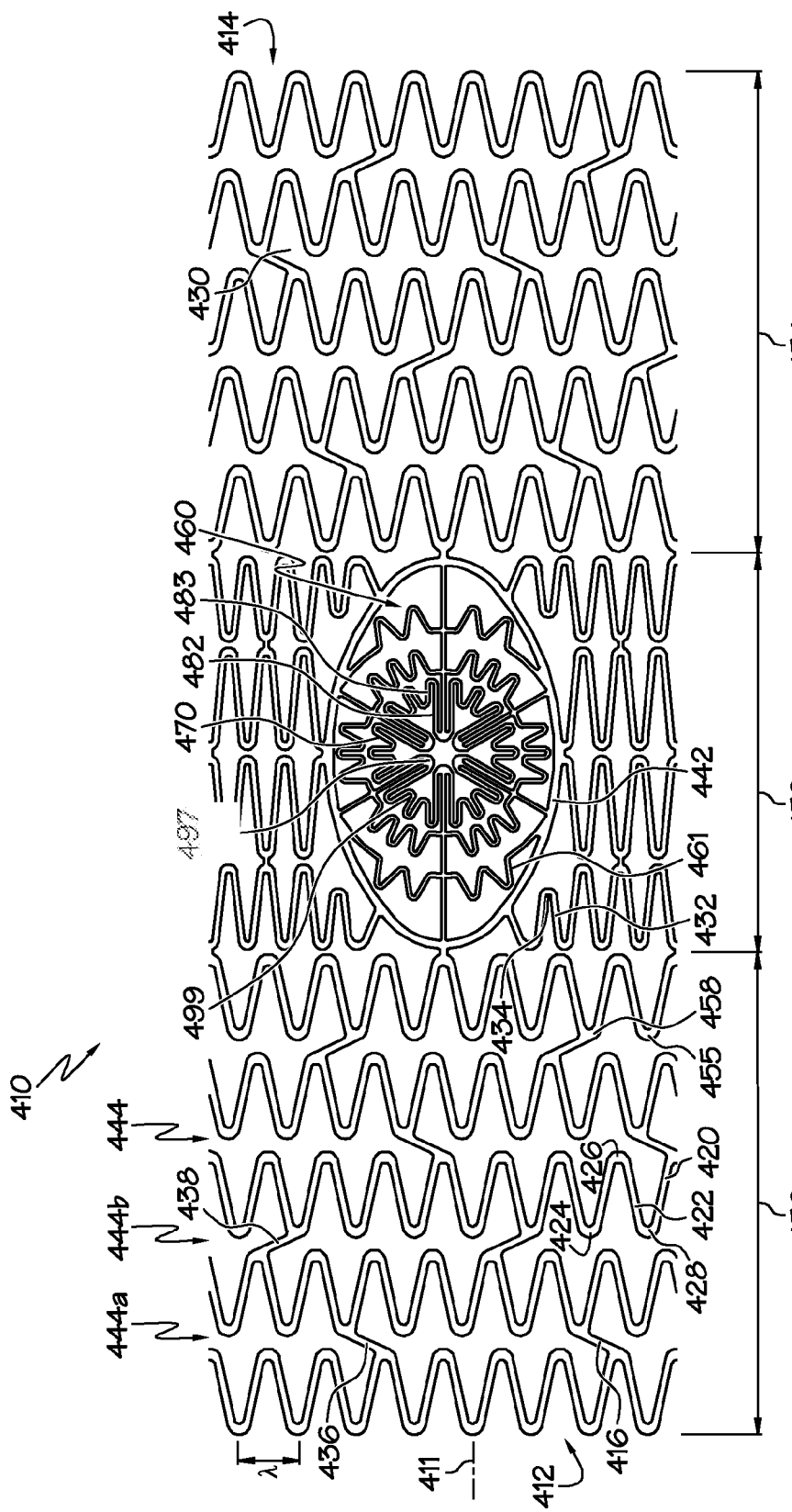

FIG. 86 shows another embodiment of the side branch structure 460 and the ancillary side branch structure 461.

In some embodiments, the turns 486 of the first serpentine ring 470 comprise alternating inner turns 487 and outer turns 488. The inner turns 487 further comprise first inner turns 497 and second inner turns 499. The first serpentine ring 470 comprises twice as many second inner turns 499 as first inner turns 497. The inner turns 487 of the first serpentine ring 470 comprise a repeating pattern of a first inner turn 497 and two second inner turns 499 as the first serpentine ring 470 is traversed.

In some embodiments, the struts of the first serpentine ring 470 comprise longer struts 482 and shorter struts 483. The first serpentine ring 470 can comprise twice as many shorter struts 483 as longer struts 482.

Figure 87:
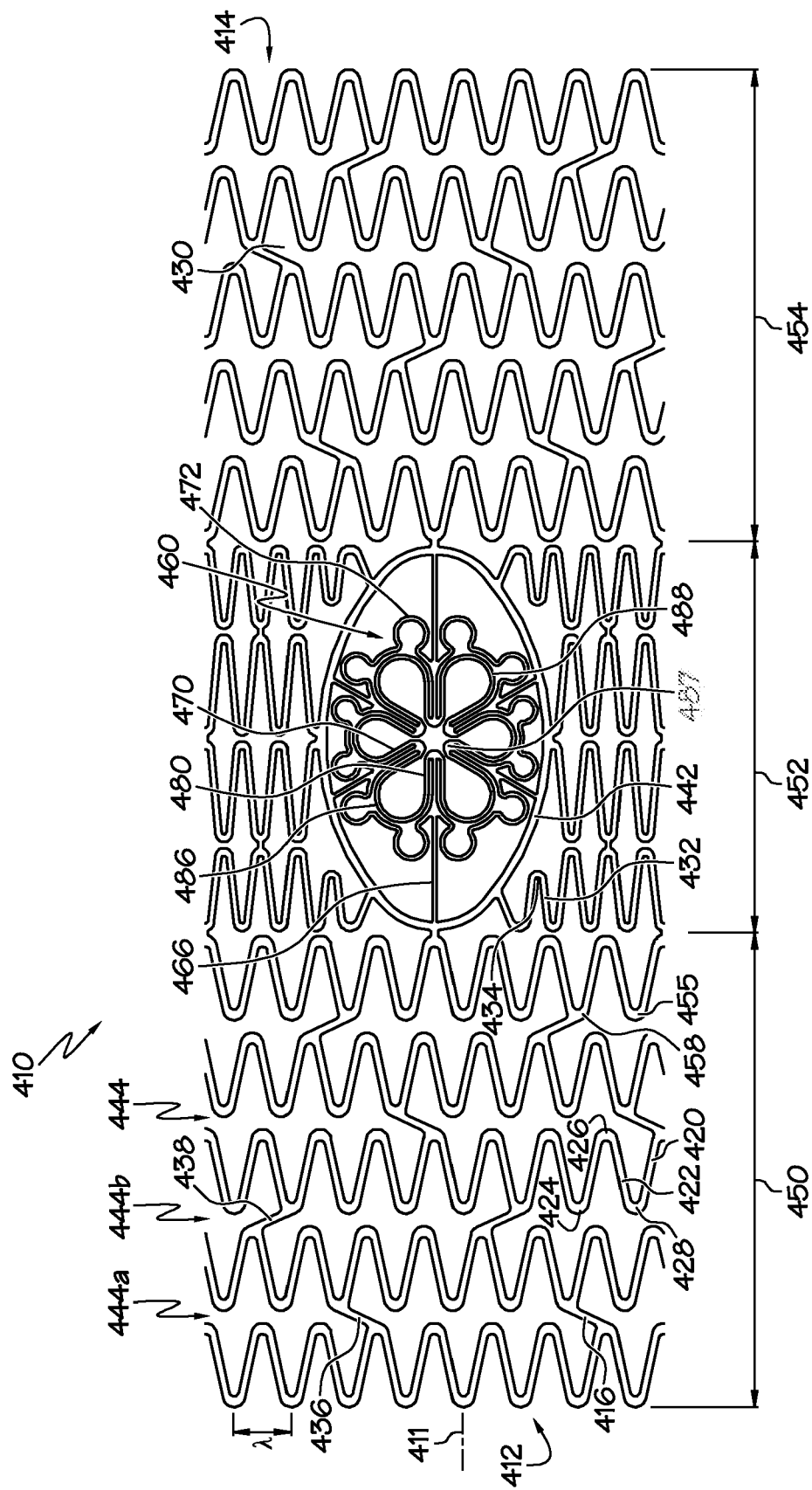
Figure 88:
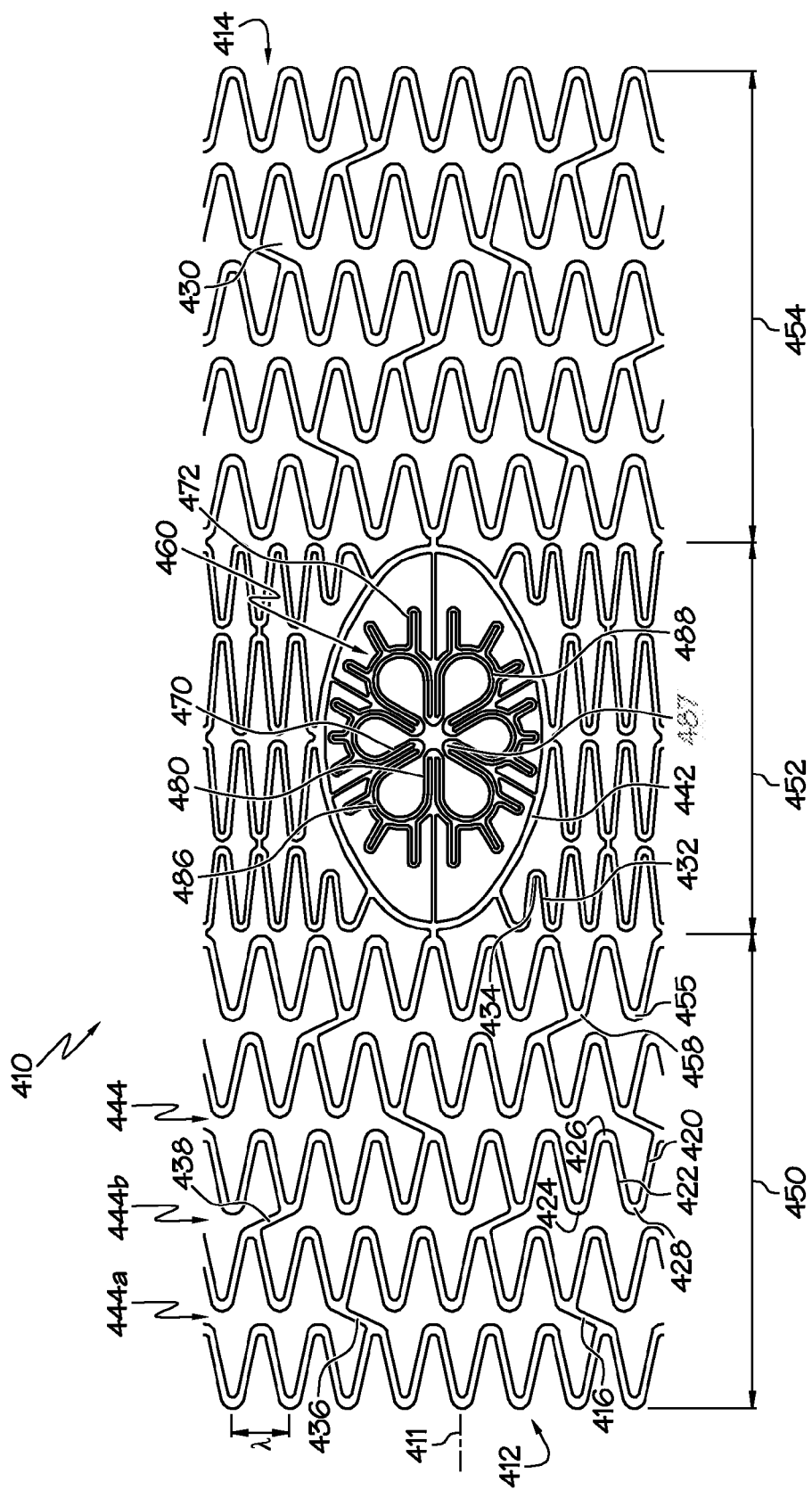
Figure 89:
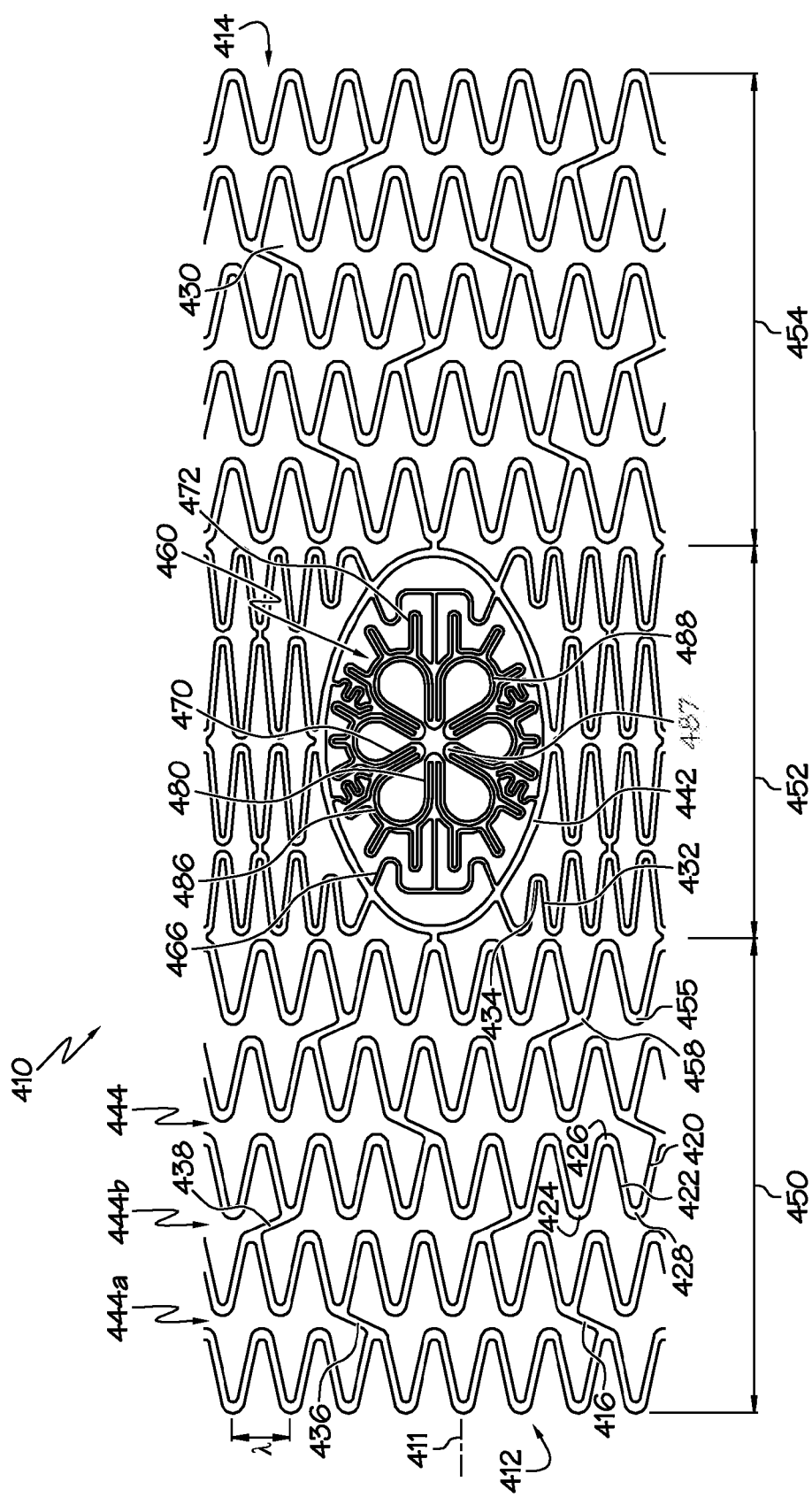

FIGS. 87-89 each show a flat pattern for another embodiment of a stent 410.

In some embodiments, the first serpentine ring 470 comprises a plurality of alternating straight struts 480 and turns 486. The turns 486 comprise alternating inner turns 487 and outer turns 488.

Each inner turn 487 is centered in a side branch radial direction. Each inner turn 487 is connected to two straight struts 480 that are parallel to the side branch radial direction that bisects the inner turn 487.

Each outer turn 488 comprises a continuous magnitude of curvature (e.g. fixed radius of curvature), and is curved to a lesser degree than the inner turns 487. Each outer turn 488 connects at one end to one straight strut 480 and at the other end to another straight strut 480. The two straight struts 480 to which an outer turn 488 connects are non-parallel to one another.

Figure 90:
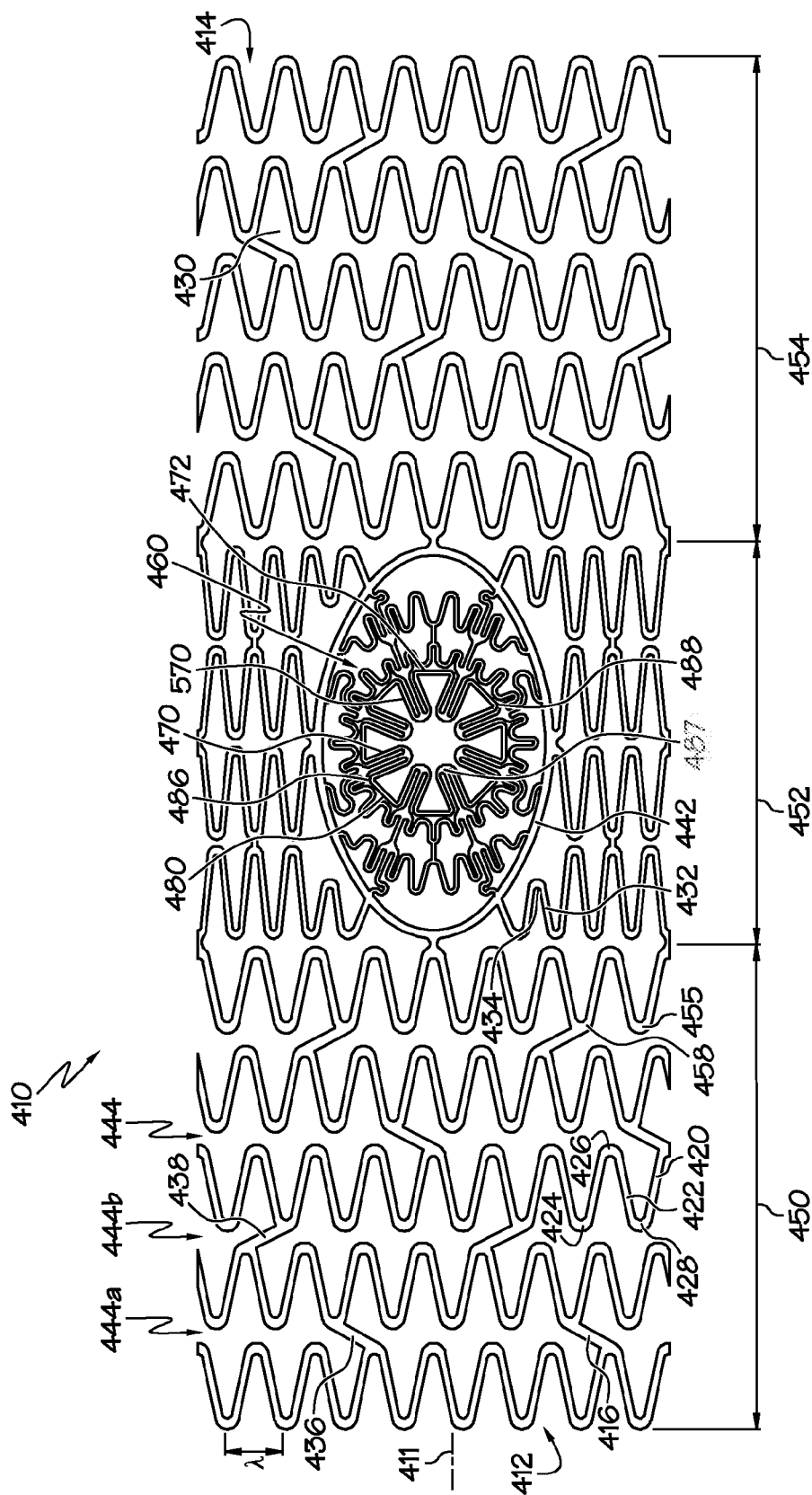

FIG. 90 shows a flat pattern for another embodiment of a stent 410.

In some embodiments, the first serpentine ring 470 comprises a plurality of alternating straight struts 480 and turns 486. The turns 486 comprise inner turns 487 and outer turns 488. There are twice as many outer turns 488 as inner turns 487. The turns 486 of the first serpentine ring 470 comprise a repeating pattern of an inner turn 487 and two outer turns 488 as the first serpentine ring 470 is traversed.

The straight struts 480 of the first serpentine ring 470 comprise parallel struts 570 and perpendicular struts 574. Each parallel strut 570 connects to an inner turn 487. Each inner turn 487 is centered in a side branch radial direction. Each inner turn 487 is connected to two parallel struts 570 that are parallel to the side branch radial axis that bisects the inner turn 487. Each perpendicular strut 574 connects between two outer turns 488. Each perpendicular strut 574 is bisected by a side branch radial axis, and is oriented perpendicular to the side branch radial axis that bisects it. The struts 480 of the first serpentine ring 470 comprise a repeating pattern of a perpendicular strut 574 and two parallel struts 570 as the first serpentine ring 470 is traversed.

In some embodiments, all of the serpentine bands 420 within a given region 450, 452, 454 are similar in size and shape. In some embodiments, various serpentine bands 420 within a given region 450, 452, 454 may be different in size, shape, strut width, wavelength, etc.

For example, in some embodiments, serpentine bands 420 located in the central region 452 span a greater distance along the length of the stent 410 than serpentine bands 420 located in the end regions 450, 454. In some embodiments, the struts 422 of serpentine bands 420 located in the central region 452 have a greater length than struts 422 located in the end regions 450, 454. In some embodiments, the struts 422 of serpentine bands 420 located in the end regions 450, 454 are wider than struts 422 located in the central region 452. In some embodiments, the wavelength λ of serpentine bands 420 located in the central region 452 is less than the wavelength λ of serpentine bands 420 located in the end regions 450, 454.

A stent 410 can have any suitable number of serpentine bands 420. In various embodiments, a serpentine band 420 can have any suitable number of struts 422 and any suitable number of turns 428. In some embodiments, a serpentine band 420 can have a constant wavelength λ or distance between repeating elements of the serpentine band 420. For example, a wavelength λ may comprise a distance between adjacent proximal peaks 424 of a serpentine band 420, or a distance between adjacent distal valleys 426 of a serpentine band 420. In some embodiments, a stent 410 includes one or more serpentine bands 420 that have a wavelength λ that is different from the wavelength λ of one or more other serpentine bands 420.

The above disclosure is intended to be illustrative and not exhaustive. This description will suggest many variations and alternatives to one of ordinary skill in this field of art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A stent comprising:
a plurality of interconnected framework members defining a plurality of cells, a portion of the interconnected framework members comprising a side branch structure defining an inner side branch cell, the inner side branch cell being shaped differently than other cells of the stent;
the side branch structure comprising:
an inner serpentine ring extending around the inner side branch cell, the inner serpentine ring comprising alternating struts and turns, the turns comprising alternating inner turns and outer turns, the inner turns comprising alternating first inner turns and second inner turns;
an outer serpentine ring, the outer serpentine ring comprising alternating struts and turns, the outer serpentine ring having more struts and more turns than the inner serpentine ring; and
a plurality of connectors each connector connecting between a first inner turn of the inner serpentine ring and an inner turn of the outer serpentine ring;
wherein the second inner turns are located farther away from a side branch center point than the first inner turns, and the struts of the inner serpentine ring that are located on either side of a connector are parallel to the connector.

2. The stent of claim 1, wherein the first inner turns are equally distributed around a first reference circle centered upon the side branch center point.

3. The stent of claim 2, wherein the second inner turns are equally distributed around a second reference circle centered upon the side branch center point.

4. The stent of claim 1, wherein the first inner turns and the second inner turns are collectively equally distributed around the side branch center point.

5. The stent of claim 1, wherein an arc length of a first inner turn is equal to or greater than an arc length of a second inner turn.

6. The stent of claim 1, the struts of the inner serpentine ring comprising first struts and second struts, the first struts being longer than the second struts.

7. The stent of claim 6, wherein the struts of the inner serpentine ring form a repeating pattern of two adjacent first struts and two adjacent second struts.

8. The stent of claim 1, further comprising a support ring that extends continuously around the side branch structure.

9. The stent of claim 8, wherein each portion of the support ring comprises a strut width that is greater than a width of struts of the side branch structure.

10. The stent of claim 8, the support ring comprising a plurality of struts oriented in a stent longitudinal direction.

11. The stent of claim 1, wherein each connector is oriented in a side branch radial direction.

12. A stent comprising:
a plurality of interconnected framework members defining a plurality of cells, a portion of the interconnected framework members comprising a side branch structure defining an inner side branch cell, the inner side branch cell being shaped differently than other cells of the stent;
the side branch structure comprising a serpentine ring extending around the inner side branch cell and a plurality of connectors, the serpentine ring comprising alternating struts and turns, the turns comprising inner turns and outer turns, the struts comprising longer struts and shorter struts, each connector attached at one end to an inner turn, the serpentine ring comprising a repeating pattern of two adjacent longer struts and two adjacent shorter struts.

13. The stent of claim 12, the inner turns comprising alternating first inner turns and second inner turns, the second inner turns located farther away from a side branch center point than the first inner turns.

14. The stent of claim 13, wherein the first inner turns connect between two longer struts.

15. The stent of claim 13, wherein the second inner turns connect between two shorter struts.

16. The stent of claim 12, wherein adjacent longer struts are parallel to one another.

17. A stent comprising:
a plurality of interconnected framework members defining a plurality of cells, a portion of the interconnected framework members comprising a side branch structure defining an inner side branch cell, the inner side branch cell being shaped differently than other cells of the stent;
the side branch structure comprising a serpentine ring extending around the inner side branch cell and a plurality of connectors, the serpentine ring comprising alternating struts and turns, said turns comprising alternating inner turns and outer turns, each connector connected at one end to an inner turn and connected at the other end to another part of the stent;
wherein the struts of the serpentine ring located beside each of said connectors are parallel to the connector.

* * * * *